(12) United States Patent
Nuijens et al.

(10) Patent No.: US 10,752,931 B2
(45) Date of Patent: *Aug. 25, 2020

(54) DESIGNING AN ENZYMATIC PEPTIDE FRAGMENT CONDENSATION STRATEGY

(71) Applicant: EnzyPep B.V., Geleen (NL)

(72) Inventors: Timo Nuijens, Geleen (NL); Peter Jan Leonard Mario Quaedflieg, Geleen (NL)

(73) Assignee: ENZYPEP B.V., Geleen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/741,080

(22) PCT Filed: Jul. 8, 2016

(86) PCT No.: PCT/NL2016/050501
§ 371 (c)(1),
(2) Date: Dec. 29, 2017

(87) PCT Pub. No.: WO2017/007324
PCT Pub. Date: Jan. 12, 2017

(65) Prior Publication Data
US 2018/0187231 A1  Jul. 5, 2018

(30) Foreign Application Priority Data

Jul. 9, 2015  (WO) ............... PCT/NL2015/050501
Nov. 10, 2015  (WO) ............... PCT/NL2015/050784

(51) Int. Cl.
| | |
|---|---|
| *C12N 9/48* | (2006.01) |
| *C12N 9/54* | (2006.01) |
| *C12P 21/02* | (2006.01) |
| *C12Q 1/37* | (2006.01) |
| *G01N 33/68* | (2006.01) |
| *C12N 9/64* | (2006.01) |
| *C07K 1/02* | (2006.01) |

(52) U.S. Cl.
CPC ............... *C12P 21/02* (2013.01); *C07K 1/02* (2013.01); *C12N 9/6424* (2013.01); *C12Q 1/37* (2013.01); *G01N 33/6818* (2013.01); *C12Y 304/21* (2013.01)

(58) Field of Classification Search
CPC ...... C07K 7/64; C07K 19/00; C07K 2319/00; C12P 21/02; C12N 9/6424; C12Y 304/21062; C12Y 304/21; C12Q 1/04; C12Q 1/37

USPC ......... 435/252.3, 69.1, 320.1, 219, 221, 212
See application file for complete search history.

(56) References Cited

U.S. PATENT DOCUMENTS 5,155,033 A  10/1992 Estell et al.
5,403,737 A  4/1995 Abrahmsen et al.

FOREIGN PATENT DOCUMENTS

| EP | 2634193 A1 | 9/2013 |
| WO | 02/26956 A1 | 4/2002 |
| WO | 2016/056913 A1 | 4/2016 |

OTHER PUBLICATIONS

Devos et al., (Proteins: Structure, Function and Genetics, 2000, vol. 41: 98-107.*
Fetrow et al., (JMB, 1998, 281, pp. 949-968.*
Witkowski et al., (Biochemistry 38:11643-11650, 1999.*
Kisselev L., (Structure, 2002, vol. 10: 8-9.*
M.J. Page, et al, Serine Peptidases: Classification . . . , Cell. Mol. Life Sci., vol. 65, No. 7-8, 2008, XP019619934.
R.J. Siezen, et al., Homology Modelling and Protein Engineering . . . , Protein Engineering, vol. 4, No. 7, 1991, XP002008733.
International Search Report and Written Opinion for International Application No. PCT/NL2016/050501 (dated Nov. 14, 2016) (12 Pages).

* cited by examiner

*Primary Examiner* — Robert B Mondesi
*Assistant Examiner* — Mohammad Y Meah
(74) *Attorney, Agent, or Firm* — Lucas & Mercanti, LLP

(57) ABSTRACT

The invention further relates to a process for the enzymatic synthesis of an (oligo)peptide. The invention relates to a method for designing an enzymatic synthesis process of an (oligo)peptide, comprising identifying two or more (oligo) peptide fragments of an (oligo)peptide, which fragments are (oligo)peptides suitable for preparing the (oligo)peptide by enzymatic condensation of the two or more peptide fragments using a ligase. The invention relates to a method for designing an enzymatic synthesis process of a cyclic (oligo) peptide, comprising identifying a non-cyclic (oligo)peptide from which the cyclic (oligo)peptide can be prepared by cyclisation, catalysed by a cyclase. The invention further relates to a process for the enzymatic synthesis of an (oligo)peptide.

19 Claims, 4 Drawing Sheets
Specification includes a Sequence Listing.

SEQUENCE LISTING

<160> NUMBER OF SEQ ID NOS: 34

<210> SEQ ID NO 1
<211> LENGTH: 1149
<212> TYPE: DNA
<213> ORGANISM: Bacillus amyloliquefaciens

<400> SEQUENCE: 1
gtgagaggca aaaaagtatg gatcagtttg ctgtttgctt tagcgttaat ctttacgatg    60

```
gcgttcggca gcacatcctc tgcccaggcg gcagggaaat caaacgggga aagaaatat      120 attgtcgggt ttaaacagac aatgagcacg atgagcgccg ctaagaagaa agatgtcatt     180
tctgaaaaag gcgggaaagt gcaaaagcaa ttcaaatatg tagacgcagc ttcagctaca     240
ttaaacgaaa aagctgtaaa agaattgaaa aaagacccga gcgtcgctta cgttgaagaa     300
gatcacgtag cacatgcgta cgcgcagtcc gtgccttacg gcgtatcaca aattaaagcc    360
cctgctctgc actctcaagg ctacactgga tcaaatgtta aagtagcggt tatcgacagc    420
ggtatcgatt cttctcatcc tgatttaaag gtagcaggcg gagccagcat ggttccttct    480
gaaacaaatc ctttccaaga caacaactct cacggaactc acgttgccgg cacagttgcg    540
gctcttaata actcaatcgg tgtattaggc gttgcgccaa gcgcatcact ttacgctgta    600
aaagttctcg gtgctgacgg ttccggccaa tacagctgga tcattaacgg aatcgagtgg    660
gcgatcgcaa acaatatgga cgttattaac atgagcctcg gcggaccttc tggttctgct    720
gctttaaaag cggcagttga taaagccgtt gcatccggcg tcgtagtcgt tgcggcagcc    780
ggtaacgaag gcacttccgg cagctcaagc acagtgggct accctggtaa ataccttct    840 gtcattgcag taggcgctgt tgacagcagc aaccaaagag catctttctc aagcgtagga    900
cctgagcttg atgtcatggc acctggcgta tctatccaaa gcacgcttcc tggaaacaaa    960
tacggggcgt acaacggtac gtcaatggca tctccgcacg ttgccggagc ggctgctttg    1020
attctttcta gcaccccgaa ctggacaaac actcaagtcc gcagcagttt agaaaacacc    1080
actacaaaac ttggtgattc tttctactat ggaaaagggc tgatcaacgt acaggcggca    1140
gctcagtaa                                                             1149
```

<210> SEQ ID NO 2
<211> LENGTH: 275
<212> TYPE: PRT
<213> ORGANISM: Bacillus amyloliquefaciens

<400> SEQUENCE: 2

```
Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
    130                 135                 140

Ser Gly Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175
```

```
Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
    210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275

<210> SEQ ID NO 3
<211> LENGTH: 266
<212> TYPE: PRT
<213> ORGANISM: Artificial Sequence
<220> FEATURE:
<223> OTHER INFORMATION: subtilisin variant
<220> FEATURE:
<221> NAME/KEY: misc_feature
<222> LOCATION: (216)..(216)
<223> OTHER INFORMATION: Xaa can be any naturally occurring amino acid

<400> SEQUENCE: 3

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

Ser Met Val Pro Ser Glu Thr Asn Pro Phe Gln Asp Asn Asn Ser His
    50                  55                  60

Gly Thr His Val Ala Gly Thr Val Ala Ala Pro Ser Ala Ser
65                  70                  75                  80

Leu Tyr Ala Val Lys Val Leu Gly Ala Asp Gly Ser Gly Gln Tyr Ser
                85                  90                  95

Trp Ile Ile Asn Gly Ile Glu Trp Ala Ile Ala Asn Asn Met Asp Val
            100                 105                 110

Ile Asn Met Ser Leu Gly Gly Pro Ser Gly Ser Ala Ala Leu Lys Ala
        115                 120                 125

Ala Val Asp Lys Ala Val Ala Ser Gly Val Val Val Ala Ala Ala
130                 135                 140

Gly Asn Glu Gly Thr Ser Gly Ser Ser Ser Thr Val Gly Tyr Pro Gly
145                 150                 155                 160

Lys Tyr Pro Ser Val Ile Ala Val Gly Ala Val Asp Ser Ser Asn Gln
                165                 170                 175

Arg Ala Ser Phe Ser Ser Val Gly Pro Glu Leu Asp Val Met Ala Pro
            180                 185                 190

Gly Val Ser Ile Gln Ser Thr Leu Pro Gly Asn Lys Tyr Gly Ala Tyr
        195                 200                 205

Asn Gly Thr Cys Met Ala Ser Xaa His Val Ala Gly Ala Ala Ala Leu
    210                 215                 220

Ile Leu Ser Lys His Pro Asn Trp Thr Asn Thr Gln Val Arg Ser Ser
225                 230                 235                 240
```

```
Leu Glu Asn Thr Thr Thr Lys Leu Gly Asp Ser Phe Tyr Tyr Gly Lys
                245                 250                 255

Gly Leu Ile Asn Val Gln Ala Ala Ala Gln
            260                 265

<210> SEQ ID NO 4
<211> LENGTH: 266
<212> TYPE: PRT
<213> ORGANISM: Artificial Sequence
<220> FEATURE:
<223> OTHER INFORMATION: subtilisin variant
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (147)..(147)
<223> OTHER INFORMATION: Xaa can be any naturally occurring amino acid
<220> FEATURE:
<221> NAME/KEY: misc_feature
<222> LOCATION: (157)..(157)
<223> OTHER INFORMATION: Xaa can be any naturally occurring amino acid
<220> FEATURE:
<221> NAME/KEY: misc_feature
<222> LOCATION: (160)..(160)
<223> OTHER INFORMATION: Xaa can be any naturally occurring amino acid
<220> FEATURE:
<221> NAME/KEY: misc_feature
<222> LOCATION: (179)..(179)
<223> OTHER INFORMATION: Xaa can be any naturally occurring amino acid
<220> FEATURE:
<221> NAME/KEY: misc_feature
<222> LOCATION: (197)..(197)
<223> OTHER INFORMATION: Xaa can be any naturally occurring amino acid
<220> FEATURE:
<221> NAME/KEY: misc_feature
<222> LOCATION: (203)..(203)
<223> OTHER INFORMATION: Xaa can be any naturally occurring amino acid
<220> FEATURE:
<221> NAME/KEY: misc_feature
<222> LOCATION: (208)..(209)
<223> OTHER INFORMATION: Xaa can be any naturally occurring amino acid
<220> FEATURE:
<221> NAME/KEY: misc_feature
<222> LOCATION: (216)..(216)
<223> OTHER INFORMATION: Xaa can be any naturally occurring amino acid
<220> FEATURE:
<221> NAME/KEY: misc_feature
<222> LOCATION: (245)..(245)
<223> OTHER INFORMATION: Xaa can be any naturally occurring amino acid
<220> FEATURE:
```

<221> NAME/KEY: misc_feature
<222> LOCATION: (262)..(262)
<223> OTHER INFORMATION: Xaa can be any naturally occurring amino acid

<400> SEQUENCE: 4

```
Ala Xaa Xaa Val Xaa Tyr Gly Val Xaa Gln Ile Lys Ala Pro Ala Leu
1               5                   10                  15

His Ser Gln Gly Tyr Thr Gly Ser Asn Val Lys Val Ala Val Xaa Asp
            20                  25                  30

Ser Gly Ile Asp Ser Ser His Pro Asp Leu Xaa Val Ala Gly Gly Ala
        35                  40                  45

Ser Xaa Val Pro Ser Glu Thr Asn Pro Phe Gln Asp Asn Asn Ser His
    50                  55                  60

Gly Thr His Val Ala Gly Thr Val Xaa Ala Val Ala Pro Ser Ala Ser
65              70                  75                  80

Leu Tyr Ala Val Lys Val Leu Gly Ala Asp Gly Ser Gly Gln Tyr Ser
                85                  90                  95

Trp Ile Ile Asn Gly Ile Glu Trp Ala Ile Ala Asn Asn Met Asp Val
            100                 105                 110

Ile Asn Met Ser Leu Gly Gly Pro Ser Gly Ser Ala Ala Leu Lys Ala
        115                 120                 125

Ala Val Asp Lys Ala Val Ala Ser Gly Val Val Val Ala Ala Ala
    130                 135                 140

Gly Asn Xaa Gly Thr Ser Gly Ser Ser Ser Thr Val Xaa Tyr Pro Xaa
145                 150                 155                 160

Lys Tyr Pro Ser Val Ile Ala Val Gly Ala Val Asp Ser Ser Asn Gln
                165                 170                 175

Arg Ala Xaa Phe Ser Ser Val Gly Pro Glu Leu Asp Val Met Ala Pro
            180                 185                 190

Gly Val Ser Ile Xaa Ser Thr Leu Pro Gly Xaa Lys Tyr Gly Ala Xaa
        195                 200                 205

Xaa Gly Thr Cys Met Ala Ser Xaa His Val Ala Gly Ala Ala Ala Leu
    210                 215                 220

Ile Leu Ser Lys His Pro Asn Trp Thr Asn Thr Gln Val Arg Ser Ser
225                 230                 235                 240

Leu Glu Asn Thr Xaa Thr Lys Leu Gly Asp Ser Phe Tyr Tyr Gly Lys
                245                 250                 255

Gly Leu Ile Asn Val Xaa Ala Ala Ala Gln
            260                 265
```

<210> SEQ ID NO 5
<211> LENGTH: 1595
<212> TYPE: DNA
<213> ORGANISM: Artificial Sequence
<220> FEATURE:
<223> OTHER INFORMATION: segement of pBES:Ptl149DM
<220> FEATURE:
<221> NAME/KEY: promoter
<222> LOCATION: (1)..(197)
<220> FEATURE:
<221> NAME/KEY: CDS
<222> LOCATION: (198)..(1337)
<220> FEATURE:
<221> NAME/KEY: sig_peptide
<222> LOCATION: (198)..(287)
<220> FEATURE:
<221> NAME/KEY: misc_feature
<222> LOCATION: (288)..(518)
<223> OTHER INFORMATION: prodomain

<400> SEQUENCE: 5

-continued

```
actagtgttc ttttctgtat gaaaatagtt atttcgagtc tctacggaaa tagcgagaga        60
tgatatacct aaatagagat aaaatcatct caaaaaaatg ggtctactaa aatattattc       120
catctattac aataaattca cagaatagtc ttttaagtaa gtctactctg aacttaagca       180
aaaggagagg gacgcgt gtg aga ggc aaa aaa gta tgg atc agt ttg ctg          230
               Val Arg Gly Lys Lys Val Trp Ile Ser Leu Leu
                1               5                    10 ttt gct tta gcg tta atc ttt acg atg gcg ttc ggc agc aca tcc tct         278
Phe Ala Leu Ala Leu Ile Phe Thr Met Ala Phe Gly Ser Thr Ser Ser
             15                  20                  25 gcc cag gcg gca ggg aaa tca aac ggg gaa aag aaa tat att gtc ggg         326
Ala Gln Ala Ala Gly Lys Ser Asn Gly Glu Lys Lys Tyr Ile Val Gly
         30                  35                  40 ttt aaa cag aca atg agc acg atg agc gcc gct aag aag aaa gat gtc         374
Phe Lys Gln Thr Met Ser Thr Met Ser Ala Ala Lys Lys Lys Asp Val
     45                  50                  55 att tct gaa aaa ggc ggg aaa gtg caa aag caa ttc aaa tat gta gac         422
Ile Ser Glu Lys Gly Gly Lys Val Gln Lys Gln Phe Lys Tyr Val Asp
 60                  65                  70                  75 gca gct tca gct aca tta aac gaa aaa gct gta aaa gaa ttg aaa aaa         470
Ala Ala Ser Ala Thr Leu Asn Glu Lys Ala Val Lys Glu Leu Lys Lys
                 80                  85                  90 gac ccg agc gtc gct tac gtt gaa gaa gat cac gta gca cac gcg atg         518
Asp Pro Ser Val Ala Tyr Val Glu Glu Asp His Val Ala His Ala Met
             95                 100                 105 gcg aag tgc gtg tct tac ggc gta gcg caa att aaa gcc cct gct ctg         566
Ala Lys Cys Val Ser Tyr Gly Val Ala Gln Ile Lys Ala Pro Ala Leu
        110                 115                 120 cac tct caa ggc tac act gga tca aat gtt aaa gta gcg gtt ctt gac         614
His Ser Gln Gly Tyr Thr Gly Ser Asn Val Lys Val Ala Val Leu Asp
    125                 130                 135 agc ggt atc gat tct tct cat cct gat tta aac gta gca ggc gga gcc         662
Ser Gly Ile Asp Ser Ser His Pro Asp Leu Asn Val Ala Gly Gly Ala
140                 145                 150                 155 agc ttc gtt cct tct gaa aca aat cct ttc caa gac aac aac tct cac         710
Ser Phe Val Pro Ser Glu Thr Asn Pro Phe Gln Asp Asn Asn Ser His
                160                 165                 170 gga act cac gtt gcc ggc aca gtt ttg gct gtt gcg cca agc gca tca         758
Gly Thr His Val Ala Gly Thr Val Leu Ala Val Ala Pro Ser Ala Ser
            175                 180                 185 ctt tac gct gta aaa gtt ctc ggt gct gac ggt tcc ggc caa tac agc         806
Leu Tyr Ala Val Lys Val Leu Gly Ala Asp Gly Ser Gly Gln Tyr Ser
        190                 195                 200 tgg atc att aac gga atc gag tgg gcg atc gca aac aat atg gac gtt         854
Trp Ile Ile Asn Gly Ile Glu Trp Ala Ile Ala Asn Asn Met Asp Val
    205                 210                 215 att aac atg agc ctc ggc gga cct tct ggt tct gct gct tta aaa gcg         902
Ile Asn Met Ser Leu Gly Gly Pro Ser Gly Ser Ala Ala Leu Lys Ala
220                 225                 230                 235 gca gtt gat aaa gcc gtt gca tcc ggc gtc gta gtc gtt gcg gca gcc         950
Ala Val Asp Lys Ala Val Ala Ser Gly Val Val Val Val Ala Ala Ala
                240                 245                 250 ggt aac tct ggc act tcc ggc agc tca agc aca gtg agc tac cct gct         998
Gly Asn Ser Gly Thr Ser Gly Ser Ser Ser Thr Val Ser Tyr Pro Ala
            255                 260                 265 aaa tac cct tct gtc att gca gta ggc gct gtt gac agc agc aac caa        1046
Lys Tyr Pro Ser Val Ile Ala Val Gly Ala Val Asp Ser Ser Asn Gln
        270                 275                 280
```

```
aga gca ccg ttc tca agc gta gga cct gag ctt gat gtc atg gca cct      1094
Arg Ala Pro Phe Ser Ser Val Gly Pro Glu Leu Asp Val Met Ala Pro
285                 290                 295 ggc gta tct atc tgt agc acg ctt cct gga ggc aaa tac ggg gcg ctt      1142
Gly Val Ser Ile Cys Ser Thr Leu Pro Gly Gly Lys Tyr Gly Ala Leu
300                 305                 310                 315 tct ggt acg tgc atg gca tct gcg cac gtt gcc gga gcg gct gct ttg      1190
Ser Gly Thr Cys Met Ala Ser Ala His Val Ala Gly Ala Ala Ala Leu
        320                 325                 330 att ctt tct aag cac ccg aac tgg aca aac act caa gtc cgc agc agt      1238
Ile Leu Ser Lys His Pro Asn Trp Thr Asn Thr Gln Val Arg Ser Ser
335                 340                 345 tta gaa aac acc gct aca aaa ctt ggt gat tct ttc tac tat gga aaa      1286
Leu Glu Asn Thr Ala Thr Lys Leu Gly Asp Ser Phe Tyr Tyr Gly Lys
        350                 355                 360 ggg ctg atc aac gta gaa gcg gca gct cag cac cac cac cac cac cac      1334
Gly Leu Ile Asn Val Glu Ala Ala Ala Gln His His His His His His
365                 370                 375 taa aacataaaaa accggccttg gccccgccgg ttttttatta tttttcttcc           1387
tccgcatgtt caatccgctc cataatcgac ggatggctcc ctctgaaaat tttaacgaga    1447
aacggcgggt tgacccggct cagtcccgta acgccaagt cctgaaacgt ctcaatcgcc     1507
gcttcccggt ttccggtcag ctcaatgccg taacggtcgg cggcgttttc ctgataccgg    1567
gagacggcat tcgtaatcgg atggatcc                                       1595

<210> SEQ ID NO 6
<211> LENGTH: 379
<212> TYPE: PRT
<213> ORGANISM: Artificial Sequence
<220> FEATURE:
<223> OTHER INFORMATION: Synthetic Construct

<400> SEQUENCE: 6

Val Arg Gly Lys Lys Val Trp Ile Ser Leu Leu Phe Ala Leu Ala Leu
1               5                   10                  15

Ile Phe Thr Met Ala Phe Gly Ser Thr Ser Ser Ala Gln Ala Ala Gly
            20                  25                  30

Lys Ser Asn Gly Glu Lys Lys Tyr Ile Val Gly Phe Lys Gln Thr Met
        35                  40                  45

Ser Thr Met Ser Ala Ala Lys Lys Lys Asp Val Ile Ser Glu Lys Gly
    50                  55                  60

Gly Lys Val Gln Lys Gln Phe Lys Tyr Val Asp Ala Ala Ser Ala Thr
65                  70                  75                  80

Leu Asn Glu Lys Ala Val Lys Glu Leu Lys Lys Asp Pro Ser Val Ala
                85                  90                  95

Tyr Val Glu Glu Asp His Val Ala His Ala Met Ala Lys Cys Val Ser
            100                 105                 110

Tyr Gly Val Ala Gln Ile Lys Ala Pro Ala Leu His Ser Gln Gly Tyr
        115                 120                 125

Thr Gly Ser Asn Val Lys Val Ala Val Leu Asp Ser Gly Ile Asp Ser
    130                 135                 140

Ser His Pro Asp Leu Asn Val Ala Gly Gly Ala Ser Phe Val Pro Ser
145                 150                 155                 160

Glu Thr Asn Pro Phe Gln Asp Asn Asn Ser His Gly Thr His Val Ala
                165                 170                 175

Gly Thr Val Leu Ala Val Ala Pro Ser Ala Ser Leu Tyr Ala Val Lys
            180                 185                 190
```

```
Val Leu Gly Ala Asp Gly Ser Gly Gln Tyr Ser Trp Ile Ile Asn Gly
        195                 200                 205

Ile Glu Trp Ala Ile Ala Asn Asn Met Asp Val Ile Asn Met Ser Leu
    210                 215                 220

Gly Gly Pro Ser Gly Ser Ala Ala Leu Lys Ala Ala Val Asp Lys Ala
225                 230                 235                 240

Val Ala Ser Gly Val Val Val Ala Ala Gly Asn Ser Gly Thr
                245                 250                 255

Ser Gly Ser Ser Ser Thr Val Ser Tyr Pro Ala Lys Tyr Pro Ser Val
                260                 265                 270

Ile Ala Val Gly Ala Val Asp Ser Ser Asn Gln Arg Ala Pro Phe Ser
            275                 280                 285

Ser Val Gly Pro Glu Leu Asp Val Met Ala Pro Gly Val Ser Ile Cys
        290                 295                 300

Ser Thr Leu Pro Gly Gly Lys Tyr Gly Ala Leu Ser Gly Thr Cys Met
305                 310                 315                 320

Ala Ser Ala His Val Ala Gly Ala Ala Leu Ile Leu Ser Lys His
                325                 330                 335

Pro Asn Trp Thr Asn Thr Gln Val Arg Ser Ser Leu Glu Asn Thr Ala
            340                 345                 350

Thr Lys Leu Gly Asp Ser Phe Tyr Tyr Gly Lys Gly Leu Ile Asn Val
        355                 360                 365

Glu Ala Ala Ala Gln His His His His His His
        370                 375

<210> SEQ ID NO 7
<211> LENGTH: 27
<212> TYPE: DNA
<213> ORGANISM: Artificial Sequence
<220> FEATURE:
<223> OTHER INFORMATION: deleted amino acid 72-80
<220> FEATURE:
<221> NAME/KEY: CDS
<222> LOCATION: (1)..(27)

<400> SEQUENCE: 7 gtt gcg gct ctt aat aac tca atc ggt                              27
Val Ala Ala Leu Asn Asn Ser Ile Gly
1               5

<210> SEQ ID NO 8
<211> LENGTH: 9
<212> TYPE: PRT
<213> ORGANISM: Artificial Sequence
<220> FEATURE:
<223> OTHER INFORMATION: Synthetic Construct

<400> SEQUENCE: 8

Val Ala Ala Leu Asn Asn Ser Ile Gly
1               5

<210> SEQ ID NO 9
<211> LENGTH: 21
<212> TYPE: PRT
<213> ORGANISM: Artificial Sequence
<220> FEATURE:
<223> OTHER INFORMATION: fragment for synthesis of Exenatide
<220> FEATURE:
<221> NAME/KEY: THIOETH
<222> LOCATION: (21)..(21)

<400> SEQUENCE: 9
```

```
His Gly Glu Gly Thr Phe Thr Ser Asp Leu Ser Lys Gln Met Glu Glu
1               5                   10                  15

Glu Ala Val Arg Leu
            20

<210> SEQ ID NO 10
<211> LENGTH: 18
<212> TYPE: PRT
<213> ORGANISM: Artificial Sequence
<220> FEATURE:
<223> OTHER INFORMATION: segment for synthesis of Exenatide
<220> FEATURE:
<221> NAME/KEY: MOD_RES
<222> LOCATION: (18)..(18)
<223> OTHER INFORMATION: AMIDATION

<400> SEQUENCE: 10

Phe Ile Glu Trp Leu Lys Asn Gly Gly Pro Ser Ser Gly Ala Pro Pro
1               5                   10                  15

Pro Ser

<210> SEQ ID NO 11
<211> LENGTH: 24
<212> TYPE: PRT
<213> ORGANISM: Artificial Sequence
<220> FEATURE:
<223> OTHER INFORMATION: segemnt for synthesis of Exenatide
<220> FEATURE:
<221> NAME/KEY: THIOETH
<222> LOCATION: (24)..(24)

<400> SEQUENCE: 11

His Gly Glu Gly Thr Phe Thr Ser Asp Leu Ser Lys Gln Met Glu Glu
1               5                   10                  15

Glu Ala Val Arg Leu Phe Ile Glu
            20

<210> SEQ ID NO 12
<211> LENGTH: 15
<212> TYPE: PRT
<213> ORGANISM: Artificial Sequence
<220> FEATURE:
<223> OTHER INFORMATION: segemnt for synthesis of Exenatide
<220> FEATURE:
<221> NAME/KEY: MOD_RES
<222> LOCATION: (15)..(15)
<223> OTHER INFORMATION: AMIDATION

<400> SEQUENCE: 12

Trp Leu Lys Asn Gly Gly Pro Ser Ser Gly Ala Pro Pro Pro Ser
1               5                   10                  15

<210> SEQ ID NO 13
<211> LENGTH: 19
<212> TYPE: PRT
<213> ORGANISM: Artificial Sequence
<220> FEATURE:
<223> OTHER INFORMATION: segment for synthesis
<220> FEATURE:
<221> NAME/KEY: misc_feature
<222> LOCATION: (16)..(18)
<223> OTHER INFORMATION: Xaa can be any naturally occurring amino acid
<220> FEATURE:
<221> NAME/KEY: MOD_RES
<222> LOCATION: (19)..(19)
<223> OTHER INFORMATION: AMIDATION

<400> SEQUENCE: 13
```

```
Trp Leu Lys Asn Gly Gly Pro Ser Ser Gly Ala Pro Pro Ser Xaa
1               5                   10                  15

Xaa Xaa Xaa

<210> SEQ ID NO 14
<211> LENGTH: 14
<212> TYPE: PRT
<213> ORGANISM: Artificial Sequence
<220> FEATURE:
<223> OTHER INFORMATION: segment for synthesis of thymosin-alpha
<220> FEATURE:
<221> NAME/KEY: MOD_RES
<222> LOCATION: (1)..(1)
<223> OTHER INFORMATION: ACETYLATION
<220> FEATURE:
<221> NAME/KEY: THIOETH
<222> LOCATION: (14)..(14)

<400> SEQUENCE: 14

Ser Asp Ala Ala Val Asp Thr Ser Ser Glu Ile Thr Thr Lys
1               5                   10

<210> SEQ ID NO 15
<211> LENGTH: 14
<212> TYPE: PRT
<213> ORGANISM: Artificial Sequence
<220> FEATURE:
<223> OTHER INFORMATION: segment for synthesis of thymosin-alpha

<400> SEQUENCE: 15

Asp Leu Lys Glu Lys Lys Glu Val Val Glu Glu Ala Glu Asn
1               5                   10

<210> SEQ ID NO 16
<211> LENGTH: 21
<212> TYPE: PRT
<213> ORGANISM: Artificial Sequence
<220> FEATURE:
<223> OTHER INFORMATION: fragment for synthesis of Lixisenatide
<220> FEATURE:
<221> NAME/KEY: THIOETH
<222> LOCATION: (21)..(21)

<400> SEQUENCE: 16

His Gly Glu Gly Thr Phe Thr Ser Asp Leu Ser Lys Gln Met Glu Glu
1               5                   10                  15

Glu Ala Val Arg Leu
            20

<210> SEQ ID NO 17
<211> LENGTH: 23
<212> TYPE: PRT
<213> ORGANISM: Artificial Sequence
<220> FEATURE:
<223> OTHER INFORMATION: segment for synthesis of Lixisenatide
<220> FEATURE:
<221> NAME/KEY: MOD_RES
<222> LOCATION: (23)..(23)
<223> OTHER INFORMATION: AMIDATION

<400> SEQUENCE: 17

Phe Ile Glu Trp Leu Lys Asn Gly Gly Pro Ser Ser Gly Ala Pro Pro
1               5                   10                  15

Ser Lys Lys Lys Lys Lys Lys
            20
```

```
<210> SEQ ID NO 18
<211> LENGTH: 28
<212> TYPE: PRT
<213> ORGANISM: Artificial Sequence
<220> FEATURE:
<223> OTHER INFORMATION: thymosin-alpha-1

<400> SEQUENCE: 18

Ser Asp Ala Ala Val Asp Thr Ser Ser Glu Ile Thr Thr Lys Asp Leu
1               5                   10                  15

Lys Glu Lys Lys Glu Val Val Glu Glu Ala Glu Asn
            20                  25

<210> SEQ ID NO 19
<211> LENGTH: 14
<212> TYPE: PRT
<213> ORGANISM: Artificial Sequence
<220> FEATURE:
<223> OTHER INFORMATION: thymosin-alpha-1 fragment

<400> SEQUENCE: 19

Ser Asp Ala Ala Val Asp Thr Ser Ser Glu Ile Thr Thr Lys
1               5                   10

<210> SEQ ID NO 20
<211> LENGTH: 14
<212> TYPE: PRT
<213> ORGANISM: Artificial Sequence
<220> FEATURE:
<223> OTHER INFORMATION: thymosin-alpha-1 fragment

<400> SEQUENCE: 20

Asp Leu Lys Glu Lys Lys Glu Val Val Glu Glu Ala Glu Asn
1               5                   10

<210> SEQ ID NO 21
<211> LENGTH: 39
<212> TYPE: PRT
<213> ORGANISM: Artificial Sequence
<220> FEATURE:
<223> OTHER INFORMATION: Exenatide
<220> FEATURE:
<221> NAME/KEY: MOD_RES
<222> LOCATION: (39)..(39)
<223> OTHER INFORMATION: AMIDATION

<400> SEQUENCE: 21

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 22
<211> LENGTH: 11
<212> TYPE: PRT
<213> ORGANISM: Artificial Sequence
<220> FEATURE:
<223> OTHER INFORMATION: Exenatide fragment

<400> SEQUENCE: 22

Met Glu Glu Glu Ala Val Arg Leu Phe Ile Glu
1               5                   10

<210> SEQ ID NO 23
```

```
<211> LENGTH: 13
<212> TYPE: PRT
<213> ORGANISM: Artificial Sequence
<220> FEATURE:
<223> OTHER INFORMATION: Exenatide fragment

<400> SEQUENCE: 23

His Gly Glu Gly Thr Phe Thr Ser Asp Leu Ser Lys Gln
1               5                   10

<210> SEQ ID NO 24
<211> LENGTH: 10
<212> TYPE: PRT
<213> ORGANISM: Artificial Sequence
<220> FEATURE:
<223> OTHER INFORMATION: Exenatide fragment

<400> SEQUENCE: 24

Glu Glu Glu Ala Val Arg Leu Phe Ile Glu
1               5                   10

<210> SEQ ID NO 25
<211> LENGTH: 15
<212> TYPE: PRT
<213> ORGANISM: Artificial Sequence
<220> FEATURE:
<223> OTHER INFORMATION: Exenatide fragment
<220> FEATURE:
<221> NAME/KEY: MOD_RES
<222> LOCATION: (15)..(15)
<223> OTHER INFORMATION: AMIDATION

<400> SEQUENCE: 25

Trp Leu Lys Asn Gly Gly Pro Ser Ser Gly Ala Pro Pro Pro Ser
1               5                   10                  15

<210> SEQ ID NO 26
<211> LENGTH: 13
<212> TYPE: PRT
<213> ORGANISM: Artificial Sequence
<220> FEATURE:
<223> OTHER INFORMATION: cyclic peptide
<220> FEATURE:
<221> NAME/KEY: BINDING
<222> LOCATION: (1)..(13)

<400> SEQUENCE: 26

Ala Cys Lys Asn Gly Gln Thr Asn Cys Tyr Gln Ser Tyr
1               5                   10

<210> SEQ ID NO 27
<211> LENGTH: 43
<212> TYPE: PRT
<213> ORGANISM: Artificial Sequence
<220> FEATURE:
<223> OTHER INFORMATION: Lixisenatide
<220> FEATURE:
<221> NAME/KEY: MOD_RES
<222> LOCATION: (43)..(43)
<223> OTHER INFORMATION: AMIDATION

<400> SEQUENCE: 27

His Gly Glu Gly Thr Phe Ser Asp Leu Ser Lys Gln Met Glu Glu
1               5                   10                  15

Ala Val Arg Leu Phe Ile Glu Trp Leu Lys Asn Gly Gly Pro Ser Ser
                20                  25                  30

Gly Ala Pro Pro Ser Lys Lys Lys Lys Lys Lys
            35                  40
```

<210> SEQ ID NO 28
<211> LENGTH: 20
<212> TYPE: PRT
<213> ORGANISM: Artificial Sequence
<220> FEATURE:
<223> OTHER INFORMATION: Lixisenatide fragment
<220> FEATURE:
<221> NAME/KEY: MOD_RES
<222> LOCATION: (20)..(20)
<223> OTHER INFORMATION: AMIDATION

<400> SEQUENCE: 28

Trp Leu Lys Asn Gly Gly Pro Ser Ser Gly Ala Pro Pro Ser Lys Lys
1               5                   10                  15

Lys Lys Lys Lys
            20

<210> SEQ ID NO 29
<211> LENGTH: 20
<212> TYPE: PRT
<213> ORGANISM: Artificial Sequence
<220> FEATURE:
<223> OTHER INFORMATION: Lixisxenatide fragment

<400> SEQUENCE: 29

His Gly Glu Gly Thr Phe Ser Asp Leu Ser Lys Gln Met Glu Glu Glu
1               5                   10                  15

Ala Val Arg Leu
            20

<210> SEQ ID NO 30
<211> LENGTH: 23
<212> TYPE: PRT
<213> ORGANISM: Artificial Sequence
<220> FEATURE:
<223> OTHER INFORMATION: Lixisenatide fragment

<400> SEQUENCE: 30

Phe Ile Glu Trp Leu Lys Asn Gly Gly Pro Ser Ser Gly Ala Pro Pro
1               5                   10                  15

Ser Lys Lys Lys Lys Lys Lys
            20

<210> SEQ ID NO 31
<211> LENGTH: 5
<212> TYPE: PRT
<213> ORGANISM: Artificial Sequence
<220> FEATURE:
<223> OTHER INFORMATION: fragment for coupling to insulin
<220> FEATURE:
<221> NAME/KEY: MOD_RES
<222> LOCATION: (1)..(1)
<223> OTHER INFORMATION: ACETYLATION

<400> SEQUENCE: 31

Asp Phe Ser Lys Leu
1               5

<210> SEQ ID NO 32
<211> LENGTH: 23
<212> TYPE: PRT
<213> ORGANISM: Artificial Sequence
<220> FEATURE:
<223> OTHER INFORMATION: non cyclic oligopeptide fragment

<400> SEQUENCE: 32

Gly Ile Gly Thr Pro Ile Ser Phe Tyr Gly Gly Gly Ala Gly His Val
1               5                   10                  15

Pro Glu Tyr Phe Val Gly Ile
            20

<210> SEQ ID NO 33
<211> LENGTH: 23
<212> TYPE: PRT
<213> ORGANISM: Artificial Sequence
<220> FEATURE:
<223> OTHER INFORMATION: non-cyclic oligopeptide fragment

<400> SEQUENCE: 33

Gly Gly Gly Ala Gly His Val Pro Glu Tyr Phe Val Gly Ile Gly Ile
1               5                   10                  15

Gly Thr Pro Ile Ser Phe Tyr
            20

<210> SEQ ID NO 34
<211> LENGTH: 587
<212> TYPE: PRT
<213> ORGANISM: Artificial Sequence
<220> FEATURE:
<223> OTHER INFORMATION: extende HSA

<400> SEQUENCE: 34

Ser Tyr Arg Asp Ala His Lys Ser Glu Val Ala His Arg Phe Lys Asp
1               5                   10                  15

Leu Gly Glu Glu Asn Phe Lys Ala Leu Val Leu Ile Ala Phe Ala Gln
            20                  25                  30

Tyr Leu Gln Gln Cys Pro Phe Glu Asp His Val Lys Leu Val Asn Glu
        35                  40                  45

Val Thr Glu Phe Ala Lys Thr Cys Val Ala Asp Glu Ser Ala Glu Asn
    50                  55                  60

Cys Asp Lys Ser Leu His Thr Leu Phe Gly Asp Lys Leu Cys Thr Val
65                  70                  75                  80

Ala Thr Leu Arg Glu Thr Tyr Gly Glu Met Ala Asp Cys Cys Ala Lys
                85                  90                  95

Gln Glu Pro Glu Arg Asn Glu Cys Phe Leu Gln His Lys Asp Asp Asn
            100                 105                 110

Pro Asn Leu Pro Arg Leu Val Arg Pro Glu Val Asp Val Met Cys Thr
        115                 120                 125

Ala Phe His Asp Asn Glu Glu Thr Phe Leu Lys Lys Tyr Leu Tyr Glu
    130                 135                 140

Ile Ala Arg Arg His Pro Tyr Phe Tyr Ala Pro Glu Leu Leu Phe Phe
145                 150                 155                 160

Ala Lys Arg Tyr Lys Ala Ala Phe Thr Glu Cys Cys Gln Ala Ala Asp
                165                 170                 175

Lys Ala Ala Leu Leu Pro Lys Leu Asp Glu Leu Arg Asp Glu Gly Lys
            180                 185                 190

Ala Ser Ser Ala Lys Gln Arg Leu Lys Cys Ala Ser Leu Gln Lys Phe
        195                 200                 205

Gly Glu Arg Ala Phe Lys Ala Trp Ala Val Ala Arg Leu Ser Gln Arg
    210                 215                 220

Phe Pro Lys Ala Glu Phe Ala Glu Val Ser Lys Leu Val Thr Asp Leu
225                 230                 235                 240

Thr Lys Val His Thr Glu Cys Cys His Gly Asp Leu Leu Glu Cys Ala

```
                    245                 250                 255
Asp Asp Arg Ala Asp Leu Ala Lys Tyr Ile Cys Glu Asn Gln Asp Ser
            260                 265                 270

Ile Ser Ser Lys Leu Lys Glu Cys Cys Glu Lys Pro Leu Leu Glu Lys
            275                 280                 285

Ser His Cys Ile Ala Glu Val Glu Asn Asp Glu Met Pro Ala Asp Leu
    290                 295                 300

Pro Ser Leu Ala Ala Asp Phe Val Glu Ser Lys Asp Val Cys Lys Asn
305             310                 315                     320

Tyr Ala Glu Ala Lys Asp Val Phe Leu Gly Met Phe Leu Tyr Glu Tyr
            325                 330                 335

Ala Arg Arg His Pro Asp Tyr Ser Val Val Leu Leu Leu Arg Leu Ala
            340                 345                 350

Lys Thr Tyr Glu Thr Thr Leu Glu Lys Cys Cys Ala Ala Ala Asp Pro
            355                 360                 365

His Glu Cys Tyr Ala Lys Val Phe Asp Glu Phe Lys Pro Leu Val Glu
    370                 375                 380

Glu Pro Gln Asn Leu Ile Lys Gln Asn Cys Glu Leu Phe Glu Gln Leu
385             390                 395                     400

Gly Glu Tyr Lys Phe Gln Asn Ala Leu Leu Val Arg Tyr Thr Lys Lys
            405                 410                 415

Val Pro Gln Val Ser Thr Pro Thr Leu Val Glu Val Ser Arg Asn Leu
            420                 425                 430

Gly Lys Val Gly Ser Lys Cys Cys Lys His Pro Glu Ala Lys Arg Met
            435                 440                 445

Pro Cys Ala Glu Asp Tyr Leu Ser Val Val Leu Asn Gln Leu Cys Val
    450                 455                 460

Leu His Glu Lys Thr Pro Val Ser Asp Arg Val Thr Lys Cys Cys Thr
465             470                 475                     480

Glu Ser Leu Val Asn Arg Arg Pro Cys Phe Ser Ala Leu Glu Val Asp
            485                 490                 495

Glu Thr Tyr Val Pro Lys Glu Phe Asn Ala Glu Thr Phe Thr Phe His
            500                 505                 510

Ala Asp Ile Cys Thr Leu Ser Glu Lys Glu Arg Gln Ile Lys Lys Gln
            515                 520                 525

Thr Ala Leu Val Glu Leu Val Lys His Lys Pro Lys Ala Thr Lys Glu
            530                 535                 540

Gln Leu Lys Ala Val Met Asp Asp Phe Ala Ala Phe Val Glu Lys Cys
545             550                 555                     560

Cys Lys Ala Asp Asp Lys Glu Thr Cys Phe Ala Glu Glu Gly Lys Lys
                565                 570                 575

Leu Val Ala Ala Ser Gln Ala Ala Leu Gly Leu
            580                 585
```

DESIGNING AN ENZYMATIC PEPTIDE FRAGMENT CONDENSATION STRATEGY

CROSS-REFERENCE TO RELATED APPLICATIONS

This application is a 371 of PCT/NL2016/050501, filed Jul. 8, 2016, which claims the benefit of Netherlands Patent Application Nos. PCT/NL2015/050501, filed Jul. 9, 2015 and PCT/NL2015/050784, filed Nov. 10, 2015.

FIELD OF THE INVENTION

The invention relates to a method for designing an enzymatic synthesis process of an (oligo)peptide (i.e. a peptide, in particular an oligopeptide). The invention further relates to a process for enzymatically synthesizing an (oligo)peptide, wherein a first (oligo)peptide fragment and a second (oligo)peptide fragment that have been identified by a method according to the invention are enzymatically coupled. The invention further relates to a process for enzymatically synthesizing a cyclic (oligo)peptide from a non-cyclic (oligo)peptide that has been identified by a method according to the invention. The invention further relates to a process for enzymatically synthesizing a number of specific oligopeptides. The invention further relates to a subtilisin BPN' variant or homologue thereof.

BACKGROUND OF THE INVENTION

Peptides, in particular oligopeptides have many applications, for instance as pharmaceutical, food or feed ingredient, or cosmetic ingredient.

Processes for synthesizing (oligo)peptides are generally known in the art. Oligopeptides can be chemically synthesized in a stepwise fashion in solution or on the solid phase via highly optimized processes. However, peptides longer than 10-15 amino acids are often very difficult to synthesize due to side reactions and as a consequence purification is troublesome. Therefore, peptides longer than 10 amino acids are often synthesized by a combination of solid-phase synthesis of side-chain protected oligopeptide fragments which are subsequently chemically condensed in solution, e.g. as in a 10+10 condensation to make a peptide of 20 amino acids. The major drawback of chemical side-chain protected oligopeptide fragment condensation is that upon activation of the C-terminal amino acid residue of the acyl donor racemisation occurs. In contrast, enzyme-catalysed peptide couplings are completely devoid of racemisation and have several other advantages over chemical peptide synthesis such as the absence of side reactions on the side-chain functionalities. For industrial application, an enzymatic peptide synthesis concept based on a kinetic approach, i.e. using an acyl donor C-terminal ester is most attractive (see for instance N. Sewald and H.-D. Jakubke, in: "Peptides: Chemistry and Biology", 1st reprint, Ed. Wiley-VCH Verlag GmbH, Weinheim 2002).

Chemo-enzymatic peptide synthesis can entail the enzymatic coupling of oligopeptide fragments which have individually been synthesized using chemical synthesis, fermentation, or by a combination of chemical and enzymatic coupling steps. Some reports have been published on the enzymatic condensation of oligopeptide fragments in aqueous solution (Kumaran et al. Protein Science, 2000, 9, 734; Bjorup et al. Bioorg. Med. Chem. 1998, 6, 891; Homandberg et al. Biochemistry, 1981, 21, 3387; Komoriya et al. Int. J. Pep. Prot. Res. 1980, 16, 433).

It was found by Wells et al. (U.S. Pat. No. 5,403,737) that the condensation of oligopeptides in aqueous solution could be significantly improved by altering the active site of subtilisin BPN', a subtilisin from *B. amyloliquefaciens* (SEQUENCE ID NO: 2). When two mutations were introduced, i.e. S221C and P225A, a subtilisin BPN' variant called subtiligase was obtained having a 500-fold increased synthesis over hydrolysis ratio (S/H ratio) as compared to wild-type subtilisin BPN'. In further experiments Wells et al. added five additional mutations to subtiligase, i.e. M50F, N76D, N109S, K213R and N218S, to make the enzyme more stable (Proc. Natl. Acad. Sci. USA, 1994, 91, 12544). The new mutant called stabiligase appeared moderately more resistant to sodium dodecasulphate and guanidinium hydrochloride, but hydrolysis was still a major side reaction. For instance an (oligo)peptide carboxyamidomethyl-ester (Cam-ester) was ligated to an (oligo)peptide amine using stabiligase in a yield of 44%. In this example, 10 equivalents of the (oligo)peptide C-terminal ester were used and thus, 9.56 equivalents of the (oligo)peptide C-terminal ester were hydrolyzed at the C-terminal ester functionality and only 0.44 equivalents ligated to the (oligo)peptide amine to form the product. Probably for this reason, the past 20 years subtiligase nor stabiligase have been industrially applied in enzymatic peptide synthesis, to the best of the inventors knowledge.

In post-published WO 2016/056913 (claiming priority of PCT/NL2014/050707) a solution is provided for the undesirably high hydrolytic activity encountered with enzymes like subtiligase or stabiligase when used for (oligo)peptide synthesis in an aqueous environment, by providing a subtilisin BPN' variant or a homologue thereof, which comprises the following mutations compared to subtilisin BPN' represented by SEQUENCE ID NO: 2 or a homologue sequence thereof:

a deletion of the amino acids corresponding to positions 75-83;
a mutation at the amino acid position corresponding to S221, the mutation being S221C;
a mutation at the amino acid position corresponding to P225, said mutation being P225A;

The present inventors realized that for enzymatic (oligo)peptide synthesis to obtain a certain peptide product at will there is not only room for improvement by identifying enzymes which have a good synthesis over hydrolysis ratio, but also in selecting which (oligo)peptide fragments to use for assembling the (oligo)peptide of interest. As will be understood by the skilled person, from the amino acid sequence of the (oligo)peptide it can be determined which different fragments (two or more) can at least theoretically be coupled together in the right order to result in the (oligo)peptide of interest. However, from the amino acid sequence of the (oligo)peptide for the enzymatic coupling(s) as such it does generally not follow which coupling position or positions would be optimal, especially not if the (oligo)peptide is large, e.g. having 8 or more, in particular 12 or more, more in particular 20 or more amino acid units. Designing a desirable coupling strategy, which should offer a synthesis process with satisfactory selectivity and coupling yield requires determining the number of fragments and the length of each of the fragments (which define the coupling position) to be used in the enzymatic synthesis, which development is therefore a complicated, often lengthy, task requiring multiple trial-and-error approaches.

Specific examples of oligopeptides for which it would be desired to design an enzymatic synthesis process include Exenatide, Thymosin alpha 1 and Lixisenatide. Exenatide is an oligopeptide that can be used as adjunctive therapy to improve glycemic control in patients with type 2 diabetes mellitus who are taking metformin, but have not achieved adequate glycemic control.

Exenatide is difficult to prepare via classical chemical synthesis since it is a long oligopeptide, i.e. having 39 amino acids, and is virtually impossible to produce via known fragment condensation methodology due to racemisation, since there are no Gly or Pro residues present at strategic positions. Generally, the full solid-phase-synthesis of a 39 amino acid long peptide results in purified yields of around 10-20%, corresponding to 95-96% yield per step. Due to the inefficient synthesis of Exenatide (10-15% overall yield on large scale) cost prices for this medicine are extremely high.

Similar problems with known synthesis methodology apply to the synthesis of Lixisenatide, a variant of Exenatide with increased water-solubility, having 44 amino acids. The overall yield for Lixisenatide is even worse and cost-prices are even higher.

Thymosin alpha 1 is an enhancer of cell-mediated immunity. It does not contain any Gly or Pro residue's and is thus impossible to produce chemically (non-enzymatically) via fragment condensation. Thymosin alpha 1 is a classic example of a peptide that is extremely difficult to produce via full solid phase peptide synthesis due to hydrophobic collapse. When standard solid phase methods are applied for the synthesis of the 28 amino acid long Thymosin alpha 1, crude yields of 10% have been reported (Fernando Albericio, Journal of Peptide Science, 2009, 92, 565-572). On large scale, three consecutive preparative HPLC purifications are needed to obtain an acceptable purity of the product.

Clearly, there is a need for new technologies to improve the synthesis, overall yield and cost-prices of many pharmaceutical peptides, such as Exenatide, Lixisenatide, Thymosin alpha 1 and analogues thereof.

The inventors further realized that there is a need for an improved method of designing a process for the enzymatic synthesis of a cyclic (oligo)peptide, since from the amino acid sequence of a cyclic (oligo)peptide it is generally not evident which non-cyclic (oligo)peptide would be enzymatically cyclized adequately by coupling its C-terminal end and N-terminal end to form a peptide bond; after all the number of non-cyclic (oligo)peptides that have an amino acid sequence from which the cyclic (oligo)peptide can (conceptually) be composed by cyclisation of both ends is typically equal to the number of peptide bonds in the cyclic (oligo)peptide.

SUMMARY OF THE INVENTION

It is an object of the present invention to provide a method which allows the identification of (oligo)peptide fragments useful to synthesize an (oligo)peptide by using enzymatic condensation(s), catalysed by one or more ligase(s), respectively a method which allows the identification of a non-cyclic (oligo)peptide, to synthesize a cyclic (oligo)peptide from, using enzymatic condensation, catalysed by a cyclase, thus providing a way to design an enzymatic synthesis process for the (oligo)peptide. There is in general a need for such a method, at least because it would be helpful in the development of an alternative process for synthesizing an (oligo)peptide. In particular, there is a need for such a method that would simplify designing a suitable enzymatic (oligo)peptide synthesis process, that would reduce the (average) time needed to design a satisfactory enzymatic (oligo)peptide synthesis process, or even a method that would offer an improved synthesis process, in particular in that overall yield or selectivity is improved, compared to an otherwise the same process wherein different fragments are used to synthesize an (oligo)peptide of interest or wherein a non-cyclic (oligo)peptide is used to synthesize a cyclic (oligo)peptide.

It is a further object of the invention to provide a method for designing a process allowing the enzymatic coupling of an (oligo)peptide to a protein. It is in particular a challenge to provide enzymatic processes that allow coupling of a peptide with a protein, in particular due to the added complexity of a protein's three-dimensional structure.

It is further an object of the invention to provide a novel process of enzymatically synthesizing an (oligo)peptide.

There is a need for alternative enzymatic peptide synthesis processes in general, in particular in order to broaden the palette of tools for making specific (oligo)peptides. In particular, there is a need for an enzymatic (oligo)peptide synthesis process that offers an improved overall yield or an improved selectivity.

It is further an object of the invention to provide a hydrolytic enzyme that is useful in a method for identifying the (oligo)peptide fragments or the non-cyclic (oligo)peptide, respectively a ligase or cyclase that is useful in a process for synthesizing an (oligo)peptide of the invention from these identified fragments.

One or more other objects that may be subject of the invention follow from the description below.

The inventors found that it is possible to develop a process for the synthesis of (oligo)peptides by enzymatic condensation of two or more peptide fragments using a ligase, on the basis of enzymatic hydrolysis of a sample of the (oligo)peptide to be synthesized, using a protease that comprises a specific modification in its amino acid sequence, compared to the ligase.

Accordingly, the invention relates to a method for designing an enzymatic synthesis process of an (oligo)peptide, comprising identifying two or more (oligo)peptide fragments of an (oligo)peptide, which fragments are (oligo)peptides suitable for preparing the (oligo)peptide by enzymatic condensation of the two or more peptide fragments using a ligase, which ligase is a variant of a serine endoprotease having a mutation of a serine in a hydrolytically active site of the serine endoprotease, which mutation is a substitution into cystein or selenocystein,
the method comprising determining the amino acid sequence of the fragments obtained by enzymatic hydrolysis of a sample of the (oligo)peptide or a or a sample of a segment of the (oligo)peptide by the serine endoprotease of which the ligase is a variant.

Further, the invention relates to a method for identifying two or more (oligo)peptide fragments of an (oligo)peptide, which fragments are (oligo)peptides suitable for preparing the (oligo)peptide by enzymatic condensation of the two or more (oligo)peptide fragments using a ligase, which ligase is a variant of a serine endoprotease having a mutation of a serine in a hydrolytically active site of the serine endoprotease, which mutation is a substitution into cystein or selenocystein, the method comprising determining the amino acid sequence of the fragments obtained by enzymatic hydrolysis of a sample of the (oligo)peptide or a segment of the (oligo)peptide by the serine endoprotease of which the ligase is a variant.

Further, the inventors found that it is possible to develop a process for the synthesis of cyclic (oligo)peptides by cyclisation of non-cyclic, preferably linear, (oligo)peptide C-terminal ester or thioester having an N-terminally unprotected amine using a cyclase, on the basis of enzymatic hydrolysis of a sample of the cyclic (oligo)peptide to be synthesized, using a protease that comprises a specific modification in its amino acid sequence, compared to the ligase.

Accordingly, the invention further relates to a method for designing an enzymatic synthesis process of a cyclic (oligo) peptide of at least 12 amino acids, comprising identifying a non-cyclic (oligo)peptide, in particular a linear (oligo)peptide, which linear (oligo)peptide is suitable for preparing the cyclic (oligo)peptide by enzymatic cyclisation of the non-cyclic (oligo)peptide using a cyclase, which cyclase is a variant of a serine endoprotease, having a mutation of a serine in a hydrolytically active site of the serine endoprotease, which mutation is a substitution into cystein or selenocystein, the method comprising determining the amino acid sequence of a fragment obtained by the enzymatic hydrolysis of a sample of the cyclic (oligo)peptide or a sample of a segment of the cyclic (oligo)peptide by the serine endoprotease of which the cyclase is a variant.

Further, the invention relates to a process for enzymatically synthesizing an (oligo)peptide, wherein a first (oligo) peptide fragment and a second (oligo)peptide fragment of which the amino acid sequences have been determined by a method according to the invention are enzymatically coupled using a ligase, wherein the first is fragment an (oligo)peptide C-terminal ester or thioester, and the second fragment is an (oligo)peptide nucleophile having an N-terminally unprotected amine.

Further, the invention relates to a process for enzymatically synthesizing a cyclic (oligo)peptide of at least 12 amino acid units, wherein a non-cyclic, preferably linear, (oligo)peptide C-terminal ester or thioester having an N-terminally unprotected amine of which the amino acid sequence has been identified in a method according to the invention is subjected to a cyclisation step, wherein the C-terminal end and the N-terminal end of the (oligo)peptide C-terminal ester or thioester are coupled to form a peptide bond, which cyclisation step is catalysed using a cyclase. An example of a cyclic peptide that can be prepared in accordance with the invention is Microcin J25.

Amongst others, a method for designing an enzymatic synthesis process according to the invention has been found suitable to determine suitable ligases and (oligo)peptide fragments for the enzymatic synthesis of several (oligo) peptides with pharmaceutical activity for which (oligo) peptides a strong need exists for alternative, in particular improved synthesis methodology—such as for Exenatide, Thymosin alpha. 1, Lixisenatide or an analogue of any of these oligopeptides.

Accordingly, the invention further relates to a process for enzymatically synthesizing Exenatide from a first (oligo) peptide fragment and a second (oligo)peptide fragment, wherein the first fragment is an (oligo)peptide C-terminal ester or thioester, which is enzymatically coupled to the second fragment, which second fragment is an (oligo)peptide nucleophile having an N-terminally unprotected amine, which coupling is catalysed by a ligase.

Accordingly, the invention further relates to a process for enzymatically synthesizing Thymosin-alpha-1 from a first (oligo)peptide fragment and a second (oligo)peptide fragment, wherein the first fragment is an (oligo)peptide C-terminal ester or thioester, which is enzymatically coupled to the second fragment, which second fragment is an (oligo) peptide nucleophile having an N-terminally unprotected amine, which coupling is catalysed by a ligase.

Accordingly, the invention further relates to a process for enzymatically synthesizing Lixisenatide from a first (oligo) peptide fragment and a second (oligo)peptide fragment, wherein the first fragment is an (oligo)peptide C-terminal ester or thioester, which is enzymatically coupled to the second fragment, which second fragment is an (oligo)peptide nucleophile having an N-terminally unprotected amine, which coupling is catalysed by a ligase.

In a further aspect, the invention relates to designing an enzymatic synthesis process wherein an (oligo)peptide, in particular a pharmaceutically active (oligo)peptide, such as Exenatide, Lixisenatide, Thymosin alpha 1 or an analogue thereof, is coupled to a protein, such as an albumin or an immunoglobulin.

The invention further relates to a process for enzymatically synthesizing a conjugate of an (oligo)peptide, in particular a pharmaceutically active (oligo)peptide, (as a first fragment) and a protein (as a second fragment, wherein the first fragment is an (oligo)peptide C-terminal ester or thioester, which is enzymatically coupled to the second fragment, which second fragment is an (oligo)peptide nucleophile having an N-terminally unprotected amine, which coupling is catalysed by a ligase. Preferred first fragments are Exenatide, Lixisenatide, Thymosin alpha 1 and analogues thereof. Preferred proteins are albumins (such as human serum albumin) and immunoglobulins.

Further, the invention relates to a subtilisin BPN' variant or homologue thereof as defined herein having serine endoprotease activity, the subtilisin BPN' variant or homologue thereof having:
  a deletion of the amino acids corresponding to positions 75-83;
  a serine at the amino acid position corresponding to S221;
  a mutation at the amino acid position corresponding to P225 selected from the group of P225N, P225D, P225S, P225C, P225G, P225A, P225T, P225V, P225I, P225L, P225H and P225Q;
wherein the amino acid positions are defined according to the sequence of subtilisin BPN' represented by SEQUENCE ID NO: 2.

The subtilisin BPN' variant or homologue thereof is useful as a catalyst, in particular for catalysing the hydrolysis of a peptide bond.

Further, the invention relates to a polynucleotide, in particular a recombinant polynucleotide, encoding an enzyme of the invention. The recombinant polynucleotide of the invention is typically synthetic. The invention in particular extends to DNA or RNA isolated from any organism. In a specific embodiment, the invention extends to a host cell comprising recombinant DNA according to the invention. The host cell is typically transgenic.

DETAILED DESCRIPTION OF THE INVENTION

Figure 1:
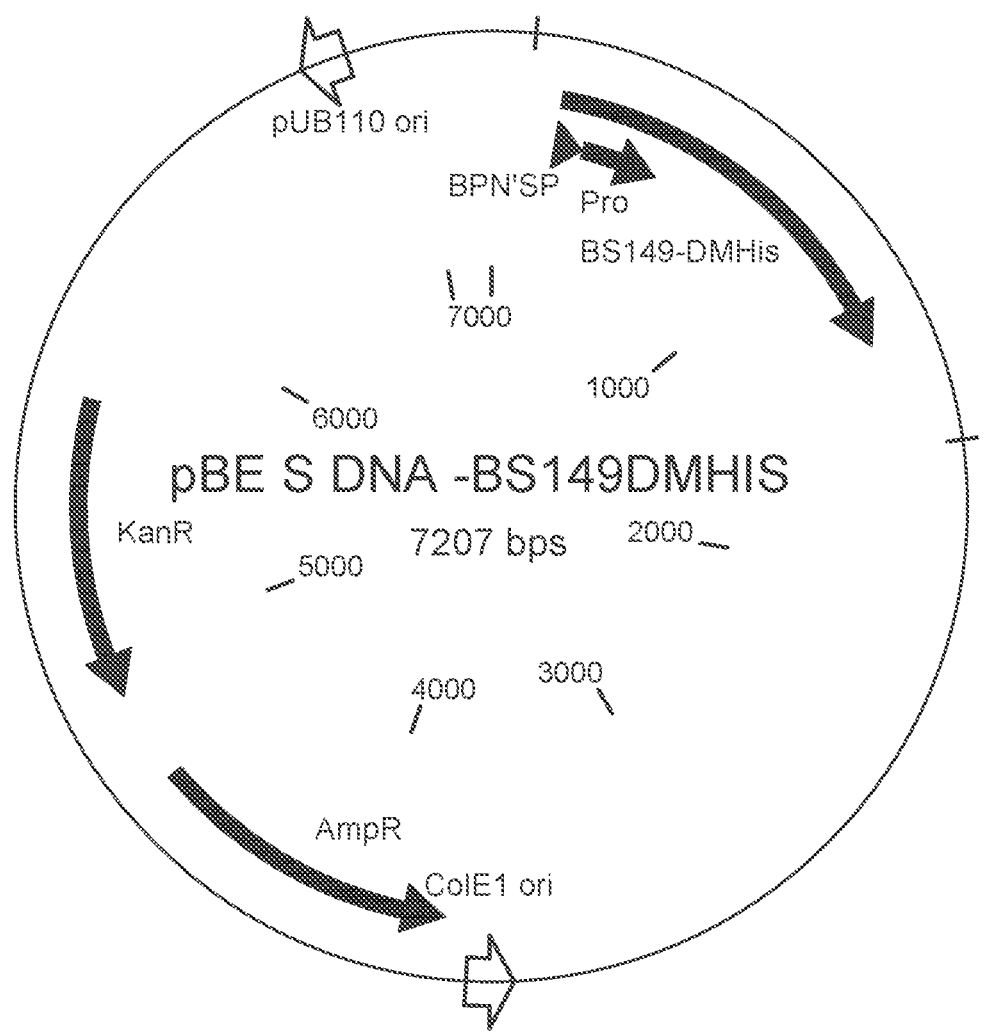
FIG. 1: *B. subtilis/E. coli* shuttle vector pBE-S with BS149-DM gene (pBES DNA-BS149-DM HIS tag).

The present invention provides a new concept that is considered to be applicable to a wide variety of serine endoproteases and their corresponding ligases/cyclases, i.e. ligases/cyclases which are variants or homologues of a serine endoprotease, comprising at least a mutation compared to the serine endoprotease at the amino acid position corresponding to a serine in a hydrolytically active site of the serine endoprotease. Serine proteases can generally be classified in EC 3.4.21. Generally, they have a catalytic triad in the order Asp, His and Ser (http://merops.sanger.ac.uk/cgi-bin/merops.cgi?id=s8).

The term "ligase" is used herein for an enzyme having catalytic activity in the coupling of two (oligo)peptide fragments by catalysing the formation of a peptide bond by coupling the C-terminus of a first oligo(peptide) fragment and the N-terminus of another (oligo)peptide fragment. The term "cyclase" is used for enzymes having catalytic activity in the cyclization of an (oligo)peptide by catalysing the formation of a peptide bond by coupling the C-terminus and the N-terminus of a single (usually linear) (oligo)peptide. The term 'coupling enzyme' is used herein to refer to a ligase or cyclase. It should be understood that various coupling enzymes disclosed herein have both ligase and cyclase activity. Likewise, the term 'coupling" may be used herein to refer to both ligation and cyclisation, as both in cyclisation and ligation a coupling is established between an N-terminal end and a C-terminal end of an (oligo)peptide.

As shown in the Examples, with a method of the invention it is possible to identify suitable (oligo)peptide fragments that can be used as starting compounds to enzymatically synthesize an (oligo)peptide of interest, by first subjecting a sample of the (oligo)peptide of interest to enzymatic hydrolysis, using a serine endoprotease that has a single modification in the amino acid sequence, compared to the ligase used for the synthesis. Further, the Examples show that it is possible to identify suitable a non-cyclic (oligo)peptide, in particular a linear (oligo)peptide, to synthesise a cyclic (oligo)peptide from by cyclization catalysed by a cyclase.

As will be described below, the ligase or cyclase may have one or more further modifications in the amino acid sequence, in particular one or more modifications whereby the ligase or cyclase has a (further) increased S/H ratio compared to the corresponding serine endoprotease. Compared to classical methods to design an enzymatic fragment condensation process for synthesizing (oligo)peptides or an enzymatic cyclisation process for synthesizing cyclic peptides, in an advantageous embodiment, the present inventions offers an important reduction in the number of experiments and the (labour) time needed to determine advantageous (oligo)peptide fragments for enzymatically synthesizing an (oligo)peptide of interest or an advantageous non-cyclic (oligo)peptide to synthesise a cyclic (oligo)peptide from. E.g., it has been found possible to determine suitable fragments for the preparation of (oligo)peptides having over 20 amino acid units in a single experiment or a couple of experiments, which—with a classical trial and error methodology—would have required more than 10 experiments. It further estimated that the time needed to design a method for enzymatically synthesizing an (oligo) peptide, in particular a relatively large (oligo)peptide may be reduced by more than a factor 4, in particular about a factor 10 or more, e.g. from more than 2 months, to less than 1 week.

Herewith a method according to the invention provides a tool that allows improved efficiency in identifying a strategy for an enzymatic process for the synthesis of an (oligo) peptide of interest. Furthermore, it facilitates the selection of an improved synthesis process, or even contributes to the development of novel synthesis processes that offer an improvement, such as higher overall yield or improved selectivity compared to a known synthesis process of a specific (oligo)peptide of interest. In a specific embodiment, a method according to the invention even allows the development of synthesis processes on an industrial scale for specific (oligo)peptides for which hitherto no satisfactory industrial scale process is known. The inventors in particular realized that a selected single difference in the amino acid sequence of the endoprotease compared to the coupling enzyme is sufficient to shift the S/H ratio to the extent that the selectivity for ligation/cyclisation on the one hand and for hydrolysis on the other hand shifts toward the hydrolysis side. Thereby a serine endoprotease, which needs to have only that single modification in amino acid sequence compared to the coupling enzyme, can be used to find advantageous (oligo)peptide fragments that can be coupled well in a fragment condensation reaction by the ligase or to find an advantageous non-cyclic (oligo)peptide for use in the synthesis of a cyclic (oligo)peptide. The inventors further realized that the ligase respectively the cyclase can have further advantageous differences in amino acid sequence compared to the serine endoprotease. If present, one or more further differences are typically at one or more amino acid positions, whereby the S/H ratio of the coupling enzyme is further increased, without unacceptably altering substrate specificity of the coupling enzyme. This will be described in further detail herein below.

The method for designing a synthesis process in accordance with the invention can be used for a broad spectrum of (oligo)peptides. The (oligo)peptide for which a synthesis process is designed in accordance with the invention or that is synthesised in accordance with the invention (i.e. the '(oligo)peptide of interest'), advantageously is a pharmaceutically active (oligo)peptide. In a further advantageous embodiment the (oligo)peptide is an intermediate compound for the synthesis of further useful molecules, e.g. biologically active molecules which can be used in pharmaceutical, food or agricultural applications.

The method allows determination of suitable fragments for synthesizing relatively short (oligo)peptides, e.g. composed of less than 8 amino acids, but offers in particular advantages for relatively long (oligo)peptides. Thus, the (oligo)peptide for which a synthesis process is designed or which is synthesized according to the invention is usually composed of at least 8 amino acid units in particular of 10 or more amino acid units, more in particular of 12 or more amino acid units, preferably of at least 15 amino acid units, more preferably of at least 20 amino acid units, at least 25 amino acid units or at least 30 amino acid units.

For the purpose of this invention, with "synthesis over hydrolysis ratio" (S/H ratio) is meant the amount of enzymatically synthesised (oligo)peptide product divided by the amount of (oligo)peptide C-terminal ester or thioester of which the ester or thioester group has been hydrolysed.

The value of the S/H ratio of an enzyme of the invention depends on various factors, for instance the nature of the substrates (the amino acid sequences of the (oligo)peptide C-terminal ester or thioester and of the (oligo)peptide nucleophile) and reaction conditions (e.g. temperature, pH, concentration of the peptide fragments, enzyme concentration).

The term "or" as used herein is defined as "and/or" unless it is specified otherwise or it follows from the context that it means 'either . . . or . . . '.

The term "a" or "an" as used herein is defined as "at least one" unless it is specified otherwise or it follows from the context that it should refer to the singular only.

When referring to a noun (e.g. a compound, an additive, etc.) in the singular, the plural is meant to be included, unless it follows from the context that it should refer to the singular only.

For the purpose of this invention, with "peptides" is meant any chain composed of two or more amino acids. Thus, peptides are generally amides at least conceptually composed of two or more amino carboxylic acid molecules (i.e. amino acids) by formation of a covalent bond from the carbonyl carbon of one to the nitrogen atom of another with formal loss of water. The term is usually applied to structures formed from alpha-amino acids. A peptide may be linear, branched or cyclic. A peptide can have a single chain composed of two or more amino acids or a peptide can have a plurality of chains. In the case a peptide is composed of two or more chains, each chain generally is composed of three or more amino acid molecules. The amino acid sequence of a peptide is referred to as the primary structure.

In an embodiment, the peptide is essentially free of a secondary structure and essentially free of a tertiary structure.

In a further embodiment, the peptide has a secondary structure. Secondary structures are generally highly regular local sub-structures, such as alpha-helices and beta-sheets (or beta-strands), by interactions between the individual amino acids and the peptide backbone.

In an embodiment, the peptide (or plurality of peptides) has a tertiary structure. Tertiary structures are generally formed by multiple interactions, among others hydrogen bonding, hydrophobic interactions, van der Waals interactions, ionic interactions and disulphide bonds. The secondary structure can also contribute to the tertiary structure. The tertiary structure provides a three-dimensional shape (which is essentially fixed in a stable environment, such as in the absence of a change in temperature and in the absence of a change in the medium wherein the peptide is present, etc.). As the skilled person knows, the tertiary structure is different from a random coil peptide chain lacking any fixed three-dimensional structure. Proteins are (oligo)peptides having a tertiary structure. A well known example of tertiary structure is the globular structure of globular proteins. In an embodiment, the protein is a protein for target delivery of a pharmaceutically active (oligo)peptide to a specific site, e.g. to a tumour or to organ tissue. Well known examples of proteins, suitable for such purpose, are immunoglobulins or parts thereof, such as an antigen-binding fragment (Fab) of an immunoglobulin. Immuglobulins coupled to a pharmaceutically active (oligo)peptide can thus be used to more efficiently deliver a pharmaceutically active (oligo)peptide to a target, e.g. tumor tissue or organ tissue, that contain an antigen for the immunoglobulin. In an embodiment, the protein is a protein suitable to increase the half-life of an (oligo)peptide in a living organism, in particular the blood plasma half-life. Albumins are examples of proteins that can be coupled to an (oligo)peptide to increase the half-life.

Disulphide bonds (disulphide bridges) are typically bonds between two cysteine units (formed by oxidation). Thus, two amino acids in a same peptide chain (amino acid sequence) can be covalently bound, also if they are not adjacent amino acids in the amino acid sequence. Also, a disulphide bond between a first cysteine of a first peptide chain and a second cysteine of a second peptide chain, which may have the same or a different amino acid sequence, can be formed to form a peptide. Such peptide comprises more than one peptide chain. An example of a peptide composed of more than one peptide chain, wherein the different chains are bound via a disulphide bond is insulin. Other bonds to join different peptide chains are generally known in the art.

In an embodiment, the (oligo)peptide essentially consists of amino acid units. In a further embodiment, the (oligo) peptide essentially consists of amino acid units and protective groups. In an embodiment, the peptide is a conjugate of a peptide chain of two or more amino acids and another molecule, in particular a carbohydrate or a lipid. These peptides are called glycopeptides and lipopeptides respectively. In a further embodiment, the peptide conjugate is a conjugate of two or more amino acids and an imaging agent, such as a fluorescent, phosphorescent, chromogenic or radioactive group. The peptide conjugate may also contain a chelation agent or toxin.

Typically, a peptide—which term includes oligopeptides, proteins and peptide conjugates—comprises up to about 35 000 amino acid units, in particular 3-20 000 amino acid units, more in particular 4-5 000 amino acid units, preferably 5-1000 amino acid units. In a specifically preferred embodiment the peptide comprises 500 amino acid units or less, in particular 200 or less, more in particular 100 or less. In a specifically preferred embodiment, the peptide comprises at least 10 amino acid units, more specifically at least 15 amino acids, at least 25 amino acid units, at least 30 amino acid units, or at least 40 amino acids.

With "oligopeptides" is meant within the context of the invention, a peptide composed of 2-200 amino acid units, in particular composed of 5-100 amino acid units, more in particular composed of 10-50 amino acid units.

The term "(oligo)peptide" is used herein as a short-hand for the phrase "peptides, in particular oligopeptides".

The (oligo)peptide for which a synthesis process is designed or that is synthesized in accordance with the invention may be linear, branched or cyclic. Good results have been achieved with a linear or cyclic (oligo)peptide. Further good results have been achieved in the synthesis of a peptide having more than 200 amino acid units, e.g. of about 800 amino acid units. Thus, the peptide can have at least 250 amino acid units or at least 400 amino acid units. Further, good results have been achieved with the coupling of a peptide fragment to a protein, such as insulin, whilst maintaining a secondary and tertiary protein structure. The protein can have 200 or less amino acid units or can have more than 201 amino acid units.

In a process of synthesizing the non-cyclic (oligo)peptides, these are synthesized from a first (oligo)peptide and a second (oligo)peptide, which are both smaller than the (oligo)peptide that is synthesized. The first (oligo)peptide is an (oligo)peptide C-terminal ester or thioester and the second (oligo)peptide comprises an N-terminally unprotected amine. The (oligo)peptide C-terminal ester or thioester is also referred to as an (oligo)peptide acyl donor. The second (oligo)peptide is also referred to as an (oligo)peptide nucleophile. These (oligo)peptides from which the synthesised (oligo)peptide is formed are referred to herein as '(oligo) peptide fragments'. These (oligo)peptide fragments can on their turn be synthesized enzymatically from a smaller (oligo)peptide acyl donor and an (oligo)peptide nucleophile or by regular chemical solution or solid phase peptide synthesis, known by the person skilled in the art.

For the purpose of this invention, with "peptide bond" is meant the amide bond between (i) either the alpha-amino terminus of one alpha-amino acid or the beta-amino acid terminus of one beta-amino acid and (ii) either the alpha-carboxyl terminus of one other alpha-amino acid or the beta-carboxyl terminus of one other beta-amino acid. Preferably, the peptide bond is between the alpha-amino terminus of one amino acid and the alpha-carboxyl terminus of another amino acid.

For the purpose of this invention, with "cyclic peptide" is meant an (oligo)peptide chain wherein the alpha-amino terminus and the alpha-carboxyl terminus of a branched or linear (oligo)peptide are linked via a peptide bond, thereby forming a ring structure of at least 12 amino acid units. The cyclic peptide is in particular composed of 12-200 amino acid units, more in particular composed of 12-100 amino acid units and preferably composed of 12-50 amino acid units.

For the purpose of this invention, with "condensation" is meant the formation of a new peptide bond between the C-terminal carboxylic function of an (oligo)peptide with the N-terminal amine function of another (oligo)peptide or of the same (oligo)peptide.

In the context of this application, the term "about" means in particular a deviation of 10% or less from the given value, more in particular 5% or less, even more in particular 3% or less.

As defined by Schechter and Berger, the active site residues in proteases, including subtilisins, are composed of contiguous pockets termed subsites. Each subsite pocket binds to a corresponding residue in the peptide substrate sequence, referred to here as the sequence position. According to this definition, amino acid residues in the substrate sequence are consecutively numbered outward from the cleavage sites as . . . -P4-P3-P2-P1-P1'-P2'-P3'-P4'- . . . (the scissile bond is located between the P1 and P1' positions), while the subsites in the active site are correspondingly labelled as . . . -S4-S3-S2-S1-S1'-S2'-S3'-S4'-. (Schechter and Berger, Biochem Biophys Res Commun. 1967 Apr. 20; 27(2):157-62.)).

For the purpose of this invention, with "S1, S2, S3 and S4 pocket" is meant the amino acids of a protease which interact with the amino acids of an (oligo)peptide acyl donor. The C-terminal amino acid ($1^{st}$ amino acid; P1) of the acyl donor (oligo)peptide interacts with the amino acids in the S1 pocket of the protease. The penultimate amino acid ($2^{nd}$ amino acid; P2) of the acyl donor (oligo)peptide interacts with the amino acids in the S2 pocket of the protease, the third amino acid (P3) with the S3 and the fourth amino acid (P4) with the S4 pocket. The S1-S4 binding pockets of a protease are defined by several amino acids which can be distant in the primary structure of the protease, but are close in the three dimensional space. For the purpose of this invention, with S1' and S2' pockets are meant the amino acids of a protease which interact with the N-terminal amino acids of an (oligo)peptide nucleophile. The N-terminal amino acid of the (oligo)peptide nucleophile interacts with the amino acids in the S1' pocket of the protease. The N-terminal penultimate amino acid of the (oligo)peptide nucleophile interacts with the amino acids in the S2' pocket of the protease. The S1' and S2' binding pockets of a protease are defined by several amino acids which can be distant in the primary structure of the protease, but are close in the three dimensional space.

For the purpose of this invention, with "denaturating agent" is meant an additive which potentially can destroy the three dimensional structure of a protease, and thus, can potentially inactivate the protease.

In the context of the invention with "amino acid side-chain" is meant any proteinogenic or non-proteinogenic amino acid side-chain.

Proteinogenic amino acids are the amino acids that are encoded by the genetic code. Proteinogenic amino acids include: alanine (Ala), valine (Val), leucine (Leu), isoleucine (Ile), serine (Ser), threonine (Thr), methionine (Met), cysteine (Cys), asparagine (Asn), glutamine (Gln), tyrosine (Tyr), tryptophan (Trp), glycine (Gly), aspartic acid (Asp), glutamic acid (Glu), histidine (His), lysine (Lys), arginine (Arg), proline (Pro) and phenylalanine (Phe). Selenocysteine (Sec, U) is an amino acid, of which the structure corresponds to cysteine, with the proviso that it contains a selenium instead of a sulphur atom.

Non-proteinogenic amino acids may in particular be selected amongst D-amino acids, L- or D-phenylglycine, DOPA (3,4-dihydroxy-L-phenylalanine), beta-amino acids, 4-fluoro-phenylalanine, or $C^{\alpha}$-alkylated amino acids.

The term "mutated" or "mutation" as used herein regarding proteins or polypeptides—in particular enzymes—means that at least one amino acid in the wild-type or naturally occurring protein or polypeptide sequence has been replaced with a different amino acid, inserted into, appended to, or deleted from the sequence via mutagenesis of nucleic acids encoding these amino acids. Mutagenesis is a well-known method in the art, and includes, for example, site-directed mutagenesis by means of PCR or via oligonucleotide-mediated mutagenesis as described in Sambrook et al., Molecular Cloning-A Laboratory Manual, 2nd ed., Vol. 1-3 (1989). The term "mutated" or "mutation" as used herein regarding genes means that at least one nucleotide in the nucleic acid sequence of that gene or a regulatory sequence thereof, has been replaced with a different nucleotide, has been inserted into, has been appended to, or has been deleted from the sequence via mutagenesis, resulting in the transcription of a protein sequence with a qualitatively of quantitatively altered function or resulting in the knock-out of that gene.

In the present specification, a shorthand for denoting amino acid substitutions employs the single letter amino acid code of the amino acid that is substituted, followed by the number designating where in the protein amino acid sequence the substitution is made. This number is the amino acid position of the wild-type amino acid sequence (generally subtilisin BPN' unless specified otherwise). Thus for the mutated amino acid sequence it is the amino acid position corresponding to the position with that number in the wild type enzyme. Due to one or more other mutations at a lower position (additions, insertions, deletions, etc.) the actual position does not need to be the same. The skilled person will be able to determine the corresponding positions using a generally known alignment technique, such as NEEDLE. The number is followed by the single letter code of the amino acid that replaces the wild-type amino acid therein. For example, G166S denotes the substitution of glycine at the position corresponding to position 166 to serine. X is used to indicate any other proteinogenic amino acid than the amino acid to be substituted. For example, G166X denotes the substitution of glycine 166 to any other proteinogenic amino acid.

When referring to a compound of which stereoisomers exist, the compound may be any of such stereoisomers or a mixture thereof. Thus, when referred to, e.g., an amino acid of which enantiomers exist, the amino acid may be the L-enantiomer, the D-enantiomer or a mixture thereof. In case a natural stereoisomer exists, the compound is preferably a natural stereoisomer.

The term 'pH' is used herein for the apparent pH, i.e. the pH as measured with a standard, calibrated pH electrode.

When an enzyme is mentioned with reference to an enzyme class (EC) between brackets, the enzyme class is a class wherein the enzyme is classified or may be classified, on the basis of the Enzyme Nomenclature provided by the Nomenclature Committee of the International Union of Biochemistry and Molecular Biology (NC-IUBMB), which nomenclature may be found at http://www.chem.qmul.ac.uk/iubmb/enzyme/. Other suitable enzymes that have not (yet) been classified in a specified class but may be classified as such, are meant to be included.

Homologues typically have an intended function in common with the polynucleotide respectively polypeptide (enzyme) of which it is a homologue, such as encoding the same peptide respectively being capable of catalyzing the same reaction. The term homologue is also meant to include nucleic acid sequences (polynucleotide sequences) which differ from another nucleic acid sequence due to the degeneracy of the genetic code and encode the same polypeptide sequence.

Amino acid or nucleotide sequences are said to be homologous when exhibiting a certain level of similarity. Two sequences being homologous indicate a common evolutionary origin. Whether two homologous sequences are closely related or more distantly related is indicated by "percent identity" or "percent similarity", which is high or low respectively.

The terms "homology", "percent homology", "percent identity" or "percent similarity" are used interchangeably herein. For the purpose of this invention, it is defined here that in order to determine the percent identity of two amino acid sequences or of two nucleic acid sequences, the complete sequences are aligned for optimal comparison purposes. In order to optimize the alignment between the two sequences gaps may be introduced in any of the two sequences that are compared. Such alignment is carried out over the full length of the sequences being compared. Alternatively, the alignment may be carried out over a shorter length, for example over about 20, about 50, about 100 or more nucleic acids or amino acids. The percentage identity is the percentage of identical matches between the two sequences over the reported aligned region.

A comparison of sequences and determination of percent identity between two sequences can be accomplished using a mathematical algorithm. The skilled person will be aware of the fact that several different computer programs are available to align two sequences and determine the homology between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent identity between two amino acid sequences can be determined using the Needleman and Wunsch algorithm for the alignment of two sequences. (Needleman, S. B. and Wunsch, C. D. (1970) J. Mol. Biol. 48, 443-453). The algorithm aligns amino acid sequences as well as nucleotide sequences. The Needleman-Wunsch algorithm has been implemented in the computer program NEEDLE. For the purpose of this invention the NEEDLE program from the EMBOSS package was used (version 2.8.0 or higher, *EMBOSS: The European Molecular Biology Open Software Suite* (2000) Rice, P. Longden, I. and Bleasby, A. Trends in Genetics 16, (6) pp 276-277, http://emboss.bioinformatics.nl/). For protein sequences, EBLOSUM62 is used for the substitution matrix. For nucleotide sequences, EDNAFULL is used. Other matrices can be specified. The optional parameters used for alignment of amino acid sequences are a gap-open penalty of 10 and a gap extension penalty of 0.5. The skilled person will appreciate that all these different parameters will yield slightly different results but that the overall percentage identity of two sequences is not significantly altered when using different algorithms.

The homology or identity between the two aligned sequences is calculated as follows: the number of corresponding positions in the alignment showing an identical amino acid in both sequences divided by the total length of the alignment after subtraction of the total number of gaps in the alignment. The identity defined as herein can be obtained from NEEDLE by using the NOBRIEF option and is labelled in the output of the program as "longest-identity". For purposes of the invention the level of identity (homology) between two sequences (amino acid or nucleotide) is calculated according to the definition of "longest-identity" as can be carried out by using the program NEEDLE.

The polypeptide sequences representing an enzyme of the present invention, can further be used as a "query sequence" to perform a search against sequence databases, for example to identify other family members or related sequences. Such searches can be performed using the BLAST programs. Software for performing BLAST analyses is publicly available through the National Center for Biotechnology Information (http://www.ncbi.nlm.nih.gov). BLASTP is used for amino acid sequences and BLASTN for nucleotide sequences. The BLAST program uses as defaults:

Cost to open gap: default=5 for nucleotides/11 for proteins

Cost to extend gap: default=2 for nucleotides/1 for proteins

Penalty for nucleotide mismatch: default=−3

Reward for nucleotide match: default=1

Expect value: default=10

Wordsize: default=11 for nucleotides/28 for megablast/3 for proteins

Furthermore the degree of local identity (homology) between the amino acid sequence query or nucleic acid sequence query and the retrieved homologous sequences is determined by the BLAST program. However only those sequence segments are compared that give a match above a certain threshold. Accordingly the program calculates the identity only for these matching segments. Therefore the identity calculated in this way is referred to as local identity.

The term "homologue" is used herein in particular for polypeptides (enzymes) having a sequence identity of at least 50%, preferably at least 60%, more preferably at least 70%, at least 80%, at least 90%, at least 95%, at least 96%, at least 97%, at least 98% or at least 99% with the polypeptide (enzyme) with which the homologue peptide is compared. Evidently, the sequence identity will be less than 100%. The percentage of sequence identity will depend on the number of mutations and the length of the polypeptide with which the homologue is prepared. In particular, for a subtilisin BPN' variant, the number of mutations for the enzymes in the present invention will typically be at least 11, of which at least nine mutations are deletions and at least two mutations are replacements for another amino acid. In 'longest identity' alignment the deletions are not taken into account. This means that the sequence identity of an enzyme of the invention compared to subtilisin BPN' generally is 99.25% (two replacements in a polypeptide with 266 amino acids) or less. Preferably, the sequence identity of an enzyme of the invention compared to SEQUENCE ID NO 2, is 98% or less, more preferably 96% or less, in particular 94% or less, more in particular 92% or less, or 90% or less.

"Expression" refers to the transcription of a gene into structural RNA (rRNA, tRNA) or messenger RNA (mRNA) with subsequent translation into a protein.

As used herein, "heterologous" in reference to a nucleic acid or protein is a nucleic acid or protein that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

The term "heterologous expression" refers to the expression of heterologous nucleic acids in a host cell. The expression of heterologous proteins in suitable host cell systems are well known to those of skill in the art. The skilled person will be able to provide suitable host cells for producing an enzyme of the invention from various organisms without undue burden based upon common general knowledge and the information disclosed herein.

As used herein "promoter" is a DNA sequence that directs the transcription of a (structural) gene. Typically, a promoter is located in the 5' region of a gene, proximal to the transcriptional start site of a (structural) gene. Promoter sequences may be constitutive, inducible or repressible. If a promoter is an inducible promoter, then the rate of transcription increases in response to an inducing agent.

The term "vector" as used herein, includes reference to an autosomal expression vector and to an integration vector used for integration into the chromosome.

The term "expression vector" refers to a DNA molecule, linear or circular, that comprises a segment encoding a polypeptide (enzyme) of interest under the control of (i.e. operably linked to) additional nucleic acid segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both.

"Plasmid" refers to autonomously replicating extrachromosomal DNA which is not integrated into a microorganism's genome and is usually circular in nature.

An "integration vector" refers to a DNA molecule, linear or circular, that can be incorporated in a microorganism's genome and provides for stable inheritance of a gene encoding a polypeptide of interest. The integration vector generally comprises one or more segments comprising a gene sequence encoding a polypeptide of interest under the control of (i.e. operably linked to) additional nucleic acid segments that provide for its transcription. Such additional segments may include promoter and terminator sequences, and one or more segments that drive the incorporation of the gene of interest into the genome of the target cell, usually by the process of homologous recombination. Typically, the integration vector will be one which can be transferred into the target cell, but which has a replicon which is non-functional in that organism. Integration of the segment comprising the gene of interest may be selected if an appropriate marker is included within that segment.

As used herein, the term "operably linked" refers to a juxtaposition wherein the components so described are in a relationship permitting them to function in their intended manner. A control sequence "operably linked" to another control sequence and/or to a coding sequence is ligated in such a way that transcription and/or expression of the coding sequence is achieved under conditions compatible with the control sequence. Generally, operably linked means that the nucleic acid sequences being linked are contiguous and, where necessary to join two protein coding regions, contiguous and in the same reading frame.

By "host cell" is meant a cell which contains a vector and supports the replication and/or expression of the vector. Host cells may be prokaryotic cells such as bacterial cells, or eukaryotic cells such as yeast, plant, insect, amphibian, or mammalian cells.

"Transformation" and "transforming", as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host cell genome.

For the purpose of clarity and a concise description features are described herein as part of the same or separate embodiments, however, it will be appreciated that the scope of the invention may include embodiments having combinations of all or some of the features described.

Identifying two or more (oligo)peptide fragments of an (oligo)peptide in a method of the invention is usually carried out as part of designing a synthesis process for enzymatically synthesizing the (oligo)peptide by enzymatic condensation of the two or more (oligo)peptide fragments using the ligase or the cyclization of a non-cyclic (oligo)peptide using the cyclase.

The method of designing the enzymatic synthesis process of an (oligo)peptide comprises an enzymatic hydrolysis of a sample of the full (oligo)peptide to be synthesised or a segment of the oligopeptide to be synthesised. As used herein, a segment of an (oligo)peptide is an (oligo)peptide that is shorter than the oligo(peptide) of which it is a segment and having an amino acid sequence that is also present in the amino acid sequence of which it is a segment. Thus, peptides that are obtainable by hydrolysis of a larger peptide are typically segments of that larger peptide. E.g. peptides with one of the sequences ABCDE, CDFGHI or KLMN, each are segments of the peptide ABCDEFGHIKLMN.

The 'sample (oligo)peptide' (which may be cyclic or non-cyclic) that is subjected to enzymatic hydrolysis catalysed by the serine endoprotease can be obtained based on technology that is known per se. E.g., if it is a natural (oligo)peptide, it may be isolated from a natural source comprising the (oligo)peptide or it may be produced by a transgenic host cell capable of producing the (oligo)peptide. If the (oligo)peptide is commercially available, it can be purchased. Alternatively, the sample (oligo)peptide may be synthesized using a chemical or enzymatic synthesis, based on technology known per se. The sample (oligo)peptide to be subjected to hydrolysis is usually free of protective side-groups and/or protective end-groups. The presence of protective side-groups is usually undesired because it may prevent a potential cleavage site in the (oligo)peptide from being hydrolysed to a significant extent.

The (oligo)peptide for which an enzymatic synthesis process is designed can be a peptide only having a primary structure. However, it is also possible to design an enzymatic synthesis process for an (oligo)peptide further having a secondary and/or tertiary structure. One may use a sample of such an (oligo)peptide in a form wherein it still has a secondary/tertiary structure. However, it is also possible to partially or fully remove such structures ("unfold" the (oligo)peptide), prior to subjecting the (oligo)peptide to hydrolysis in the presence of the serine endoprotease. This is in particular advantageous if the (oligo)peptide of interest, contains a secondary or tertiary structure whereby (potential) hydrolytic positions are inaccessible for the serine endoprotease due to steric hindrance. To make these positions accessible, secondary of tertiary disrupting agents can be added, e.g. urea or guanidinium hydrochloride. Other disrupting agents are known to the person skilled in the art. Prior to or during the hydrolysis, disulphide bridges can be reduced using reductive agents, e.g. tris(2-carboxyethyl) phosphine (TCEP), dithiotreitol (DTT) or ethanedithiol. Other disulphide reducing agents are known to the person skilled in the art.

In an embodiment, a method for designing a synthesis process for synthesizing an (oligo)peptide of interest according to the invention, comprises
  selecting a serine endoprotease;
  subjecting a sample of the (oligo)peptide or segment of the (oligo)peptide of interest (i.e. a smaller (oligo) peptide having an amino acid sequence that is also present in the amino acid sequence of the (oligo) peptide of interest) to enzymatic hydrolysis catalysed by the serine endoprotease;
  determining the amino acid sequence of the (oligo)peptide fragments obtained by the enzymatic hydrolysis;
  selecting a ligase which ligase is a variant of a serine endoprotease, the ligase having at least a mutation of a serine in a hydrolytically active site of the endoprotease into cystein or selenocystein.

In a further embodiment, a method for designing a synthesis process according to the invention, comprises
  selecting a (potential) ligase for catalysing the coupling of (yet to be determined) (oligo)peptide fragments of an (oligo)peptide to be synthesised, then
  selecting a corresponding serine endoprotease; the endoprotease generally only needing to be different from the ligase in that the serine endoprotease contains the serine in the hydrolytically active site whereas the ligase contains a cystein or selenocystein in the corresponding active site of the ligase.
  subjecting a sample of the (oligo)peptide or a segment of the (oligo)peptide to enzymatic hydrolysis catalysed by the serine endoprotease; and
  determining the amino acid sequence of the (oligo)peptide fragments obtained by the enzymatic hydrolysis.

Designing a process to enzymatically synthesise a cyclic (oligo)peptide can be done in an essentially analogous way, with the distinction that the hydrolytic reaction does not necessarily result in the generation of (oligo)peptide fragments, as there only needs to be a single cleavage of a peptide bond to obtain a single non-cyclic (oligo)peptide that can be identified as the non-cyclic (oligo)peptide from which the cyclic (oligo)peptide can be synthesized. Further, the enzyme catalysing the peptide bond formation between both the C-terminus and the N-terminus of the non-cyclic (oligo)peptide should have cyclase activity.

Accordingly, in an embodiment, a method for designing a synthesis process for synthesizing a cyclic (oligo)peptide of interest according to the invention, comprises
  selecting a serine endoprotease;
  subjecting:
    a sample of the cyclic (oligo)peptide, to enzymatic hydrolysis catalysed by the serine endoprotease, thereby obtaining a non-cyclic (oligo)peptide having the same number of amino acid units as the cyclic (oligo)peptide, and optionally (oligo)peptide fragments, or
    a sample of a segment of the cyclic (oligo)peptide, which segment is a non-cyclic, preferably linear (oligo)peptide, thereby obtaining two or more (oligo) peptide fragments;
  determining the amino acid sequence of the non-cyclic (oligo)peptide respectively the two or more (oligo) peptide fragments obtained by the enzymatic hydrolysis;
  selecting a cyclase which cyclase is a variant of a serine endoprotease, the cyclase having at least a mutation of a serine in a hydrolytically active site of the serine endoprotease into cystein or selenocystein.

In a further embodiment of a method for designing a synthesis process of a cyclic (oligo)peptide according to the invention, comprises
  selecting a (potential) cyclase for catalysing the cyclisation of the non-cyclic (oligo)peptide to form the cyclic (oligo)peptide of interest, then
  selecting a corresponding serine endoprotease; the endoprotease generally only needing to be different from the cyclase in that the serine endoprotease contains the serine in the hydrolytically active site instead of a cystein or selenocystein present in the corresponding active site of the cyclase.
  subjecting:
    a sample of the cyclic (oligo)peptide, to enzymatic hydrolysis catalysed by the serine endoprotease, thereby obtaining a non-cyclic (oligo)peptide having the same number of amino acid units as the cyclic (oligo)peptide, and optionally (oligo)peptide fragments, or
    a sample of a segment of the cyclic (oligo)peptide, which segment is a non-cyclic, preferably linear (oligo)peptide, thereby obtaining two or more (oligo) peptide fragments;
  determining the amino acid sequence of the non-cyclic (oligo)peptide respectively the two or more (oligo) peptide fragments obtained by the enzymatic hydrolysis;

In an embodiment, a method according to the invention for designing an enzymatic process for the synthesis of a cyclic (oligo)peptide also comprises designing an enzymatic process for the synthesis of the non-cyclic (oligo)peptide from which the cyclic (oligo)peptide is prepared by cyclisation. Dependent on the specific cyclic (oligo)peptide and the serine endoprotease used, one may identify suitable fragments for enzymatically synthesising the non-cyclic (oligo)peptide from the hydrolysate of the sample of the cyclic (oligo)peptide or segment thereof or one may carry out a separate method for designing the enzymatic synthesis of the non-cyclic (oligo)peptide, comprising the hydrolysis of said non-cyclic (oligo)peptide or segment thereof, Likewise, a method for designing an enzymatic synthesis process can be applied to (oligo)peptide fragments for use in the synthesis of a larger non-cyclic (oligo)peptide.

Typically, in a method of the invention wherein an enzymatic peptide synthesis process is designed, a serine endoprotease is used that has a lower S/H ratio than the corresponding coupling enzyme, under suitable reaction conditions for the coupling enzyme to catalyse peptide bond formation. Usually, the S/H ratio of the ligase respectively cyclase divided by the S/H ratio of the serine endoprotease is more than 10, preferably at least 100, more preferably at least 500. From a synthesis process point of view, there is no desirable upper limit for this ratio. In practice it may be up to 1000, up to 10 000, up to 50 000, up to 100 000, or even higher.

The reaction conditions for the hydrolysis are preferably the same as or similar to the reaction conditions under which the ligase respectively cyclase has substantial ligase activity respectively cyclase activity (conditions under which it can be used in the synthesis process). Preferred conditions depend on the specific enzyme. For Subtilisin BPN' variants or homologues thereof aqueous conditions are preferred. For enzymes that have been reported to have ligase activity under non-aqueous conditions, a reaction in organic solvent with a trace of water are particularly suitable.

Preferred ligases and endoproteases and reaction conditions will be discussed below in more detail.

In a method of the invention, it is preferred that the ligase and the endoprotease preferably have about the same substrate specificity or that the ligase has a higher substrate specificity. A single substitution in a hydrolytically active site compared to the endoprotease with a suitable amino acid is sufficient to increase the S/H ratio. In particular, it is preferred that, apart from the mutation of the serine compared to the serine endoprotease the ligase is free of any further mutations—compared to the serine endoprotease—in the S1, S2, S3, S4, S1' and S2' pockets of the ligase.

The endoprotease and the ligase may have further differences from each other in parts of the endoprotease respectively ligase. In particular, it is preferred that the ligase contains one or more additional substitutions compared to the serine endoprotease whereby the S/H ratio is improved.

In a method of the invention use may be made of a single serine endoprotease, or a series of experiments are carried out wherein in different reaction vessels samples of the (oligo)peptide are contacted with different serine endoproteases under hydrolytic conditions. To this purpose an array of serine endoprotease containing reaction vessels may be used.

The hydrolysis reaction is usually carried out for as sufficient duration to obtain a quantifiable amount of at least two (oligo)peptide fragments, or—in a method for designing a process for the enzymatic synthesis of a cyclic (oligo) peptide, for a sufficient duration to obtain a quantifiable amount of the non-cyclic peptide. The duration can empirically be determined.

In a preferred embodiment of a method according to the invention the sample of the (oligo)peptide is contacted with the endoprotease under hydrolytic conditions for a duration wherein 10 to 95% of the (oligo)peptide has been hydrolysed into two or more (oligo)peptide fragments respectively wherein 10 to 95% of the cyclic (oligo)peptide is hydrolysed into at least one non-cyclic (oligo)peptide, more preferably 20 to 90% of the (oligo)peptide has been hydrolysed into two or more (oligo)peptide fragments respectively 20 to 90% of the cyclic (oligo)peptide is hydrolysed into at least one non-cyclic (oligo)peptide. An intermediate level of hydrolysis is advantageous, because this may allow or at least facilitate the identification of more suitable (oligo)peptide fragments for use in enzymatic coupling to synthesise an (oligo)peptide of interest or more suitable non-cyclic (oligo)peptides for use in an enzymatic cyclization reaction to synthesise a cyclic (oligo)peptide of interest will be more prominently visible upon analysis.

E.g. in case the serine endoprotease hydrolyses more than one peptide bond, but has different activities towards different peptide bonds, initially the fragments resulting from the cleavage of the peptide bond towards which the endoprotease has the highest activity, will be dominant in the analysis results, and further hydrolysate products formed at a lower rate might be overlooked. These hydrolysate products may also be interesting to synthesise the (oligo)peptide of interest from. On the other hand, after a sufficient degree of hydrolysis, the additional information that may be gained from further hydrolysis may be limited, and at least in some embodiments at some point so many (small) fragments may be formed that identifying the optimal fragments can become cumbersome. The skilled person will be able to determine a sufficient duration based on the present disclosure, common general knowledge and optionally a limited amount of testing.

E.g., it is possible to take samples of the reaction mixture in which the sample (oligo)peptide is subjected to hydrolysis, continuously or intermittently and to determine the length of the (oligo)peptides, and optionally also their sequence, in the reaction mixture in time. Thus one can ensure that fragments (or non-cyclic (oligo)peptides for the synthesis of a cyclic (oligo)peptide) are identified before the (oligo)peptide has fully hydrolysed into free amino acids. This information can be used to identify initially formed fragments and later formed fragments, if any, as the hydrolysis time proceeds. Thus, one may determine a suitable single enzymatic coupling step synthesis strategy or a suitable multi-step enzymatic coupling strategy. E.g., if (at an early stage of) the hydrolysis of a sample (oligo)peptide having x amino acid units is (predominantly) hydrolysed into a first fragment (A) having y amino acid units, containing the N-terminal part of the (oligo)peptide and a second fragment (B) having x-y amino acid units, containing the C-terminal part of the (oligo)peptide, then this first fragment and second fragment would be suitable fragments to use in the synthesis process of the (oligo)peptide. These fragments may be synthesized themselves by a method known per se, e.g. by a known chemical or enzymatic method or one or both of these fragments may be subjected to further hydrolysis with the same or another endoprotease in a method of the invention, e.g. in the case of using the same endoprotease by continuing the hydrolysis process and monitoring the hydrolysis. Thus it may e.g. be found that the first fragment (A) is hydrolysed into a third fragment (C) having length z, containing the N-terminal side of the (oligo)peptide and a fourth fragment (D) having length y-z. Thus, in this example the (oligo)peptide would conceptually be construed of two fragments in the order A-B or three fragments in the order C-D-B. On the basis of this, one can further design the synthesis process as a two-step coupling process wherein first D and B are coupled to form D-B, which is then coupled with C to form C-D-B, i.e. the (oligo)peptide.

Usually it is practical to use a sample of the whole (oligo)peptide of interest for the hydrolysis test with the endoprotease(s). However, in various embodiments it is also possible to use only a segment of the (oligo)peptide, i.e. a part lacking one or more amino acid units at one or both of the extremities of the (oligo)peptide. At least as long as there is still a peptide bond that is cleaved by the endoprotease(s) in the segment of the (oligo)peptide of interest, carrying out the method with a segment of the oligeptide is still useful to identify a suitable coupling site, and thus allows identification of suitable fragments for the synthesis process. Preferably, the segment of the (oligo)peptide has at least 10% of the number of amino acids of the full (oligo)peptide, more preferably at least 20%, in particular at least 50% of the full (oligo)peptide.

The determination of the amino acid sequence of the (oligo)peptide fragments obtained by the hydrolysis of an (oligo)peptide or of an (oligo)peptide obtained by hydrolysing a cyclic (oligo)peptide can be carried out using analytical methodology generally known in the art. Preferably the hydrolysate obtained by hydrolysis of a sample of the (oligo)peptide is analysed by high performance liquid chromatography (HPLC) coupled with mass spectrometry (MS), the combination being called LC-MS. Using LC-MS, the different (oligo)peptide fragments, formed by enzymatic hydrolysis, are separated by amongst others polarity and their exact mass is determined. Knowing the primary amino acid sequence of the starting (oligo)peptide, the fragments and thus cleavage positions, are easily determined. The LC-MS analysis is not always sufficient when a cyclic (oligo)peptide is hydrolysed (different cleavage positions result in identical mass) or when multiple fragments with the same mass can be formed. In a preferred embodiment, the exact amino acid sequences of these fragments are determined by MS-MS.

With the knowledge of the amino acid sequence of the (oligo)peptide (fragments) the skilled person can determine (the) suitable coupling site(s) to synthesise the (oligo)peptide for which the synthesis process is designed, and learns which (oligo)peptide (fragments) to use for the synthesis process. The (oligo)peptide (fragments) to be used for the synthesis process can be obtained in a manner known per se or a method for designing a synthesis process according to the invention can be used.

The synthesis process of the invention advantageously is a kinetic process, catalysed by the ligase or cyclase.

Preferably, the process for synthesizing an (oligo)peptide from two or more peptide fragments comprises an enzymatic fragment condensation wherein a first of the fragments has a C-terminus that is esterified or thioesterified and a second of the fragments is an (oligo)peptide nucleophile having an N-terminally unprotected amine. Said fragments are enzymatically coupled at said C-terminus of the first fragment and said N-terminally unprotected amine of the second fragment Preferably, the process for synthesizing a cyclic (oligo) peptide comprises the cyclisation of a non-cyclic (oligo) peptide C-terminal ester or thioester having an N-terminally unprotected amine, wherein a peptide bond is formed between the C-terminal end and N-terminal end, catalysed by the cyclase.

As a further part of designing the synthesis process, it is preferred to select which other potentially reactive groups (besides the C-terminus of the first fragment and the N-terminus of the second fragment that are to be coupled respectively the C-terminus and N-terminus of the non-cyclic peptide that is cyclised) are to be protected and which not. In an embodiment of the process for synthesizing an (oligo) peptide from two or more peptide fragments, the N-terminus of the (oligo)peptide C-terminal ester or thioester and/or one or more side-chain functionalities of the (oligo)peptide C-terminal ester or thioester are selected to be provided with a protective group. In a further embodiment, the C-terminus of the (oligo)peptide nucleophile is provided with a protective group and/or one or more side-chain functionalities of the (oligo)peptide nucleophile are provided with a protective group. In a process for synthesizing a cyclic (oligo)peptide, the non-cyclic (oligo)peptide ester or thioester may have one or more side-chain functionalities of the (oligo)peptide C-terminal ester or thioester that are provided with a protective group.

Conditions under which to protect certain functionalities with the protective groups can be selected based on common general knowledge in combination with the information disclosed herein, the documents cited herein and optionally a limited amount of routine testing.

Typically, the (oligo)peptide C-terminal ester or thioester is an activated (thio)ester, i.e. it contains a carboxy ester or carboxy thioester group that can take part in the enzymatic coupling reaction. In principle, any (substituted or unsubstituted) alkyl or (substituted or unsubstituted) aryl (thio) ester can be used. Typical examples of (thio)esters which can take part in the enzymatic coupling reaction are methyl-, ethyl-, propyl-, isopropyl-, phenyl-, benzyl-, 2,2,2-trichloroethyl-, 2,2,2-trifluoroethyl-, cyanomethyl- and carboxyamidomethyl-(thio)esters.

Particularly good results have been obtained with carboxyamidomethyl-type esters represented by the formula peptide-(C=O)—O—CX$_1$X$_2$-C(=O)N—R$_1$R$_2$. Herein, each X$_1$ and X$_2$ independently represents a hydrogen atom or an alkyl group. Good results have been achieved when both X$_1$ and X$_2$ are a hydrogen atom (peptide-(C=O)—O—CH$_2$-C(=O)N—R$_1$R$_2$). Herein R$_1$ represents a hydrogen atom or an alkyl group and R$_2$ represents a hydrogen atom or an alkyl group or an amino acid or a peptide residue with a C-terminal carboxyamide or carboxylic acid functionality, optionally protected on the side-chain functionality of the amino acid or on one or more of the side-chain functionalities of the amino acids. Herein, each alkyl group may independently represent a (substituted or unsubstituted) C1-C7 alkyl group, preferably a (substituted or unsubstituted) linear C1-C6 alkyl group, more preferably a (substituted or unsubstituted) linear C1-C3 alkyl group, and most preferably a methyl group. Good results have in particular been achieved in a method of the invention wherein both R$_1$ and R$_2$ represent a hydrogen atom or wherein R$_1$ represents a hydrogen atom and R$_2$ represents an amino acid or peptide residue with a C-terminal carboxyamide or carboxylic acid functionality, optionally protected on the side-chain functionality of the amino acid or on one or more of the side-chain functionalities of the amino acids. Particularly good results have been achieved when using the Cam-ester, when X$_1$, X$_2$, R$_1$ and R$_2$ are a hydrogen atom.

The (oligo)peptide C-terminal (thio)ester can be N-terminally unprotected or N-terminally protected. In an embodiment, one or more side-chain functionalities (in particular carboxyl groups, amine groups), e.g. all side-chain functionalities, are provided with a protecting group; in another embodiment all the side-chain functionalities are unprotected. In a preferred embodiment, only the side-chain functionalities of the amino acids at the P4 and P1 position of the (oligo)peptide acyl donor and at the P1' or P2' position of the (oligo)peptide nucleophile (in particular hydroxy groups, carboxyl groups or amine groups) are provided with a protecting group. Suitable protecting groups are known to the person skilled in the art. Carboxylic acid groups can for instance be protected with a cyclohexyl, benzyl or allyl group; amine functionalities can for instance be protected with an allyloxycarbonyl group or a trifluoroacetyl group.

The activated C-terminal (thio)ester group of the (oligo) peptide C-terminal (thio)ester can be synthesized using solid phase synthesis in high yield and purity without racemization. An additional advantage of the use of (thio)esters wherein $R_1$ represents a hydrogen atom and $R_2$ represents an amino acid or peptide residue with a C-terminal carboxylic acid functionality, optionally protected on the side-chain functionality of the amino acid or on one or more of the side-chain functionalities of the amino acids is, that their activated C-terminal ester or thioester group can be synthesized using the cheap and industrially available 2-chlorotritylchloride resin.

The activated C-terminal (thio)ester group of the (oligo) peptide C-terminal (thio)ester can also be synthesized by fermentation using a microorganism. A reliable method to obtain (oligo)peptide (thio)esters using fermentation is via so-called intein expression (see for instance E. K. Lee, Journal of Chemical Technology and Biotechnology, 2010, 9, 11-18). Different intein expression systems kits are commercially available (for instance the IMPACT™ kit). Other methods for the fermentative production of (oligo)peptide (thio)esters are known in the art.

The C-terminal amino acid of the (oligo)peptide C-terminal (thio)ester and the other amino acids of the (oligo) peptide C-terminal (thio)ester may in principle be any amino acid, proteinogenic or non-proteinogenic.

If the amino acid sequence of the C-terminal part of the (oligo)peptide C-terminal (thio)ester is poorly recognized by or inaccessible to the coupling enzyme due to the amino acid preference of the coupling enzyme and/or due to the secondary or tertiary structure of the (oligo)peptide, the primary structure (amino acid sequence) may be elongated at the C-terminus. Essentially the C-terminus of the (oligo)peptide C-terminal (thio)ester is elongated with a number of amino acids to ensure good recognition by the enzyme and accessibility into the enzyme for the enzymatic coupling reaction. The skilled person will know how to elongate the (oligo) peptide C-terminal (thio)ester on the basis of the information disclosed herein and common general knowledge. Usually the number of amino acids for elongation is in the range of 1-10, although in principle it can be higher. Good results have been obtained by elongation of the (oligo)peptide C-terminal (thio)ester with 4 amino acid residues, e.g. -Phe-Ser-Lys-Leu-(thio)ester.

In particular the (optionally N-terminal protected) (oligo) peptide C-terminal (thio)ester may be represented by a compound of Formula I.

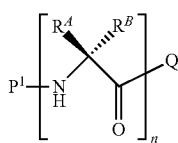

Formula I

Herein Q represents an OR or SR moiety. R may represent a (substituted or unsubstituted) alkyl or a (substituted or unsubstituted) aryl group.

Herein $P^1$ stands for a hydrogen or an N-terminal protecting group. Suitable N-terminal protecting groups are those N-protecting groups which can be used for the synthesis of (oligo)peptides. Such groups are known to the person skilled in the art. Examples of suitable N-protecting groups include carbamate or acyl type protecting groups, for instance 'Cbz' (benzyloxycarbonyl), 'Boc' (tert-butyloxycarbonyl), 'For' (formyl), 'Fmoc' (9-fluorenylmethoxycarbonyl), 'PhAc' (phenacetyl) and 'Ac' (acetyl). The groups For, PhAc and Ac may be introduced and cleaved enzymatically using the enzymes Peptide Deformylase, PenG acylase or Acylase, respectively. Chemical cleavage methods are generally known in the art.

Herein, n is an integer of at least 2. n May in particular be at least 3, at least 4, at least 5, at least 6, at least 7 at least 8, at least 9 or at least 10. n May in particular be 100 or less, 75 or less, 50 or less, 25 or less, 20 or less 15 or less, e.g. 10 or less.

Herein, each $R^A$ and each $R^B$ independently represent a hydrogen atom or an organic moiety, preferably an amino acid side-chain. Thus, it is not required that $R^A$ is the same in all n amino acid units. Similarly, it is not required that $R^B$ is the same in all n amino acid units. Optionally, one or more of the side-chain functionalities may contain a protecting group.

The amino acid units of the (oligo)peptide nucleophile may in principle be selected from any amino acid, proteinogenic or non-proteinogenic.

In particular, the (oligo)peptide nucleophile may be represented by a compound of Formula II.

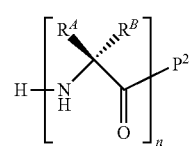

Formula II

Herein, n, $R^A$ and $R^B$ are as defined above.

Herein $P^2$ represents an amine moiety or an OR moiety.

In case $P^2$ represents an amine moiety, the amine moiety may be represented by the formula $NR_3R_4$, in which $R_3$ and $R_4$ may each individually represent any (substituted or unsubstituted) alkyl or (substituted or unsubstituted) aryl group. In particular, one out of $R_3$ and $R_4$ is a hydrogen atom and the other a (substituted or unsubstituted) alkyl group. Good results have particularly been obtained with $R_3$ and $R_4$ both being a hydrogen atom.

In case $P^2$ represents an OR moiety, R may represent a C-terminal protective group or a cation, for instance a monovalent cation, such as a tri- or tetrasubstituted ammonium ion or an alkaline metal cation or an H. In case R is a C-terminal protective group this may in particular be an optionally substituted alkyl group. Preferably it is a t-alkyl group, although in principle it also may be any other protective ester as known to a man skilled in the art. The t-alkyl may in principle be any protective tertiary alkyl group. Preferably the t-alkyl is selected from the group of t-butyl (2-methyl-2-propyl), t-pentyl (2-methyl-2-butyl) and t-hexyl (2,3-dimethyl-2-butyl).

In an embodiment, the (oligo)peptide nucleophile is C-terminal protected. In another embodiment it is not C-terminal protected.

The (oligo)peptide nucleophile to be used in a enzymatic synthesis process of the invention may be synthesized using methods known in the art, such as solid-phase synthesis, solution phase synthesis or by fermentation using a microorganism. The N-terminal amino acid of the (oligo)peptide nucleophile and the other amino acids of the (oligo)peptide nucleophile may in principle be any amino acid, proteinogenic or non-proteinogenic. If the amino acid sequence of the N-terminal part of the (oligo)peptide nucleophile is poorly recognized by or inaccessible to the coupling enzyme due to the amino acid preference of the coupling enzyme or due to the secondary or tertiary structure of the (oligo)

peptide nucleophile, the primary structure (amino acid sequence) may be elongated at the N-terminus. Essentially the N-terminus of the (oligo)peptide nucleophile is elongated with a number of amino acids to ensure good recognition by and accessibility to the coupling enzyme for the enzymatic coupling reaction. The skilled person will know how to elongate the (oligo)peptide nucleophile on the basis of the information disclosed herein and common general knowledge. Usually the number of amino acids for elongation is in the range of 1-10, although in principle it can be higher. Good results have been obtained by elongation of the (oligo)peptide nucleophile with 3 amino acid residues, e.g. H-Ser-Tyr-Arg.

A process for enzymatically synthesizing an (oligo)peptide from a first peptide fragment and a second peptide fragment, typically comprises providing a first fragment (that is a (oligo)peptide C-terminal ester or thioester. The second fragment (b) is an (oligo)peptide nucleophile having an N-terminally unprotected amine. In an embodiment, the N-terminus of the (oligo)peptide C-terminal ester or thioester and/or one or more side-chain functionalities of the (oligo)peptide C-terminal ester or thioester are provided with a protective group. In a further embodiment the C-terminus of the (oligo)peptide nucleophile is provided with a protective group and/or one or more side-chain functionalities of the (oligo)peptide nucleophile are provided with a protective group (see also e.g. above when discussing designing a synthesis process). Each of the fragments usually has two or more amino acid units, in particular three or more amino acid units. Evidently, as a result, each of the fragments usually has two or more amino acids less than the (oligo)peptide to be synthesised. An enzymatic synthesis process according to the invention, in particular such process making use of a subtilisine as a ligase, has been found suitable to couple peptide fragments wherein at least one of the peptides is relatively long. This is an advantage because this adds to flexibility of the process and reduces the number of enzymatic coupling reactions that is needed to synthesise a relatively long (oligo)peptide, such as an (oligo)peptide of more than 10, more than 20 or more than 25 amino acid units. Thus, in an advantageous embodiment, at least one of the peptide fragments has at least 5 amino acid units, more preferably at least 10 amino acid units, more preferably at least 15 amino acids, in particular at least 20 amino acids.

As indicated above, the invention also relates to a number of process for enzymatically synthesizing specific oligopeptides, namely a process for enzymatically synthesizing Exenatide or a longer (oligo)peptide comprising an amino acid sequence identical to the amino acid sequence of Exenatide or an analogue thereof, a process for enzymatically synthesizing Thymosin alpha 1 or a longer (oligo) peptide comprising an amino acid sequence identical to the amino acid sequence of Thymosin alpha 1 or analogue thereof, and a process for enzymatically synthesizing Lixisenatide or a longer (oligo)peptide comprising an amino acid sequence identical to the amino acid sequence of Lixisenatide or an analogue thereof respectively, wherein an (oligo)peptide C-terminal ester or thioester (the 'first fragment') and an (oligo)peptide nucleophile having an N-terminally unprotected amine (the 'second fragment') are enzymatically coupled, using a ligase as a catalyst. The ligase typically is a subtilisin BPN' variant or a homologue thereof as described in more detail elsewhere in the present description or claims.

Next, for each of these three processes separately, preferred fragments to be used in the coupling are described. Use is made of the three letter codes for the amino acids. Optionally present protective groups, i.e.: optionally present protective groups to protect side-chain functionalities of the first fragment, optionally present protective groups to protect side-chain functionalities of the second fragment, an optionally present protective group to protect the N-terminus of the first fragment and an optionally present protective group to protect the C-terminus of the second fragment are not shown. Although one or more of such groups may be present, good results have been achieved with fragments that are free of protective groups.

In a preferred process for the enzymatic synthesis of Exenatide, the first fragment is $His^1$-$Gly^2$-$Glu^3$-$Gly^4$-$Thr^5$-$Phe^6$-$Thr^7$-$Ser^8$-$Asp^9$-$Leu^{10}$-$Ser^{11}$-$Lys^{12}$-$Gln^{13}$-$Met^{14}$-$Glu^{15}$-$Glu^{16}$-$Glu^{17}$-$Ala^{18}$-$Val^{19}$-$Arg^{20}$-$Leu^{21}$-(thio)ester (1-21-(thio)ester) or a segment thereof at least comprising $Arg^{20}$-$Leu^{21}$-(thio)ester and the second fragment is H-$Phe^{22}$-$Ile^{23}$-$Glu^{24}$-$Trp^{25}$-$Leu^{26}$-$Lys^{27}$-$Asn^{28}$-$Gly^{29}$-$Gly^{30}$-$Pro^{31}$-$Ser^{32}$-$Ser^{33}$-$Gly^{34}$-$Ala^{35}$-$Pro^{36}$-$Pro^{37}$-$Pro^{38}$-$Ser^{39}$-$NH_2$ (22-39-$NH_2$) or a segment thereof at least comprising H-$Phe^{22}$-$Ile^{23}$, wherein the superscripts following the amino acid three-letter code refer to the position of said amino acid in Exenatide. An example of an oligopeptide which is a segment of H-$Phe^{22}$-$Ile^{23}$-$Glu^{24}$-$Trp^{25}$-$Leu^{26}$-$Lys^{27}$-$Asn^{28}$-$Gly^{29}$-$Gly^{30}$-$Pro^{31}$-$Ser^{32}$-$Ser^{33}$-$Gly^{34}$-$Ala^{35}$-$Pro^{36}$-$Pro^{37}$-$Pro^{38}$-$Ser^{39}$-$NH_2$ (22-39-$NH_2$) that may be used as a second fragment is the tripeptide H-Phe-Ile-Glu (corresponding to H-$Phe^{22}$-$Ile^{23}$-$Glu^{24}$ of Exenatide).

In a further preferred process for the enzymatic synthesis of Exenatide, the first fragment is $His^1$-$Gly^2$-$Glu^3$-$Gly^4$-$Thr^5$-$Phe^6$-$Thr^7$-$Ser^8$-$Asp^9$-$Leu^{10}$-$Ser^{11}$-$Lys^{12}$-$Gln^{13}$-$Met^{14}$-$Glu^{15}$-$Glu^{16}$-$Glu^{17}$-$Ala^{18}$-$Val^{19}$-$Arg^{20}$-$Leu^{21}$-$Phe^{22}$-$Ile^{23}$-$Glu^{24}$-(thio)ester) or a segment thereof at least comprising $Ile^{23}$-$Glu^{24}$-(thio)ester and the second fragment is H-$Trp^{25}$-$Leu^{26}$-$Lys^{27}$-$Asn^{28}$-$Gly^{29}$-$Gly^{30}$-$Pro^{31}$-$Ser^{32}$-$Ser^{33}$-$Gly^{34}$-$Ala^{35}$-$Pro^{36}$-$Pro^{37}$-$Pro^{38}$-$Ser^{39}$-$NH_2$ or a segment thereof at least comprising H-$Trp^{25}$-$Leu^{26}$, wherein the superscripts following the amino acid three-letter code refer to the position of said amino acid in Exenatide. A specific example for a first fragment that is a segment of $His^1$-$Gly^2$-$Glu^3$-$Gly^4$-$Thr^5$-$Phe^6$-$Thr^7$-$Ser^8$-$Asp^9$-$Leu^{10}$-$Ser^{11}$-$Lys^{12}$-$Gln^{13}$-$Met^{14}$-$Glu^{15}$-$Glu^{16}$-$Glu^{17}$-$Ala^{18}$-$Val^{19}$-$Arg^{20}$-$Leu^{21}$-$Phe^{22}$-$Ile^{23}$-$Glu^{24}$-(thio)ester is Phe-Ile-Glu-(thio)ester.

In a method for preparing an (oligo)peptide that is longer than Exenatide and that comprises an amino acid sequence identical to the amino acid sequence of Exenatide, the first fragment advantageously is a fragment comprising the amino sequence of a first fragment for the synthesis of Exenatide described in the previous paragraphs having the C-terminal (thio)ester at the corresponding position yet one or more amino acid units prior to the $His^1$ or the second fragment is a fragment comprising the amino sequence of a second fragment for the synthesis of Exenatide described in the previous paragraphs having the N-terminally unprotected amine at the corresponding position in the second fragment, yet one or more amino acid units after the $Ser^{39}$, e.g. the first fragment may be $His^1$-$Gly^2$-$Glu^3$-$Gly^4$-$Thr^5$-$Phe^6$-$Thr^7$-$Ser^8$-$Asp^9$-$Leu^{10}$-$Ser^{11}$-$Lys^{12}$-$Gln^{13}$-$Met^{14}$-$Glu^{15}$-$Glu^{16}$-$Glu^{17}$-$Ala^{18}$-$Val^{19}$-$Arg^{20}$-$Leu^{21}$-$Phe^{22}$-$Ile^{23}$-$Glu^{24}$-(thio)ester) and the second fragment may then be H-$Trp^{25}$-$Leu^{26}$-$Lys^{27}$-$Asn^{28}$-$Gly^{29}$-$Gly^{30}$-$Pro^{31}$-$Ser^{32}$-$Ser^{33}$-$Gly^{34}$-$Ala^{35}$-$Pro^{36}$-$Pro^{37}$-$Pro^{38}$-$Ser^{39}$-$AA^{40}$-$AA^{41}$ . . . -$AA^{y-1}$-$AA^y$-$NH_2$. Herein y is a natural number and each 'AA' independently stands for an amino acid.

In a preferred process for the enzymatic synthesis of Thymosin-alpha-1 the first fragment is Ac-$Ser^1$-$Asp^2$-$Ala^3$-$Ala^4$-$Val^5$-$Asp^6$-$Thr^7$-$Ser^8$-$Ser^9$-$Glu^{10}$-$Ile^{11}$-$Thr^{12}$-$Thr^{13}$-$Lys^{14}$-(thio)ester or a segment thereof at least comprising Thr$^{13}$-Lys$^{14}$-(thio)ester and the second fragment is H-Asp$^{15}$-Leu$^{16}$-Lys$^{17}$-Glu$^{18}$-Lys$^{19}$-Lys$^{20}$-Glu$^{21}$-Val$^{22}$-Val$^{23}$-Glu$^{24}$-Glu$^{25}$-Ala$^{26}$-Glu$^{27}$-Asn$^{28}$-OH or a segment thereof at least comprising is Asp$^{15}$-Leu$^{16}$ wherein the superscripts following the amino acid three-letter code refer to the position of said amino acid in Thymosin-alpha-1.

In a method for preparing an (oligo)peptide that is longer than Thymosin-alpha-1 and that comprises an amino acid sequence identical to the amino acid sequence of Thymosin-alpha-1, the first fragment advantageously is a fragment comprising the amino sequence of first fragment for the synthesis of Thymosin-alpha-1 described in the previous paragraph having the C-terminal (thio)ester at the corresponding position yet one or more amino acid units prior to the Ser$^1$ or the second fragment is a fragment comprising the amino sequence of a second fragment for the synthesis of Thymosin-alpha-1 described in the previous paragraph having the N-terminally unprotected amine at the corresponding position in the second fragment, yet one or more amino acid units after the Asn$^{28}$.

In a preferred process for the enzymatic synthesis of Lixisenatide the first fragment is His$^1$-Gly$^2$-Glu$^3$-Gly$^4$-Thr$^5$-Phe$^6$-Thr$^7$-Ser$^8$-Asp$^9$-Leu$^{10}$-Ser$^{11}$-Lys$^{12}$-Gln$^{13}$-Met$^{14}$-Glu$^{15}$-Glu$^{16}$-Glu$^{17}$-Ala$^{18}$-Val$^{19}$-Arg$^{20}$-Leu$^{21}$-(thio)ester (H-1-21-(thio)ester) or a segment thereof at least comprising Arg$^{20}$-Leu$^{21}$-(thio)ester and the second fragment is H-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Ser$^{38}$-Lys$^{39}$-Lys$^{40}$-Lys$^{41}$-Lys$^{42}$-Lys$^{43}$-Lys$^{44}$-NH$_2$ (22-44-NH$_2$) or a segment thereof, at least comprising H-Phe$^{22}$-Ile$^{23}$, wherein the superscripts following the amino acid three-letter code refer to the position of said amino acid in Lixisenatide.

In a method for preparing an (oligo)peptide that is longer than Lixisenatide that comprises an amino acid sequence identical to the amino acid sequence of Lixisenatide, the first fragment advantageously is a fragment comprising the amino sequence of the first fragment for the synthesis of Lixisenatide described in the previous paragraph having the C-terminal (thio)ester at the corresponding position yet one or more amino acid units prior to the His$^1$ or the second fragment is a fragment comprising the amino sequence of a second fragment for the synthesis of Lixisenatide described in the previous paragraph having the N-terminally unprotected amine at the corresponding position in the second fragment, yet one or more amino acid units after the Lys$^{44}$.

Regarding the analogues of an (oligo)peptide, such as Exenatide, Thymosin alpha 1, Lixisenatide, this term is used in particular for (oligo)peptides that are structural analogues and/or functional analogues of said (oligo)peptide. Functional analogues have a same in vivo target (e.g. the same target receptor on a cell membrane); structural analogues have a high similarity in amino acid sequence. Functional analogues of an (oligo)peptide may have a relatively low amino acid sequence identity, e.g. of about 50% or less over the full amino acid sequence, yet at high sequence identity (and thus high structural similarity) with the (oligo)peptide of which they are an analogue in a segment of the amino acid sequence, such as near the N-terminal part or near the C-terminal part. A structural analogue, in particular comprises an amino acid sequence that has at least 60%, more in particular at least 70%, preferably at least 80%, more preferably at least 90% sequence identity, more preferably at least 95% sequence identity with the amino acid sequence of Exenatide, Thymosin alpha 1 and Lixisenatide respectively. Specific analogues of Exenatide are Glp-1, Teduglutide, Glucagon, Liraglutide and Semaglutide, of which Glp-1, Teduglutide and Glucagon are particularly preferred analogues.

In a method or process according to the invention, at least when subtilisin variants or homologues thereof are used, the enzymatic hydrolysis respectively enzymatic coupling reaction are usually performed in a fluid comprising water. The reaction may be carried out in a fully aqueous liquid or in a mixture of water and a water mixable co-solvent such as N,N-dimethylformamide (DMF), N-methyl-pyrrolidinone (NMP), N,N-dimethylacetamide (DMA), dimethylsulphoxide (DMSO), acetonitrile, an ether, such as tetrahydrofuran (THF), 2-methyl-tetrahydrofuran (Me-THF) or 1,2-dimethoxyethane, or a (halogenated) alcohol, such as methanol, ethanol, isopropanol, tert-butanol, 2,2,2-trifluoroethanol (TFE), 1,1,1,3,3,3-hexafluoroisopropanol, or a mixture of these organic solvents. Depending on the stability of the enzyme and the solubility of the (oligo)peptide respectively the (oligo)peptide fragments substrates, the amount of co-solvent is preferably below 70 vol %, more preferably below 60 vol %, even more preferably below 50 vol %, and most preferably below 40%. The water content usually is 10-100 vol %, based on total liquids, preferably 20 vol. % or more, preferably 40 vol. % or more, in particular 50 vol. % or more, more in particular 60 vol. % or more, 80 vol. % or more or 95 mol. % or more.

Preferably the reaction is performed in a buffered fluid. In principle, any buffer is suitable. Good buffers are known to a person skilled in the art. See for instance David Sheehan in Physical Biochemistry, 2"d Ed. Wiley-VCH Verlag GmbH, Weinheim 2009; or http://www.amazon.com/Buffer-Solutions-BASICS-Garland-Science/dp/0199634424).

The pH of the buffer for hydrolysis or coupling (by fragment condensation) may be at least 5, in particular at least 6, preferably at least 7. A desired maximum pH is usually less than 11, in particular less than 10, even more preferably less than 9. Usually the optimal pH for the enzymatic reactions is between 7 and 9 The pH used for the hydrolytic reaction may be about the same as for the coupling reaction.

A cyclase according to the invention may be used for the synthesis of a cyclic (oligo)peptide, i.e. an (oligo)peptide chain wherein the alpha-amino terminus and the alpha-carboxyl terminus of a branched or linear (oligo)peptide are linked via a peptide bond, thereby forming a ring structure, preferably of at least 12 amino acid units. For cyclisation reactions the optimal pH can be different. The pH for the cyclisation reaction may be at least 3, in particular at least 4, preferably at least 5. A desired maximum pH is usually less than 11, in particular less than 10, preferably less than 9. Usually the optimal pH for the enzymatic cyclisation reactions is between 5 and 9.

In the coupling reaction with a ligase according to the invention, a large excess of the (oligo)peptide C-terminal ester or thioester or of the (oligo)peptide nucleophile is generally not needed to reach a high yield in the condensation reaction. Usually the ratio of (a) the (oligo)peptide C-terminal ester or thioester to (b) the (oligo)peptide nucleophile is between 1:5 and 5:1, preferably in the range of 1:3 to 3:1, more preferably in the range of 1.0:2.5 to 2.5:1.0, in particular in the range of 1:2 to 2:1, more in particular in the range of 1:1.5 to 1.5:1. An about stoichiometric ratio has been found particularly effective.

In particular, in method for designing a synthesis process or in a synthesis process of the invention, it may be advantageous to add additives to the fluid wherein the reaction is carried out to improve the solubility of the (oligo)peptide fragments (or of the non-cyclic (oligo)peptide for synthesis of a cyclic (oligo)peptide) or to improve the reaction yield. Such additives may be a salt or an organic molecule, for instance guanidinium hydrochloride, urea, sodium dodecasulphate or a polysorbate, such as Tween®.

In principle the temperature during the enzymatic fragment condensation or cyclisation is not critical, as long as a temperature is chosen at which the coupling enzyme used shows sufficient activity and stability. Such a temperature is usually known for the coupling enzyme to be used or can be routinely determined based on common general knowledge, the information disclosed herein and optionally a limited amount of testing. Generally, the temperature may be at least −10° C., in particular at least 0° C. or at least 10° C. Generally, the temperature may be 70° C. or less, in particular 60° C. or less or 50° C. or less. Optimal temperature conditions can easily be identified for a specific coupling enzyme for a specific enzymatic fragment condensation or cyclisation by a person skilled in the art through routine experimentation based on common general knowledge and the information disclosed herein. In general, the temperature advantageously is in the range of 20-50° C.

In principle the concept of a method for designing an enzymatic peptide synthesis process of the present invention can be applied to any serine endoproteases having a corresponding coupling enzyme. In particular, preferred is a subtilisin variant or homologue thereof. Subtilisin variants and homologues are in particular selected from the group of subtilisin BPN' and its variants and subtilisin Carlsberg and its variants and homologues of any of these. Such enzymes having a serine at a hydrolytically active site are suitable as serine endoproteases in accordance with the invention. Variants or homologues wherein a serine in its hydrolytically active site is replaced by another amino acid, in particular cysteine or selenocysteine may be used as coupling enzymes.

In a particularly preferred embodiment, a subtilisin BPN' variant or homologue is used. E.g. subtiligase, as described by Wells, see above, may be used as the ligase in a process wherein fragments are used that have been identified using a subtiligase mutant wherein the amino acid corresponding to position 221 is not cysteine (as is the case in subtiligase) but serine, as in the wild type subtilisin BPN'. However, the present inventors found that further improvements can be made in providing a subtilisin BPN' ligase or cyclase variant or homologue thereof, with a significant higher stability, an improved S/H ratio and/or an improved enzymatic activity.

In particular, good results have been achieved with a subtilisin BPN' variant or homologue, used as a ligase or cyclase in a process for synthesizing an (oligo)peptide according to the invention, having
  a deletion of the amino acids corresponding to positions L75, N76, N77, S78, I79, G80, V81, L82 and G83 of subtilisin BPN' (thus in general a deletion of a corresponding Ca2+ binding site);
  a mutation at the amino acid position corresponding to S221, the mutation being S221C or S221 selenocysteine;
  preferably a mutation at the amino acid position corresponding to P225
wherein the amino acid positions are defined according to the sequence of subtilisin BPN' represented by SEQUENCE ID NO: 2.

It has surprisingly been found possible to use such a subtilisin BPN' variant or homologue to enzymatically condense two (oligo)peptide fragments in a liquid comprising water with a high synthesis over hydrolysis ratio. Thus, it offers the possibility for coupling various (oligo)peptide fragments in aqueous solution in high yield without substantial hydrolytic side reactions. Further, it has been found that such a subtilisin BPN' variant or homologue has cyclase activity in the cyclisation of a non-cyclic (oligo)peptide.

Accordingly, the invention in particular relates to a method for designing a synthesis process wherein such a subtilisin BPN' variant or homologue is used as the ligase or cyclase.

Accordingly, in a preferred method the endoprotease is a serine endoprotease, also having
  a deletion of the amino acids corresponding to positions 75-83;
  wherein the position corresponding to S221 is not mutated, i.e. is serine; wherein the amino acid positions are defined according to the sequence of subtilisin BPN' represented by SEQUENCE ID NO: 2, and An enzyme according to the invention, is thus preferably a serine endoprotease having
  a deletion of the amino acids corresponding to positions 75-83;
  wherein the amino acid positions are defined according to the sequence of subtilisin BPN' represented by SEQUENCE ID NO: 2, and wherein the position corresponding to S221 is not mutated, i.e. is serine; or
  the enzyme is a ligase or cyclase, having a
  a deletion of the amino acids corresponding to positions 75-83;
  a cysteine or selenocysteine at a position corresponding to position 221 in subtilisin BPN'
  wherein the amino acid positions are defined according to the sequence of subtilisin BPN' represented by SEQUENCE ID NO: 2.

Although in particular good results have been achieved with a ligase or cyclase, which ligase or cyclase is a variant of a serine endoprotease, wherein a serine in a hydrolytically active site of the serine endoprotease has been substituted by a cysteine, the inventors consider that substitution by a selenocysteine is also advantageous in increasing the S/H ratio. This insight is based in particular on a combination of the positive effects of substitution by cysteine within the context of the present invention, scientific literature reporting that the conversion of the active site serine to cysteine of subtilisin can increase the S/H ratio of the enzyme a 600 fold (Need and Koshland, Biochemistry, 1966, 1606-1611) and scientific literature reporting that the S/H ratio could be improved a 13.500 fold when the active site serine is converted to selenocysteine, although this enzyme is more oxygen sensitive (Wu, Z-P; Hilvert, D. J Am. Chem. Soc., 1989, 111, 4513-4514). Conversion of the active site serine to selenocysteine can be performed chemically (see Wu) or via fermentative production (Shen et. Al. Chinese Science Bulletin, 2008, 53, 2454-2461).

An enzyme of the invention may have further mutations compared to subtilisin BPN', provided that—in the case of the ligase—it has enzymatic fragment condensation activity in the preparation of an (oligo)peptide and—in the case of the cyclase—it catalyses the cyclisation of a non-cyclic (oligo)peptide via the formation of a peptide bond between its C-terminal end and N-terminal end. In particular the one or more further mutations are as described elsewhere herein.

Alternatives to subtilisin BPN', as template enzymes from which an enzyme according to the invention, in particular a homologue of a subtilisin BPN' variant of the invention, can be derived by mutagenesis are other subtilisins, in particular subtilisins having at least 50% homology with subtilisin BPN'.

Sequences of suitable subtilisins can be retrieved from the UNIPROT sequence database (http://www.uniprot.org/), as available on 11 Aug. 2014, by BLASTing the database with subtilisin BPN' (SEQ ID 2) as a query. However sequence retrieval is not limited to UNIPROT nor to the date. The skilled person in the art knows how to query alternative sequence depositories or to collect additional homologue sequences by sequencing (see for example *Zooming in on metagenomics: molecular microdiversity of Subtilisin Carlsberg in soil.*, Gabor E, Niehaus F, Aehle W, Eck J. J Mol Biol. 2012 Apr. 20; 418(1-2):16-20). In particular, the invention further relates to serine endoproteases which are variants hereof, having at least said deletions of the amino acids corresponding to L75 till and including G83 of subtilisin BPN', serine at a position corresponding to position 221 in subtilisin BPN' and preferably a mutation as mentioned herein at position corresponding to position 225 in subtilisin BPN', of any of the subtilisins mentioned in FIG. 14 of PCT/NL2014/050707 and WO 2016/056913, of which the full sequence is as available from said UNIPROT sequence data base and of which the alignments around positions 75-83 are shown. Likewise, suitable homologues of coupling enzymes used in a method or process of the invention are in particular variants, having at least said deletions of the amino acids corresponding to L75 till and including G83 of subtilisin BPN', cysteine or selenocystein at a position corresponding to position 221 in subtilisin BPN' and preferably a mutation as mentioned herein at position corresponding to position 225 in subtilisin BPN', of any of the subtilisins mentioned in FIG. 14 of PCT/NL2014/050707 and WO 2016/056913, of which the full sequence is as available from said UNIPROT sequence data base and of which the alignments around positions 75-83 are shown.

With respect to the coupling enzyme, the invention provides in particular an enzyme having catalytic activity with respect to the formation of a peptide bond (condensation activity), whereby it has catalytic activity in the synthesis of an (oligo)peptide with a high S/H ratio, compared to subtilisin BPN' and/or subtiligase. With respect to the ligase, the S/H ratio of the subtilisin BPN' variant or homologue thereof of the invention divided or by the S/H ratio of subtilisin BPN'— at least under the conditions described in Example 1 or one or more of the other Examples—is usually more than 100, preferably 250 or more, more preferably 500 or more, in particular 1000 or more. The upper value of this quotient is not critical; The S/H ratio of subtilisin BPN' at least under the reaction conditions specified herein is generally very low, it may be even zero (no detectable synthesis). Thus, the S/H ratio of the subtilisin BPN' variant or homologue thereof of the invention divided by the S/H ratio of subtilisin BPN' may approximate infinity. In a potential circumstance wherein subtilisin BPN' has substantial ligase or cyclase activity, the inventors consider that the S/H ratio of the subtilisin BPN' variant or homologue thereof of the invention divided by the S/H ratio of subtilisin BPN' is also high, e.g. up to 100 000, in particular up to 25 000, more in particular up to 10 000.

With respect to the serine endoprotease according to the invention this enzyme is in particular found to be useful in designing a (oligo)peptide synthesis process (making use of a corresponding ligase) using a method of the invention.

In particular, the invention provides an isolated enzyme (isolated from the organism wherein it has been expressed (typically a recombinant organism), if it has been produced in an organism or from the reaction medium in which it has been synthesized.

In particular, an enzyme of the invention is considered isolated for the purpose of the invention if it has been substantially purified by any suitable technique such as, for example, the single-step purification method disclosed in Smith and Johnson, Gene 67:31-40 (1988).

An enzyme of the present invention can be provided in at least substantially pure form (e.g. more than 75 wt. %, more than 80 wt. %) or in a mixture with one or more other components, e.g. in the form of a stock solution, in particular in an aqueous buffer solution.

Next, preferred mutations for serine endoproteases or coupling enzymes (ligases, cyclases) are given; these in particular apply to the subtilisin BPN' variant or homologue thereof.

In a preferred embodiment, the enzyme has a mutation at the amino acid position corresponding to P225.

For a serine endoprotease or coupling enzyme of the invention it is preferred that the mutation at the amino acid position corresponding to P225 is selected from the group of P225N, P225D, P225S, P225C, P225G, P225A, P225T, P225V, P225I, P225L, P225H and, P225Q. These mutations are in particular suitable for increasing the S/H ratio of a coupling enzyme compared to an otherwise the same coupling enzyme having a proline at the position corresponding to P225.

Preferably, an enzyme according to the invention comprises one or more mutations selected from the group of mutations at an amino acid position corresponding to Q2, S3, P5, S9, I31, K43, M50, A73, E156, G166, G169, S188, Q206, N212, N218, T254 and Q271 of SEQUENCE ID NO 2.

It is preferred that a plurality of said mutations are present in an enzyme of the invention, such as at least two, at least three, more preferably four or more, more preferably five or more, more preferably six or more, more preferably at least eight, more preferably at least 12 of the mutations selected from the group of Q2K, S3C, P5S, S9A, I31L, K43N, M50F, A73L, E156S, G166S, G169A, S188P, Q206C, N212G, N218S, T254A and Q271E. The inventors consider that in particular the presence of one or more of the mutations N218S, S3C-Q206C, G169A, T254A, A73L, M50F and Q2K are advantageous with respect to improving enzyme stability. Further, the inventors consider that in particular the presence of one or more of the mutations I31L, E156S, G166S, G169A, is advantageous with respect to improving activity and/or increasing S/H ratio, the increase in S/H ratio being particularly preferred for a coupling enzyme used in accordance with the invention.

It is particularly preferred that the serine endoprotease, ligase or cyclase comprises a mutation at each of the positions corresponding to Q2, P5, M50, A73 and N218, more in particular at each of the positions corresponding to Q2, P5, M50, A73, G166 and N218.

Preferably the serine endoprotease, ligase or cyclase comprises at least one or more of the following mutations:
a mutation at the amino acid position corresponding to N218, M50, A73, P5, G166, mutations at the amino acid position corresponding to S3C and Q206C (wherein the cysteins at the positions corresponding to position 3 and position 206 form a disulphur bridge). In particular, good results have been achieved with an enzyme comprising a mutation at each of the positions corresponding to N218, M50, Q2, A73. and P5, said mutations preferably being N218S, M50F, Q2K, A73L, P5S, more in particular with an enzyme comprising the mutations corresponding to Q2K, S3C, P5S, S9A, I31L, K43N, M50F, A73L, E156S, G166S, G169A, S188P, Q206C, N212G, N218S, T254A and Q271E of SEQUENCE ID NO 2.

Advantageously, the serine endoprotease, ligase or cyclase according to the invention comprises one or more mutations at the amino acid position corresponding to N62, G100, S125, L126, G127, P129, N155, Y217, N218 or M222 of SEQUENCE ID NO 2.

In a preferred embodiment, the serine endoprotease, ligase or cyclase has a mutation at an amino acid position corresponding to M222. Said mutation is usually selected from the group of M222G, M222P, M222N, M222E, M222Q and M222A, preferably M222G or M222P The mutation at Y217 is usually selected from the group of Y217L, Y217N, Y217E, Y217G, Y217F, Y217A, Y217S and Y217H. Preferably the mutation at Y217 is Y217F, Y217G or Y217H. A mutation in the position corresponding to M222 or Y217 has in particular been found useful to provide a ligase or cyclase with a broad substrate scope and a good S/H ratio.

Particularly good results have been obtained with a coupling enzyme having a mutation selected from the group of M222G, M222P and Y217L in that the S/H ratio and/or the activity is significantly increased, at least for a number of peptide sequences.

Preferably, the enzyme comprises a mutation at one, two or each of the positions corresponding to Y104, 1107 and L135. Particularly good results have been obtained with a subtilisin BPN' variant having a mutation selected from the group of Y104F, Y104S, I107V, I107A, L135N, L135S, L135D and L135A.

In a preferred embodiment, the serine endoprotease, ligase or cyclase thereof has a mutation at an amino acid position corresponding to L135. For a serine endoprotease, most preferably, said mutation at amino acid position corresponding to L135 is either L135N or L135S. For a coupling enzyme, said mutation preferably is selected from L135N, L135S, L135D and L135A. Substitution of these amino acids can significantly alter and improve the S/H ratio of the coupling enzyme and/or the activity of the coupling enzyme, at least for certain substrates. In a preferred embodiment, the serine endoprotease, ligase or cyclase has a mutation at an amino acid position corresponding to 1107. For a serine endoprotease this mutation preferably is I1107V.

For a coupling enzyme this mutation preferably is I1107V or I1107A. Substitution of these amino acids can significantly alter and improve the S/H ratio of the coupling enzyme and/or the activity of the enzyme, at least for certain substrates.

A coupling enzyme preferably has a mutation Y104F or Y104S for an improved S/H ratio or the activity.

In particular, a substitution in the amino acid corresponding to 1107 (I107V) or a substitution in L135 (L135S or L135N) may improve substrate scope.

In a preferred embodiment, the serine endoprotease, ligase or cyclase has a mutation both at the position corresponding to M222 and the position corresponding to Y217, which mutations are corresponding to M222P+L217H M222P+L217G, M222G+L217G, or M222G+L217F.

Advantageously, the coupling enzyme according to the invention comprises at least one mutation selected from the group of mutations at an amino acid position corresponding to Y104, L126, S101, G102, G127, G128, and P168 of SEQUENCE ID NO 2. At least one of said mutations is preferably selected from the group of Y104F and Y104S.

A serine endoprotease or coupling enzyme according to the invention, preferably has a sequence identity with SEQUENCE ID 3, 4 or 5 of 50-100%, preferably at least 70%, more preferably of at least 80%, more preferably of at least 85%, in particular of at least 90%, more in particular of at least 95%.

The the serine endoprotease, ligase or cyclase, such as the subtilisin BPN' variants of the present invention, are generally produced by recombinant methods, based on common general knowledge and the information disclosed herein, in particular by expression of a subtilisin BPN' DNA which has been mutated such that upon expression it results in a subtilisin BPN' variant of the invention which is enzymatically active.

Expression of the DNA of the subtilisin BPN' variants and homologues thereof of the present invention is provided using available vectors and regulatory sequences. The actual selection depends in large part upon the particular host cells which are utilized for expression. For example, if the subtilisin BPN' mutant DNA is expressed in *Bacillus*, a *Bacillus* promoter is generally utilized as well as a *Bacillus* derived vector.

In order to produce and secrete the enzyme of the invention from a host cell into the medium, a gene may be used which encodes a precursor polypeptide (enzyme) containing a signal sequence and a pre-pro sequence preceding the mature enzyme. In subtilisin BPN', the additional N-terminal sequence comprises 107 amino acids. Upon secretion first the signal sequence can be removed and after secretion the pre-pro sequence can be removed resulting in the fully active enzyme (James A. Wells, Nucleic Acids Research, Volume 11 Number 22 1983). In case of native subtilisin BPN' the mature enzyme comprises 275 amino acids. Conveniently to describe the position of individual amino acids in the polypeptide chain of subtilisin BPN' and its homologues the so called subtilisin BPN' numbering is used which runs from the N-terminus (amino acid 1) tot the C-terminus (amino acid 275). Corresponding positions in homologous enzymes can be determined by aligning said homologous sequences with the sequence of subtilisin BPN'.

As is known to the person skilled in the art, it is possible that the N- and/or C-termini of the mature polypeptide numbered 1-275 within SEQ ID NO: 5 or of the mature enzyme in the amino acid sequence according to SEQ ID NO: 2, 3 or 4 (as set out in amino acids 1 to 275) maybe heterogeneous, due to variations in processing during maturation. In particular such processing variations might occur upon overexpression of the enzyme. In addition, exo-protease activity might give rise to heterogeneity. The extent to which heterogeneity occurs depends also on the host and fermentation protocols that are used. Such C-terminal processing artefacts might lead to shorter polypeptides or longer polypeptides than indicated with the mature wild-type subtilisin BPN' (SEQ ID NO: 2) or with the mature enzymes according to the invention represented by SEQ ID NO: 3 or 4. As a result of such processing variations the N-terminus might also be heterogeneous. Processing variants at the N-terminus could be due to alternative cleavage of the signal sequence by signal peptidases.

For secretion of the translated enzyme into the lumen of the endoplasmic reticulum, into the periplasmic space or into the extracellular environment, an appropriate secretion signal sequence may be fused to the polynucleotide encoding the enzyme of the invention. The signals may be endogenous to the enzyme or they may be heterologous signals.

The enzyme according to the invention may be produced in a modified form, such as a fusion protein, and may include not only secretion signals but also additional heterologous functional regions. Thus, for instance, a region of additional amino acids (a so called tag), particularly charged amino acids, may be added to the enzyme, in particular to the C-terminus of the enzyme, to improve stability and persistence in the host cell, during purification or during subsequent handling and storage or to facilitate the purification. Examples of suitable tags are for instance described in a review by M. E. Kimple et al., in 'Current Protocols in Protein Science 9.9.1-9.9.23, August 2013'. A well known example of a useful tag is the so called His tag, an amino acid sequence having a plurality of histidine units. The inventors found that such a tag could be used successfully in the production and purification of enzymes of the invention. No substantial differences in functional enzyme properties were observed between enzymes with the His tag and enzymes without the His tag.

Further, an enzyme of the invention can be produced as an inclusion body with refolding in an appropriate buffer.

Enzymes of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the enzymes of the present invention may be glycosylated or may be non-glycosylated. In addition, enzymes of the invention may also include an initial modified methionine residue, in some cases as a result of host-mediated processes.

Polynucleotides of the invention can be incorporated into a vector, including cloning and expression vectors. A vector may be a recombinant replicable vector. The vector may be used to replicate a polynucleotide of the invention in a compatible host cell. The vector may conveniently be subjected to recombinant DNA procedures.

The invention also pertains to methods of growing, transforming or transfecting such vectors in a suitable host cell, for example under conditions in which expression of an enzyme of the invention occurs. The invention provides a method of making enzymes of the invention by introducing a polynucleotide of the invention into a vector, in an embodiment an expression vector, introducing the vector into a compatible host cell, and growing the host cell under conditions which bring about replication of the vector. The vector may be recovered from the host cell.

A vector according to the invention may be an autonomously replicating vector, i.e. a vector which exists as an extra-chromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

One type of vector is a "plasmid", which refers to a circular double stranded DNA loop into which additional DNA segments can be inserted. Another type of vector is a viral vector, wherein additional DNA segments can be inserted into the viral genome.

Certain vectors are capable of autonomous replication in a host cell into which they are introduced (e.g., bacterial vectors having a bacterial origin of replication and episomal mammalian vectors). Other vectors (e.g., bacterial integration vector without a suitable origin of replication or a non-episomal mammalian vectors) are integrated into the genome of a host cell upon introduction into the host cell, and thereby are replicated along with the host genome.

The recombinant expression vectors of the invention comprise a polynucleotide of the invention in a form suitable for expression of the polynucleotide in a host cell, which means that the recombinant expression vector includes one or more regulatory sequences, selected on the basis of the host cells to be used for expression, which is operably linked to the polynucleotide sequence to be expressed. The term regulatory sequence includes promoters, enhancers and other expression control elements (e.g., polyadenylation signal). Such regulatory sequences are described, for example, in Goeddel; Gene Expression Technology: Methods in Enzymology 185, Academic Press, San Diego, Calif. (1990).

A vector or expression construct for a given host cell may thus comprise the following elements operably linked to each other in a consecutive order from the 5'-end to 3'-end relative to the coding strand of the sequence encoding an enzyme of the invention: (1) a promoter sequence capable of directing transcription of the nucleotide sequence encoding the enzyme in the given host cell; (2) a ribosome binding site to facilitate the translation of the transcribed RNA (3) optionally, a signal sequence capable of directing secretion of the enzyme from the given host cell into a culture medium; (4) a polynucleotide sequence according to the invention; and preferably also (5) a transcription termination region (terminator) capable of terminating transcription downstream of the nucleotide sequence encoding the enzyme.

Downstream of the nucleotide sequence according to the invention there may be a 3' untranslated region containing one or more transcription termination sites (e.g. a terminator, herein also referred to as a stop codon). The origin of the terminator is less critical. The terminator can, for example, be native to the DNA sequence encoding the enzyme. However, preferably a bacterial terminator is used in bacterial host cells and a filamentous fungal terminator is used in filamentous fungal host cells. More preferably, the terminator is endogenous to the host cell (in which the nucleotide sequence encoding the enzyme is to be expressed). In the transcribed region, a ribosome binding site for translation may be present. The coding portion of the mature transcripts expressed by the constructs will include a start codon is usually AUG (or ATG), but there are also alternative start codons, such as for example GUG (or GTG) and UUG (or TTG), which are used in prokaryotes. Also a stop or translation termination codon is appropriately positioned at the end of the polypeptide to be translated.

Enhanced expression of the polynucleotide of the invention may also be achieved by the selection of homologous and heterologous regulatory regions, e.g. promoter, secretion leader and/or terminator regions, which may serve to increase expression and, if desired, secretion levels of the protein of interest from the expression host and/or to provide for the inducible control of the expression of an enzyme of the invention.

The enzymes according to the invention can be produced in bacterial cells such as *E. coli* and Bacilli, insect cells (using baculovirus expression vectors), fungal cells, yeast cells or mammalian cells. Suitable host cells are discussed herein and further in Goeddel, Gene Expression Technology: Methods in Enzymology 185, Academic Press, San Diego, Calif. (1990) and in "Production of Recombinant Proteins: Novel Microbial and Eukaryotic Expression Systems", 2004, Wiley-Blackwell, Editor Gerd Gellissen (http://eu.wiley.com/WileyCDA/Section/id-302479.html?query=Gerd+

Gellissen). Alternatively, the recombinant expression vector can be transcribed and translated in vitro, for example using T7 promoter regulatory sequences and T7 polymerase.

For most bacteria, filamentous fungi and yeasts, the vector or expression construct is preferably integrated in the genome of the host cell in order to obtain stable transformants. In case the expression constructs are integrated in the host cells genome, the constructs are either integrated at random loci in the genome, or at predetermined target loci using homologous recombination, in which case the target loci preferably comprise a highly expressed gene.

In the invention, bacteria, in particular Bacilli, may preferably be used as host cells for the expression of an enzyme of the invention. Suitable inducible promoters useful in such host cells include promoters regulated primarily by an ancillary factor such as a repressor or an activator. The repressors are sequence-specific DNA binding proteins that repress promoter activity. The transcription can be initiated from this promoter in the presence of an inducer that prevents binding of the repressor to the operator of the promoter. Production of secondary sigma factors can be primarily responsible for the transcription from specific promoters. Attenuation and antitermination also regulates transcription.

Strong constitutive promoters are well known and an appropriate one may be selected according to the specific sequence to be controlled in the host cell. A variety of promoters can be used that are capable of directing transcription in the recombinant host cells of the invention. Preferably the promoter sequence is from a highly expressed gene.

Vector DNA can be introduced into prokaryotic or eukaryotic cells via natural competence, conventional transformation or transfection techniques. As used herein, the terms "transformation" and "transfection" are intended to refer to a variety of art-recognized techniques for introducing foreign polynucleotide (e.g., DNA) into a host cell, including calcium phosphate or calcium chloride co-precipitation, DEAE-dextran-mediated transfection, transduction, infection, lipofection, cationic lipid mediated transfection or electroporation. Suitable methods for transforming or transfecting host cells can be found in Sambrook, et al. (supra) and other laboratory manuals.

In order to identify and select cells which harbor a vector, a gene that encodes a selectable marker (e.g., resistance to antibiotics) is generally introduced into the host cells along with the polynucleotide of the invention. Preferred selectable markers include, but are not limited to, those which confer resistance to drugs or which complement a defect in the host cell. They also include e.g. versatile marker genes that can be used for transformation of most filamentous fungi and yeasts such as acetamidase genes or genes providing resistance to antibiotics like G418, hygromycin, bleomycin, kanamycin, methotrexate, phleomycin orbenomyl resistance (benA). Alternatively, specific selection markers can be used such as auxotrophic markers which require corresponding mutant host strains: e.g. D-alanine racemase (from *Bacillus*), URA3 (from *S. cerevisiae* or analogous genes from other yeasts), pyrG or pyrA (from *A. nidulans* or *A. niger*), argB (from *A. nidulans* or *A. niger*) or trpC. In an embodiment the selection marker is deleted from the transformed host cell after introduction of the expression construct so as to obtain transformed host cells capable of producing enzymes of the invention which are free of selection marker genes.

Expression of proteins in prokaryotes is often carried out with vectors containing constitutive or inducible promoters directing the expression of either fusion or non-fusion proteins. Fusion vectors add a number of amino acids to a protein encoded therein, e.g. to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein.

Vectors preferred for use in bacteria are for example disclosed in WO-A1-2004/074468, which are hereby enclosed by reference. Other suitable vectors will be readily apparent to the skilled artisan.

Vectors of the invention may be transformed into a suitable host cell as described herein to provide for expression of a polypeptide of the invention. Thus, in a further aspect the invention provides a process for preparing an enzyme according to the invention which comprises cultivating a host cell transformed or transfected with an expression vector encoding the enzyme, and recovering the expressed polypeptide.

A polynucleotide according to the invention encodes, when transformed into a proper host cell an enzyme according to the invention. The invention features cells, e.g., transformed host cells or recombinant host cells comprising a polynucleotide according to the invention or comprising a vector according to the invention. A "transformed host cell" or "recombinant host cell" is a cell into which a polynucleotide according to the invention has been introduced, by means of recombinant DNA techniques.

Both prokaryotic and eukaryotic cells are included, e.g., bacteria, fungi, yeast, insect, mammalian and the like. Preferably the host cell is a bacterium selected from the group of *Bacillus*, in particular *B. subtilis*, *B. amyloliquefaciens* or *B. licheniformis*: a *Escherichia*, in particular *E. coli*, or *Aspergillus*, in particular *A. Niger* or *A. oryzae* specie, or a fungal cell, i.e. a yeast cell, such as *Candida*, *Hansenula*, *Kluyveromyces*, *Pichia*, *Saccharomyces*, *Schizosaccharomyces*, or *Yarrowia* strain. Preferably the yeast cell is a *Kluyveromyces lactis*, *S. cerevisiae*, *Hansenula polymorpha*, *Yarrowia lipolytica*, *Pichia pastoris*, or a filamentous fungal cell. Filamentous fungi include all filamentous forms of the subdivision *Eumycota* and *Oomycota* (as defined by Hawksworth et al., In, Ainsworth and Bisby's Dictionary of The Fungi, 8th edition, 1995, CAB International, University Press, Cambridge, UK).

A host cell can be chosen which modifies and processes the encoded enzyme in a specific, desired fashion after translation. Such post translational modification (e.g., glycosylation) and processing (e.g., cleavage) of protein products may facilitate optimal functioning of the protein. Various host cells have characteristic and specific mechanisms for post-translational processing and modification of proteins and gene products. Appropriate cell lines or host systems familiar to those skilled in the art of molecular biology and/or microbiology can be chosen to ensure the desired and correct modification and processing of the foreign protein produced. E.g., in an embodiment a subtilisin BPN' variant or homologue thereof is initially secreted as a pre-pro-enzyme and the presence of the 77 amino acid pro sequence is important for in vivo production of mature subtilisin but has to be cleaved off to obtain full catalytic activity.

A method of producing an enzyme according to the invention typically comprises cultivating a recombinant host cell e.g. transformed or transfected with an expression vector under conditions to provide for expression of a coding sequence encoding the enzyme and recovering and purifying the produced enzyme from the cell or culture medium. Polynucleotides of the invention can be incorporated into a recombinant replicable vector, e.g. an expression vector or a replication vector. Transcription vectors are used to amplify their insert.

The purpose of a vector which transfers genetic information to another cell is typically to isolate, multiply, or express the insert in the target cell. Vectors called expression vectors (expression constructs) specifically are for the expression of the transgene in the target cell, and generally have a promoter sequence that drives expression of the transgene. Simpler vectors called transcription vectors are only capable of being transcribed but not translated: they can be replicated in a target cell but not expressed, unlike expression vectors. Transcription vectors are used to amplify their insert. Thus in a further embodiment, the invention provides a method of making a polynucleotide of the invention by introducing a polynucleotide of the invention into a replicable vector, introducing the vector into a compatible host cell, and growing the host cell under conditions which bring about the replication of the vector. The vector may be recovered from the host cell.

Preferably, the enzyme according to the invention is produced as a secreted protein in which case the nucleotide sequence encoding a mature form of the enzyme in the expression construct is operably linked to a nucleotide sequence encoding a signal sequence. Preferably the signal sequence is native (homologous), also referred to herein as "wild type" to the nucleotide sequence encoding the enzyme. Alternatively the signal sequence is foreign (heterologous) to the nucleotide sequence encoding the enzyme, in which case the signal sequence is preferably endogenous to the host cell in which the nucleotide sequence according to the invention is expressed. Examples of suitable signal sequences for bacilli can be found in "van Dijl, J. M. et al. 2001. In: Sonenshein, A. L., Hoch, J. A. and Losick, R., eds. *Bacillus subtilis* and its closest relatives: from genes to cells. Washington, D.C.: ASM Press, pp. 337-355" and "Degering C et al., Appl Environ Microbiol. 2010 October; 76(19): 6370-6."

Expression of heterologous proteins in yeast is well known. Sherman, F., et al., Methods in Yeast Genetics, Cold Spring Harbor Laboratory (1982) is a well recognized work describing the various methods available to express proteins in yeast. Vectors, strains, and protocols for expression in, e.g. *Saccharomyces* and *Pichia* are generally known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired. More specifically, suitable yeast signal sequences are those from yeast alfa-factor genes. Similarly, a suitable signal sequence for filamentous fungal host cells is e.g. a signal sequence from a filamentous fungal amyloglucosidase (AG) gene, e.g. the *A. niger* g/aA gene. This may be used in combination with the amyloglucosidase (also called (gluco) amylase) promoter itself, as well as in combination with other promoters. Hybrid signal sequences may also be used with the context of the present invention. Preferred heterologous secretion leader sequences are those originating from the fungal amyloglucosidase (AG) gene (g/aA-both 18 and 24 amino acid versions e.g. from *Aspergillus*), the [alpha]-factor gene (yeasts e.g. *Saccharomyces* and *Kluyveromyces*) or the [alpha]-amylase (amyE, amyQ and amyL) and alkaline protease aprE and neutral protease genes (*Bacillus*).

A heterologous host cell may also be chosen wherein the enzyme of the invention is produced in a form which is substantially free of enzymatic activities that might interfere with the applications, e.g. free from peptide degrading or modifying enzymes. In particular in the case of producing variants, the host cell should not produce any wild type enzyme. This may be achieved by choosing a host cell which does not normally produce such enzymes or by deliberately removing the corresponding genes by techniques known in the art.

The invention encompasses processes for the production of the enzyme of the invention by means of recombinant expression of a DNA sequence encoding the enzyme of the invention. For this purpose the DNA sequence of the invention can be used for gene amplification and/or exchange of expression signals, such as promoters, secretion signal sequences, in order to allow economic production of the enzyme in a suitable homologous or heterologous host cell. A homologous host cell is a host cell which is of the same species or which is a variant within the same species as the species from which the DNA sequence is obtained. The host cell may over-express the enzyme, and techniques for engineering over-expression are well known. The host may thus have two or more copies of the encoding polynucleotide (and the vector may thus have two or more copies accordingly). Therefore in one embodiment of the invention the recombinant host cell according to the invention is capable of expressing or overexpressing a polynucleotide or vector according to the invention.

Another aspect of the invention is a method for producing an enzyme of the invention comprising (a) culturing a recombinant host cell according to the invention under conditions such that the enzyme of the invention is produced; and (b) optionally recovering the enzyme of the invention from the cell culture medium. For each combination of a promoter and a host cell, culture conditions are available which are conducive to the expression the DNA sequence encoding the enzyme. After reaching the desired cell density or titre of the enzyme the culture is stopped and the enzyme is recovered. The term "culturing" includes maintaining and/or growing a living recombinant host cell of the present invention, in particular the recombinant host cell according to the invention.

In one aspect, a recombinant host cell of the invention is cultured in liquid media. In another aspect, a recombinant host cell is cultured in solid media or semi-solid media. Preferably, the recombinant host cell of the invention is cultured in liquid media comprising nutrients essential or beneficial to the maintenance and/or growth of the recombinant host cell. The recombinant host cells may be cultured in liquid media either continuously or intermittently, by conventional culturing methods such as standing culture, test tube culture, shaking culture, aeration spinner culture or fermentation. Preferably, the recombinant host cells are cultured in a fermentor. Fermentation processes of the invention include batch, fed-batch and continuous methods of fermentation. A variety of such processes have been developed and are well known in the art.

The recombinant host cells are preferably cultured under controlled pH. In one embodiment, recombinant host cells may be cultured at a pH of between 4.5 and 8.5, preferably 6.0 and 8.5, more preferably at a pH of about 7. The desired pH may be maintained by any method known to those skilled in the art.

Preferably, the recombinant host cells are further cultured under controlled aeration and under controlled temperatures. In one embodiment, the controlled temperatures include temperatures between 15 and 70° C., preferably the temperatures are between 20 and 55° C., more preferably between 30 and 50° C. The appropriate conditions are usually selected based on the choice of the expression host and the protein to be produced.

In a specific embodiment, the enzyme is expressed in Bacillus strain GX4935 (see examples). The strain is cultivated under aerobic conditions in a suitable fermentation medium. A suitable medium medium may contain assimilable sources of carbon and nitrogen besides inorganic salts optionally together with growth promoting nutrients, such as yeast extract. Fermentation is typically conducted at 35-40° C. and at a pH of 6.5-7.5 and preferably kept approximately constant by automatic means. The enzyme is excreted into the medium. At the end of fermentation, if required, the production host may be killed by means known by the person skilled in the art. The ensuing fermentation broth may be freed of bacterial cells, debris therefrom together with other solids, for example by filtration or centrifugation. The filtrate or supernatant containing the enzyme may be further clarified, for example by filtration or centrifugation, and then concentrated as required, for example by ultrafiltration or in an evaporator under reduced pressure to give a concentrate which, if desired, may be taken to dryness, for example by lyophilization or spray-drying.

After fermentation, if necessary, the cells can be removed from the fermentation broth by means of centrifugation or filtration. After fermentation has stopped or after removal of the cells, the enzyme of the invention may then be recovered and, if desired, purified and isolated by conventional means, including, but not limited to, treatment with a conventional resin, treatment with a conventional adsorbent, alteration of pH, solvent extraction, dialysis, filtration, concentration, crystallization, recrystallization, pH adjustment, lyophilisation and the like. For example, the enzymes according to the invention can be recovered and purified from recombinant cell cultures by methods known in the art (Protein Purification Protocols, Methods in Molecular Biology series by Paul Cutler, Humana Press, 2004). Usually, the compound is "isolated" when the resulting preparation is substantially free of other components.

In an embodiment, an isolated enzyme preparation is provided having a purity of about 80% (by dry weight) of the enzyme of the invention or more (i.e. less than about 20% of all the media, components or fermentation byproducts). In a specific embodiment, the invention provides the enzyme of the invention in a purity of about 90% or more, preferably in a purity of 95% or more, in particular in a purity of 98% or more. In practice, a minor amount of other components may be present in an isolated enzyme preparation of the invention. Thus, a purified preparation of the enzyme may comprise 99% or less of the enzyme, in particular 98% or less.

Alternatively, however, the enzyme of the invention is not purified from the recombinant host cell or the culture. The entire culture or the culture supernatant may be used as a source of the enzyme. In a specific embodiment, the culture or the culture supernatant comprising the enzyme is used without substantial modification.

It is further noted that it is also possible to make the enzyme of the invention, such as the subtilisin BPN' variant, by known chemical protein synthesis technology, e.g. by solid phase peptide synthesis. However, expression of the subtilisin mutants in microbial host cells will generally be preferred since this will allow for the microbial host cell to produce the subtilisin protein in a proper conformation for enzymatic activity. However, it should be possible to convert improperly folded subtilisin BPN' variants or homologues thereof into an active conformation.

The enzymes of the invention (subtilisin BPN' variants or homologues thereof) may be chemically or biochemically modified, e.g. post-translationally modified. For example, they may be glycosylated or comprise modified amino acid residues. They may also be modified by the addition of a tag, as already mentioned above. Such modified polypeptides and proteins fall within the scope of the term "enzyme" of the invention.

A more detailed description of suitable and preferred subtilisin BPN' variants or homologues thereof, their production, and their use is described in PCT/NL2014/050707 (to Enzypep B.V. having an application date of 10 Oct. 2014) and WO 2016/056913. The contents of these applications are incorporated herein by reference, in particular the parts relating to amino acid sequences of the subtilisin BPN' variant or homologue, especially PCT/NL2014/050707 page 21, line 1 till page 25, line 3; their production, especially page 26, line 17 till page 37, line 21, FIG. 14, and the Examples, page 37, line 25 page 40, line 21; and their use, in particular Examples 1-23, respectively the following parts of WO2016/056913: page 24, line 7 till page 29, line 3 (relating to the subtilisin BPN' variants or homologues); especially page 30, line 17 till page 41, line 21 (their production), FIG. 14, and the Examples, page 41, line 25 page 44, line 21; and their use, in particular Examples 1-27. Further, in particular, incorporated herein are definitions for terms given in PCT/NL2014/050707 or WO 2016/056913 and not provided in the present text.

In order to further illustrate the present invention and the advantages thereof, the following specific examples are given, it being understood that the same is intended only as illustrative and in nowise limitative.

EXAMPLES

Production of Enzymes (for Use) According to the Invention
Mutagenesis, Cloning and Expression The gene coding for subtilisin BS 149 (Ruan et al. 2008) was obtained from Philip N. Bryan (University of Maryland Biotechnology Institute, 9600 Gudelsky Drive, Rockville, Md. 20850). Mutagenesis was performed using a pUB110 based Escherichia. coli-Bacillus subtilis (E. coli-B. subtilis) shuttle vector harboring the BS149 gene using either the native promotor or alternatively using the aprE promotor and optionally a C-terminal his-tag (pBE-S DNA, http://www.clontech.com/takara). The gene encoding an enzyme according to the invention was constructed by introducing the mutations S221C and P225A into the BS149 gene using the site-directed mutagenesis method (Sambrook et al., 1989). All primers were designed using the Agilent Primer design tool (http://www.genomics.agilent.com). The constructed sequences were verified by DNA sequencing before transformation to Bacillus subtilis GX4935.

The gene coding for BS149-DM with a His-tag was cloned into a pUB-110 based E. coli-B. subtilis shuttle vector (pBES) using the MluI and BamHI site (FIG. 1). The polynucleotide sequence of a gene (BS149-DM) encoding an enzyme (polypeptide) of the invention and the encoded enzyme is shown in SEQUENCE ID NO 5. The corresponding amino acid sequence is numbered according to the subtilisin BPN' numbering scheme. Amino acids −107 to −1 comprise the signal sequence, the pre sequence and a pro sequence which are cleaved off upon full maturation. Amino acids 1-275 comprise the mature enzyme which exhibits the full catalytic activity. In order to enable a fast and efficient purification after amino acid 275 a C-terminal His-tag is attached as shown in SEQUENCE ID NO 5. As a consequence of the removal of a calcium binding site BS149-DM contains a deletion of 9 amino acids compared to subtilisin BPN' comprising the amino acids corresponding to L75, N76, N77, S78, I79, G80, V81, L82 and G83 in subtilisin BPN'. In order to maintain the subtilisin BPN' numbering for BS149-DM the numbering jumps from 74 to 83. In the shuttle vector, the expression of the gene is under the control of aprE promoter. The vector contained the pUB ori of replication for Bacillus and a kanamycin resistance marker. The vector also contained the ColE1 ori of replication and an ampicillin resistance marker for maintenance in E. coli. The resulting plasmid pBES-BS149DMHIS was propagated in E. coli TOP10 and transformed into B. subtilis GX4935 (ΔnprEΔaprE).). Using pBES-BS149DMHIS as the template, mutagenesis was carried out by the Quikchange method (Agilent). Alternatively other methods for site directed mutagenesis known in the art may be used (Sambrook et al., 1989.).

Production and Purification of Synthetic Subtilisin BPN' Variants which Carry a His-Tag:

A single microbial colony of B. subtilis containing a plasmid with the subtilisin variant gene of interest was inoculated in 5 mL LB with kanamycin (10 μg/mL) at 37° C. in a shaking incubator. To the 30 mL Terrific Broth supplemented with antibiotic (kanamycin 10 μg/mL) and amino acids (100 mg/L Trp, 100 mg/L Met and 100 mg/L Lys) 0.6 mL of the overnight culture was added. The cells were grown 48 h at 37° C. in a shaking incubator (200 rpm). The cells were harvested by centrifugation (15 min, 4,000 rpm, 4° C.). The medium (30 mL) was decanted and concentrated on Amicon-centrifugal unit (15 ml, 10 kDa MW cut-off) in two centrifugation steps (15 min, 4000 rpm, 4° C.). The concentrated medium (0.5 ml) was then exchanged for buffer A (25 mM Tricine, pH 7.5, 0.5M NaCl, 20 mM imidazole) in three washing/concentrating steps (14 ml buffer A, 10 min, 4,000 rpm, 4° C.). For His-tag purification Talon resin (2.5 ml, Clonetech) was added to a plastic column cartridge. The resin was washed with 5 mL MilliQ water and equilibrated with 5 mL of buffer A. The crude enzyme was loaded on the column and washed with 5 mL buffer A. The enzyme was eluted with 5 mL buffer B (25 mM Tricine, pH 7.5, 0.5M NaCl, 200 mM imidazole). The elute was concentrated on a Amicon-centrifugal unit (5 ml, 10 kDa MW cut-off) by centrifugation (15 min, 4000 rpm, 4° C.) and the buffer was exchanged to 25 mM Tricine, pH 7.5 in three washing/concentrating steps (5 ml buffer, 10 min, 4,000 rpm, 4° C.).

The purity and enzyme concentration was determined as described above Purity was more than 90%, The obtained aqueous solution (25 mM Tricine, pH 7.5) containing about 2 mg/ml of the obtained enzyme was used as such for the oligopeptide fragment condensations and cyclisations.

REFERENCES

Abrahmsén, L, J Tom, J Burnier, K A Butcher, A Kossiakoff, and J A Wells. 1991. "Engineering Subtilisin and Its Substrates for Efficient Ligation of Peptide Bonds in Aqueous Solution." Biochemistry 30 (17) (April 30): 4151-9. http://www.ncbi.nlm.nih.gov/pubmed/2021606.

Fahnestock S R, Fisher K E: Expression of the staphylococcal protein A gene in Bacillus subtilis by gene fusions utilizing the promoter from a Bacillus amyloliquefaciens alpha-amylase gene. J Bacteriol. 1986 March; 165(3): 796-804

Kawamura, Fujio, and Roy H. Doi. Construction of a Bacillus subtilis double mutant deficient in extracellular alkaline and neutral proteases. J Bacteriol. 1984 October; 160(1):442-4

Ruan, Biao, Viktoriya London, Kathryn E Fisher, D Travis Gallagher, and Philip N Bryan. Engineering substrate preference in subtilisin: structural and kinetic analysis of a specificity mutant. Biochemistry. 2008 Jun. 24; 47(25): 6628-36.

Sambrook J, Fritsch E F, Maniatis T. 1989. Molecular Cloning: A Laboratory Manual. 2nd edition. Cold Spring Harbor Laboratory Press, Cold Spring Harbor, N.Y.

Wells, James A, Eugenio Ferrari, Dennis J Henner, David A Estell, and Ellson Y Chen. Cloning, sequencing, and secretion of Bacillus amyloliquefaciens subtilisin in Bacillus subtilis. Nucleic Acids Res. 1983 Nov. 25; 11(22):7911-25.

Hydrolysis, Ligation and Cyclisation Examples

Materials and Methods

Unless stated otherwise, chemicals were obtained from commercial sources and used without further purification. Analytical HPLC was performed on an HP 1090 Liquid Chromatograph, using a reversed-phase column (Phenomenex, C18, 5 μm particle size, 150×4.6 mm) at 40° C. UV detection was performed at 220 nm using a UV-VIS 204 Linear spectrometer. The gradient program was: 0-25 min linear gradient ramp from 5% to 98% eluent B and from 25.1-30 min 5% eluent B (eluent A: 0.5 mL/L methane sulfonic acid (MSA) in $H_2O$, eluent B 0.5 mL/L MSA in acetonitrile). The flow was 1 mL/min from 0-25.1 min and 2 mL/min from 25.2-29.8 min, then back to 1 mL/min until stop at 30 min. Injection volumes were 20 μL. Preparative HPLC was performed on a Varian PrepStar system using a stationary-phase column (Pursuit XRs, C18, 10 μm particle size, 500×41.4 mm). LC-MS was performed on an Agilent 1200 series Liquid Chromatograph, using a reversed-phase column (Phenomenex, C18, 5 μm particle size, 150×4.6 mm) at 40° C. UV detection and gradient program were as described for analytical HPLC. The molecular weights were determined using an Agilent 6130 quadrupole LC/MS system.

Protocol 1: Oligopeptide-OCam-Leu-OH Esters were Synthesized as Described Below:

1 gram of Fmoc-Leu-Wang resin (with a loading of 0.72 mmol/gram) was washed with DCM (2×2 min, 10 mL) and DMF (2×2 min, 10 mL) and Fmoc-deprotected using piperidine/DMF (1/4, v/v, 2×8 min, 10 mL). After washing with DMF (2×2 min, 10 mL), DCM (2×2 min, 10 mL) and DMF (2×2 min, 10 mL), iodoacetic acid (4 equiv.) was coupled to the resin using DCC (4 equiv.) and HOAt (4 equiv.) in DCM (45 min, 10 mL). After washing with DMF (2×2 min, 10 mL), DCM (2×2 min, 10 mL) and THF (2×2 min, 10 mL), the resin was loaded with an Fmoc-protected amino acid using 4 equiv. Fmoc-Xxx-OH and 10 equiv. DiPEA in DMF/THF (1/1, v/v, 10 mL) at 50° C. for 20 h. Here and in other parts of this disclosure 'Xxx' stands for one amino acid (variable as indicated in the Figures belonging to the examples below).

After washing with DMF (2×2 min, 10 mL), DCM (2×2 min, 10 mL) and DMF (2×2 min, 10 mL), standard SPPS protocols were followed to elongate the peptide (Weng C. Chan and Peter White, OUP Oxford, 2000). Cleavage from the resin and side-chain deprotection was performed using a mixture of trifluoroacetic acid (TFA), triisopropylsilane (TIS) and water (95/2.5/2.5, v/v/v, 15 mL) for 120 min. The crude peptide was precipitated using methyl tert-butyl ether (MTBE)/n-heptanes (1/1, v/v, 50 mL). The precipitated peptide was collected by centrifugation and washed twice with MTBE/n-heptanes (1/1, v/v, 50 mL) followed by lyophilization from acetonitrile/water (1/1, v/v, 50 mL).

Protocol 2: Oligopeptide C-Terminal Amide Nucleophiles were Synthesized as Described Below:

1 gram of Rink resin (4-((2,4-dimethoxyphenyl)(Fmoc-amino)methyl)-phenoxyalkyl linker, with a loading of 0.64 mmol/gram) was washed with DCM (2×2 min, 10 mL) and DMF (2×2 min, 10 mL) and Fmoc-deprotected using piperidine/DMF (1/4, v/v, 2×8 min, 10 mL). Standard SPPS protocols were followed to elongate the peptide (Weng C. Chan and Peter White, OUP Oxford, 2000). Cleavage from the resin and side-chain deprotection was performed using a mixture of TFA/TIS/water (95/2.5/2.5, v/v/v, 15 mL) for 120 min. The crude peptide was precipitated using MTBE/n-heptanes (1/1, v/v, 50 mL). The precipitated peptide was collected by centrifugation and washed twice with MTBE/n-heptanes (1/1, v/v, 50 mL) followed by lyophilization from acetonitrile/water (1/1, v/v, 50 mL).

Protocol 3: N-Acetyl-Protected Oligopeptide Activated Esters were Synthesized as Described Below:

After SPPS of the desired sequence according to one of the protocols 1, the resin bound peptide was Fmoc-deprotected using piperidine/DMF (1/4, v/v, 2×8 min, 10 mL). The resin was washed with DMF (2×2 min, 10 mL), DCM (2×2 min, 10 mL) and DMF (2×2 min, 10 mL) and the peptide N-terminal amine function was acetylated using a mixture of $Ac_2O$ (10 vol %), DiPEA (5 vol %), HOBt (0.2 wt %) in DMF (2×10 min, 10 mL). The resin was washed with DMF (3×2 min, 10 mL) and DCM (3×2 min, 10 mL). Cleavage from the resin and side-chain deprotection was performed using a mixture of TFA/TIS/water (95/2.5/2.5, v/v/v, 15 mL) for 120 min. The crude peptide was precipitated using MTBE/n-heptanes (1/1, v/v, 50 mL). The precipitated peptide was collected by centrifugation and washed twice with MTBE/n-heptanes (1/1, v/v, 50 mL) followed by lyophilization from acetonitrile/water (1/1, v/v, 50 mL).

Protocol 4: Oligopeptide C-Terminal Acids were Synthesized as Described Below:

1 gram of Trityl resin (2-chloro-chlorotrityl linker, with a loading of 1.0 mmol/gram) was washed with DCM (2×2 min, 10 mL) and Fmoc-Xxx-OH (2 equiv.) was coupled to the resin using DiPEA (5 equiv.) in DCM (30 min, 10 mL). After washing with DMF (2×2 min, 10 mL), the unreacted chlorotrityl groups were capped using DCM/MeOH/DiPEA (80/15/5, v/v/v, 2×10 min, 10 mL). The resin was washed with DMF (2×2 min, 10 mL), DCM (2×2 min, 10 mL) and DMF (2×2 min, 10 mL) and standard SPPS protocols were followed to elongate the peptide (Weng C. Chan and Peter White, OUP Oxford, 2000). Cleavage from the resin and side-chain deprotection was performed using a mixture of TFA/TIS/water (95/2.5/2.5, v/v/v, 15 mL) for 120 min. The crude peptide was precipitated using MTBE/n-heptanes (1/1, v/v, 50 mL). The precipitated peptide was collected by centrifugation and washed twice with MTBE/n-heptanes (1/1, v/v, 50 mL) followed by lyophilization from acetonitrile/water (1/1, v/v, 50 mL).

Coupling Examples

Note: The enzyme denoted as BS149-DM (SEQUENCE ID NO:5) contains a deletion of amino acids 75-83 and mutations Q2K, S3C, P5S, S9A, 131L, K43N, M50F, A73L, E156S, G166S, G169A, S188P, Q206C, N212G, Y217L, N218S, S221C, P225A, T254A and Q271E compared to SEQUENCE ID NO:2. On the basis of the present disclosure, common general knowledge and optionally a limited amount of route testing, the skilled person in the art may revert one or more of mutations Q2K, S3C, P5S, S9A, 131L, K43N, M50F, A73L, E156S, G166S, G169A, S188P, Q206C, N212G, Y217L, N218S, T254A and Q271E or make different substitutions at one or more of the positions Q2, S3, P5, S9, 131, K43, M50, A73, E156, G166, G169, S188, Q206, N212, N218S, T254, Q271.

The enzymes of the invention used in the Examples have all the mutations of BS149-DM, plus optional additional mutations as mentioned in the Examples.

As indicated below, enzymes with further mutations were made using the technology described above.

Example 1: Determining the S/H Ratios of 2 Pairs of Serine Endoproteases and their Corresponding Ligases To determine the S/H ratio of the different enzymes, the following standard reaction was performed. 800 μL of phosphate buffer (100 mM, pH 8.0) was added to a mixture of 100 μL tripeptide C-terminal amide stock solution (0.01 mmol H-Ala-Leu-Arg-$NH_2$.2TFA in 300 μL water) and 100 μL pentapeptide C-terminal Cam-ester stock solution (0.01 mmol Ac-Asp-Phe-Ser-Lys-Leu-OCam.TFA in 1200 μL water). To this mixture 5.5 μg enzyme was added and the reaction mixture was shaken (150 rpm) at room temperature. After 30 min a 500 μL aliquot of the reaction mixture was withdrawn and quenched with 500 μL MSA/water (1/99, v/v) and analyzed by LC-MS. The product, hydrolysed pentapeptide C-terminal Cam-ester and remaining pentapeptide C-terminal Cam-ester peaks were integrated.

The S/H ratio of the different enzymes is defined as the amount of product divided by the amount of hydrolysed pentapeptide C-terminal Cam-ester, within the specified time. In the following Table S/H ratios are given for several subtilisin BPN' variants.

| Enzyme | S/H ratio |
| --- | --- |
| BS149-DM | 1.8 |
| BS149-DM + C221S | 0.0015 |
| BS149-DM + L217H + M222P | 4.1 |
| BS149-DM + L217H + C221S + M222P | 0.019 |

Example 2: Identification of Oligopeptide Fragments Suitable for the Enzymatic Synthesis of Thymosin-α-1, Using BS149-DM+C221S as the Endoprotease 1 mg of Thymosin-α-1 (Ac-$Ser^1$-$Asp^2$-$Ala^3$-$Ala^4$-$Val^5$-$Asp^6$-$Thr^7$-$Ser^8$-$Ser^9$-$Glu^{10}$-$Ile^{11}$-$Thr^{12}$-$Thr^{13}$-$Lys^{14}$-$Asp^{15}$-$Leu^{16}$-$Lys^{17}$-$Glu^{18}$-$Lys^{19}$-$Lys^{20}$-$Glu^{21}$-$Val^{22}$-$Val^{23}$-$Glu^{24}$-$Glu^{25}$-$Ala^{26}$-$Glu^{27}$-$Asn^{28}$-OH) was dissolved in 1 mL of phosphate buffer (1N, pH8). To this solution 10 μL of BS149-DM+C221S (2.0 mg/mL) was added and the mixture was analyzed by LC-MS every 30 minutes. After mass analysis of the different fragments observed by LC-MS it was shown that Thymosin-α-1 was preferably cleaved into two fragments, i.e. Ac-$Ser^1$-$Asp^2$-$Ala^3$-$Ala^4$-$Val^5$-$Asp^6$-$Thr^7$-$Ser^8$-$Ser^9$-$Glu^{10}$-$Ile^{11}$-$Thr^{12}$-$Thr^{13}$-$Lys^{14}$-OH (Ac-1-14-OH, with a mass of 1465.7) and H-$Asp^{15}$-$Leu^{16}$-$Lys^{17}$-

Figure 2:
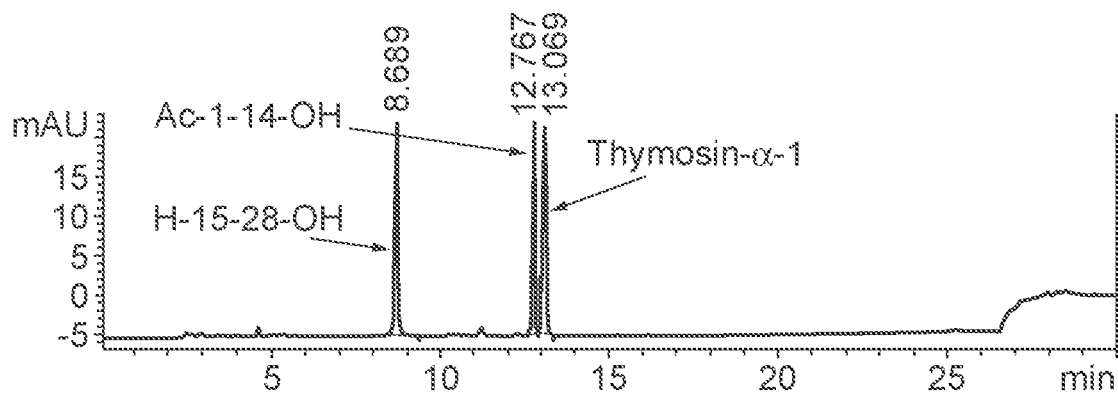
FIG. 2: Hydrolysis of Thymosin-alpha-1 using BS149-DM+C221S endoprotease mutant, reaction mixture after 90 min.

Glu$^{18}$-Lys$^{19}$-Lys$^{20}$-Glu$^{21}$-Val$^{22}$-Val$^{23}$-Glu$^{24}$-Glu$^{25}$-Ala$^{26}$-Glu$^{27}$-Asn$^{28}$-OH (H-15-28-OH, with a mass of 1658.8), For the HPLC chromatogram after 90 min. see FIG. 2.

Example 3: Synthesis of Thymosin-α-1 Using BS149-DM+M222G+L217R as the Ligase

The fragments identified in Example 2, were used for the synthesis design for Thymosin-α-1.

Figure 3:
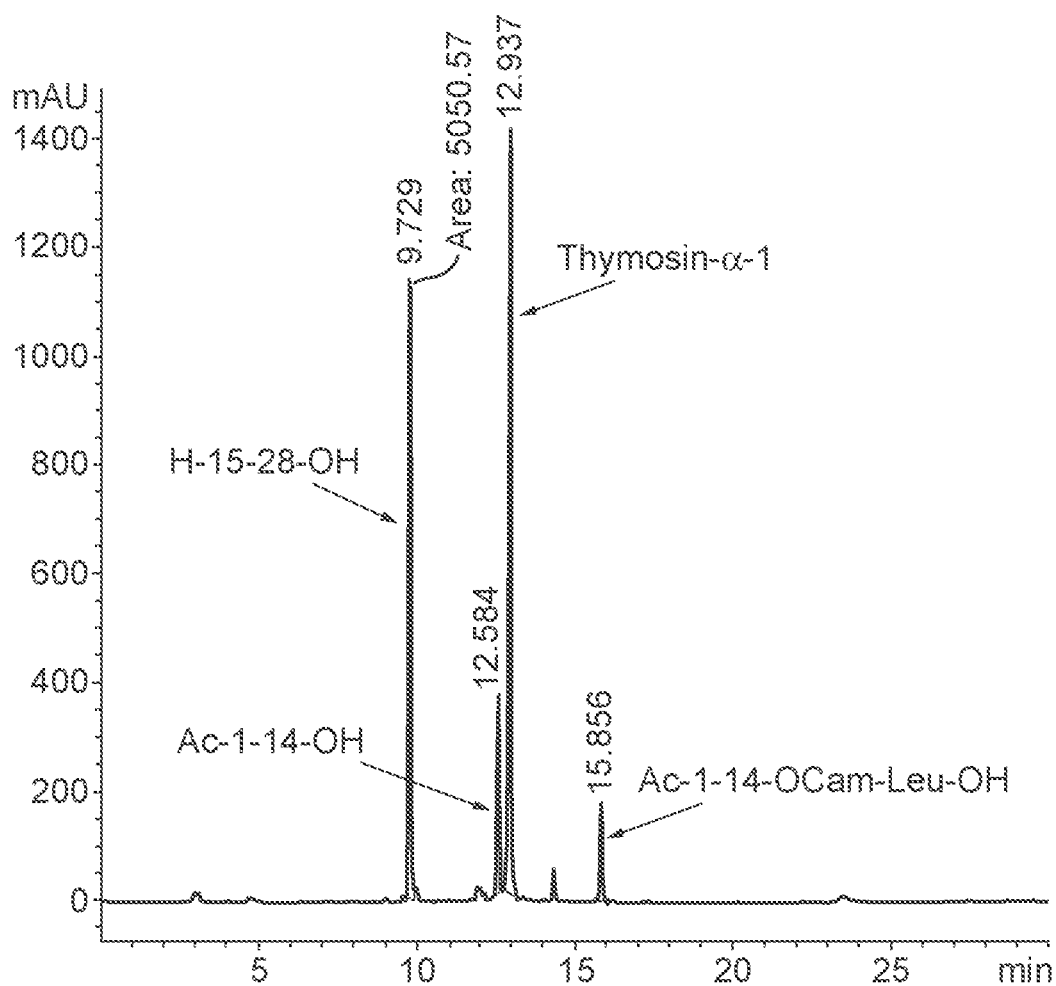
FIG. 3: Synthesis of Thymosin-alpha-1 using BS149-DM+M222G+L217R ligase mutant, reaction mixture after 90 min.

53 mg of Ac-Ser$^1$-Asp$^2$-Ala$^3$-Ala$^4$-Val$^5$-Asp$^6$-Thr$^7$-Ser$^8$-Ser$^9$-Glu$^{10}$-Ile$^{11}$-Thr$^{12}$-Thr$^{13}$-Lys$^{14}$-OCam-Leu-OH.TFA (Ac-1-14-OCam-Leu-OH) and 78 mg of H-Asp$^{15}$-Leu$^{16}$-Lys$^{17}$-Glu$^{18}$-Lys$^{19}$-Lys$^{20}$-Glu$^{21}$-Val$^{22}$-Val$^{23}$-Glu$^{24}$-Glu$^{25}$-Ala$^{26}$-Glu$^{27}$-Asn$^{28}$-OH.4TFA (H-15-28-OH) were dissolved in 2 mL phosphate buffer (1N, pH 8) and the pH was adjusted to pH 8.1 using aqueous NaOH (5N). 0.5 mL of BS149-DM+M222G+L217R (2 mg/mL) was added and the reaction mixture was shaken (200 rpm) at ambient temperature. After 90 minutes an aliquot of 20 μL was quenched with 0.5 mL MSA/water (1/9, v/v) and analysed by LC-MS, see the HPLC diagram in FIG. 3. Clearly, Thymosin-α-1 was formed as the main product (79%). A side reaction, i.e. the enzymatic hydrolysis of the Cam-ester, is indicated as Ac-1-14-OH.

Conclusion: clearly, it is possible to design an enzymatic process for Thymosin-α-1 from two fragments using the ligase BS149-DM+M222G+L217R with the coupling position having been identified by hydrolysis of Thymosin-α-1 using the serine endoprotease BS149-DM+C221S (Example 2).

Example 4: Identification of Oligopeptide Fragments Suitable for the Enzymatic Synthesis of Exenatide, Using BS149-DM+C221S as the Endoprotease 1 mg of Exenatide (H-His$^1$-Gly$^2$-Glu$^3$-Gly$^4$-Thr$^5$-Phe$^6$-Thr$^7$-Ser$^8$-Asp$^9$-Leu$^{10}$-Ser$^{11}$-Lys$^{12}$-Gln$^{13}$-Met$^{14}$-Glu$^{15}$-Glu$^{16}$-Glu$^{17}$-Ala$^{18}$-Val$^{19}$-Arg$^{20}$-Leu$^{21}$-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser$^{39}$-NH$_2$) was dissolved in 1 mL of phosphate buffer (1N, pH8). To this solution 10 μL of BS149-DM+C221S (2.0 mg/mL) was added and the mixture was analyzed by LC-MS every 30 minutes. After mass analysis of the different fragments observed by LC-MS it was shown that Exenatide was preferentially cleaved into three fragments, i.e.:

H-His$^1$-Gly$^2$-Glu$^3$-Gly$^4$-Thr$^5$-Phe$^6$-Thr$^7$-Ser$^8$-Asp$^9$-Leu$^{10}$-Ser$^{11}$-Lys$^{12}$-Gln$^{13}$-OH,

H-Met$^{14}$-Glu$^{15}$-Glu$^{16}$-Glu$^{17}$-Ala$^{18}$-Val$^{19}$-Arg$^{20}$-Leu$^{21}$-Phe$^{22}$-Ile$^{23}$-Glu$^{24}$-OH, and H-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser$^{39}$-NH$_2$ On the basis of these results it was determined to use H-His$^1$-Gly$^2$-Glu$^3$-Gly$^4$-Thr$^5$-Phe$^6$-Thr$^7$-Ser$^8$-Asp$^9$-Leu$^{10}$-Ser$^{11}$-Lys$^{12}$-Gln$^{13}$-Met$^{14}$-Glu$^{15}$-Glu$^{16}$-Glu$^{17}$-Ala$^{18}$-Val$^{19}$-Arg$^{20}$-Leu$^{21}$-Phe$^{22}$-Ile$^{23}$-Glu$^{24}$-OCam-Leu-OH.3TFA (a combination of the first two fragments mentioned in the previous paragraph) as the first fragment (C-terminal ester) and H-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser$^{39}$-NH$_2$.2TFA as the second fragment (oligopeptide nucleophile having an N-terminally unprotected amine) in the design of an enzymatic peptide synthesis process according to the invention. Example 5 shows a reduction to practice of the designed process.

Example 5: Synthesis of Exenatide from Two Fragments Using BS149-DM as the Ligase The following two fragments identified in Example 4, were used to synthesise Exenatide: 3.3 mg of H-His$^1$-Gly$^2$-Glu$^3$-Gly$^4$-Thr$^5$-Phe$^6$-Thr$^7$-Ser$^8$-Asp$^9$-Leu$^{10}$-Ser$^{11}$-Lys$^{12}$-Gln$^{13}$-Met$^{14}$-Glu$^{15}$-Glu$^{16}$-Glu$^{17}$-Ala$^{18}$-Val$^{19}$-Arg$^{20}$-Leu$^{21}$-Phe$^{22}$-Ile$^{23}$-Glu$^{24}$-OCam-Leu-OH. 3TFA and 2.5 mg of H-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser$^{39}$-NH$_2$.2TFA were dissolved in 100 μL phosphate buffer (1N, pH 8) and the pH was adjusted to pH 8.1 using aqueous NaOH (5N). 5 μL of BS149-DM (2.1 mg/mL) was added and the reaction mixture was shaken (200 rpm) at ambient temperature. After 90 minutes the reaction mixture was quenched with 2 mL MSA/water (1/9, v/v) and analysed by LC-MS. The Cam-ester starting material, hydrolysed Cam-ester and Exenatide product peaks were integrated. The amount of Exenatide product was 83%.

Conclusion: clearly, it is possible to design an enzymatic process for Exenatide from two fragments using the ligase BS149-DM with the coupling position having been identified by hydrolysis of Exenatide using the endoprotease BS149-DM+C221S (Example 4).

Example 6: Identification of Oligopeptide Fragments Suitable for the Enzymatic Synthesis of Exenatide Using BS149-DM+L217H+C221S+M222P as the Endoprotease 1 mg of Exenatide (H-His$^1$-Gly$^2$-Glu$^3$-Gly$^4$-Thr$^5$-Phe$^6$-Thr$^7$-Ser$^8$-Asp$^9$-Leu$^{10}$-Ser$^{11}$-Lys$^{12}$-Gln$^{13}$-Met$^{14}$-Glu$^{15}$-Glu$^{16}$-Glu$^{17}$-Ala$^{18}$-Val$^{19}$-Arg$^{20}$-Leu$^{21}$-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser$^{39}$-NH$_2$) was dissolved in 1 mL of phosphate buffer (1N, pH8). To this solution 20 μL of BS149-DM+L217H+C221S+M222P (0.7 mg/mL) was added and the mixture was analyzed by LC-MS every 30 minutes. After mass analysis of the different fragments observed by LC-MS it was shown that Exenatide was preferentially cleaved into three fragments, i.e.

H-His$^1$-Gly$^2$-Glu$^3$-Gly$^4$-Thr$^5$-Phe$^6$-Thr$^7$-Ser$^8$-Asp$^9$-Leu$^{10}$-Ser$^{11}$-Lys$^{12}$-Gln$^{13}$-Met$^{14}$-Glu$^{15}$-Glu$^{16}$-Glu$^{17}$-Ala$^{18}$-Val$^{19}$-Arg$^{20}$-Leu$^{21}$-OH,

H-Phe$^{22}$-Ile$^{23}$-Glu$^{24}$-OH and H-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$.-Pro$^{37}$-Pro$^{38}$-Ser$^{39}$-NH$_2$ Conclusion: When hydrolyzing Exenatide with enzymes exhibiting a different substrate scope, another cleavage pattern is observed.

On the basis of these results it was determined to use H-His$^1$-Gly$^2$-Glu$^3$-Gly$^4$-Thr$^5$-Phe$^6$-Thr$^7$-Ser$^8$-Asp$^9$-Leu$^{10}$-Ser$^{11}$-Lys$^{12}$-Gln$^{13}$-Met$^{14}$-Glu$^{15}$-Glu$^{16}$-Glu$^{17}$-Ala$^{18}$-Val$^{19}$-Arg$^{20}$-Leu$^{21}$-OCam-Leu-OH (the first fragment mentioned in the previous paragraph) as the first fragment (C-terminal ester) and H-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser$^{39}$-NH$_2$.2TFA (a combination of the last two fragments mentioned in the previous paragraph) as the second fragment (oligopeptide nucleophile having an N-terminally unprotected amine) in the design of an enzymatic peptide synthesis process according to the invention. Example 7 shows a reduction to practice of the designed process.

Figure 4:
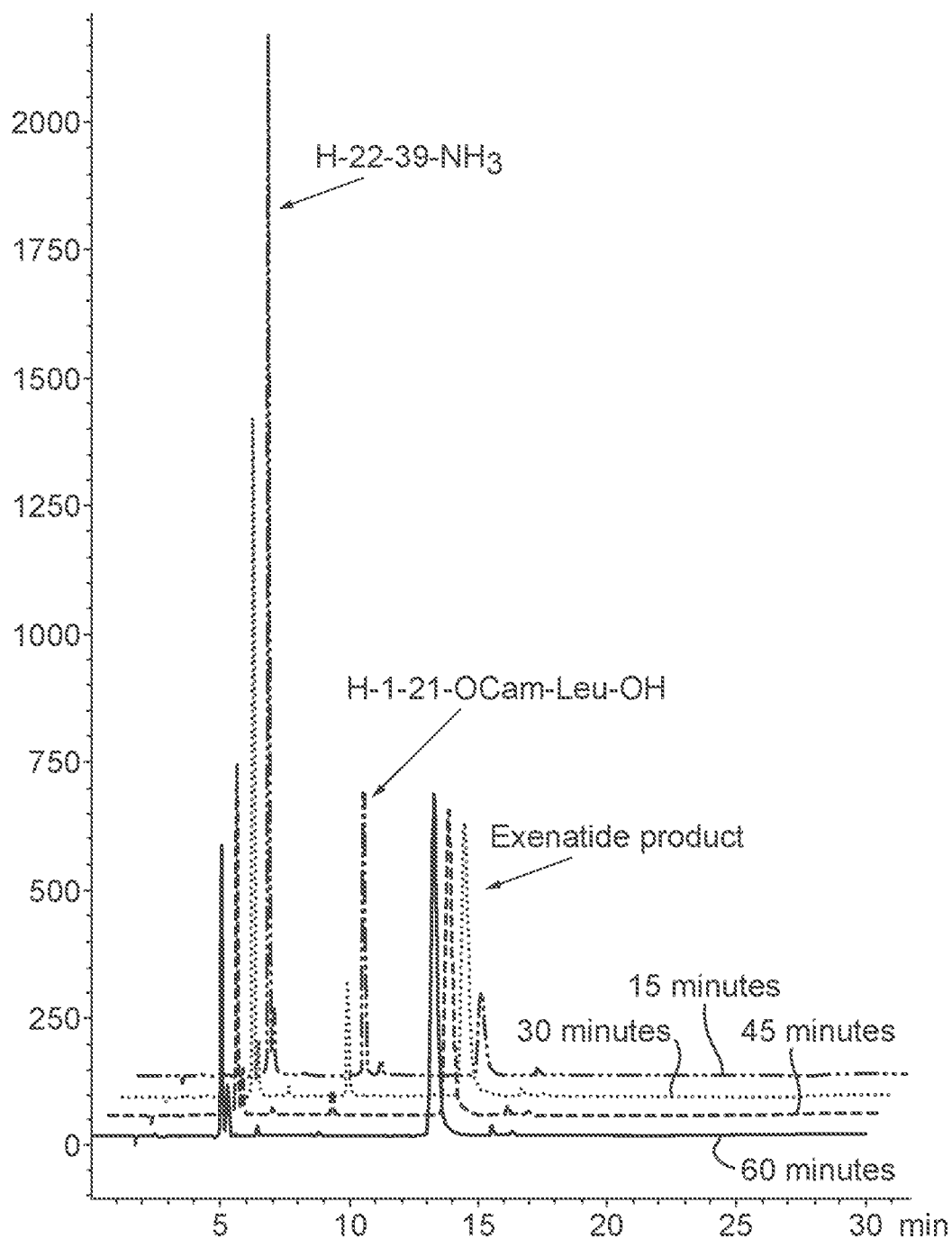
FIG. 4: Enzymatic synthesis of Exenatide using BS149-DM+L217H+M222P ligase mutant.

Example 7: Synthesis of Exenatide from two fragments using BS149-DM+L217H+M222P as the ligase 573.8 mg of H-His$^1$-Gly$^2$-Glu$^3$-Gly$^4$-Thr$^5$-Phe$^6$-Thr$^7$-Ser$^8$-Asp$^9$-Leu$^{10}$-Ser$^{11}$-Lys$^{12}$-Gln$^{13}$-Met$^{14}$-Glu$^{15}$-Glu$^{16}$-Glu$^{17}$-Ala$^{18}$-Val$^{19}$-Arg$^{20}$-Leu$^{21}$-OCam-Leu-OH.4TFA (H-1-21-OCam-Leu-OH) and 434.3 mg of H-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser$^{39}$-NH$_2$.2TFA (H-22-39-NH$_2$) were dissolved in 25 mL phosphate buffer (1N, pH 8) and the pH was adjusted to pH 8.1 using aqueous NaOH (5N). 4 mL of BS149-DM+L217H+M222P (0.4 mg/mL) was added and the reaction mixture was shaken (200 rpm) at ambient temperature. Aliquots of 20 μL were withdrawn after 15, 30, 45 and 60 minutes and quenched with 0.5 mL MSA/water (1/9, v/v) and analysed by LC-MS (FIG. 4). The synthesis of Exenatide was very successful (87% yield).

Conclusion: clearly, it is possible to design an enzymatic process for Exenatide from two fragments using the ligase BS149-DM+L217H+M222P with the coupling position having been identified by hydrolysis of Exenatide using the endoprotease BS149-DM+L217H+C221S+M222P (Example 6).

Example 8: Identification of a Non-Cyclic Oligopeptide Fragment Suitable for the Enzymatic Cyclisation to a Cyclic Peptide Using BS149-DM+C221S as the Endoprotease 800 μL of phosphate buffer (100 mM, pH 8.0) was added to a 100 μL stock solution of the cyclic peptide ┌─ Ala-Cys-Lys-Asn-Gly-Gln-Thr-Asn-Cys-Tyr-Gln-Ser-Tyr ─┐
└───────────────────────────────────────────────────────┘

(0.01 mmol in 1 mL water) containing 5 mg/mL dithiotreitol. To this mixture 5.5 μg of the serine endoprotease BS149-DM+C221S was added and the reaction mixture was shaken (150 rpm) at room temperature. After 30 min a 550 μL aliquot of the reaction mixture was withdrawn and quenched with 500 μL MSA/water (1/99, v/v) and analyzed by LC-MS and MS-MS of the single product peak. The MS-MS analysis indicated that the cyclic peptide was hydrolysed at one position to obtain H-Ala-Cys-Lys-Asn-Gly-Gln-Thr-Asn-Cys-Tyr-Gln-Ser-Tyr-OH On the basis of these results it was determined to use H-Ala-Cys-Lys-Asn-Gly-Gln-Thr-Asn-Cys-Tyr-Gln-Ser-Tyr-OCam.2TFA in the design of an enzymatic peptide cyclisation process according to the invention. Example 9 shows a reduction to practice of the designed process.

Example 9: Synthesis of a Cyclic Peptide from a Non-Cyclic Oligopeptide Using BS149-DM+M222G as the Cyclase The linear oligopeptide identified in Example 8 was used for the synthesis of a cyclic oligopeptide. 800 μL of phosphate buffer (100 mM, pH 8.0) was added to a 100 μL stock solution of the oligopeptide C-terminal Cam-ester with an N-terminal free amine (H-Ala-Cys-Lys-Asn-Gly-Gln-Thr-Asn-Cys-Tyr-Gln-Ser-Tyr-OCam.2TFA (0.01 mmol in 1 mL water) containing 5 mg/mL dithiotreitol. To this mixture 5.5 μg of the cyclase BS149-DM+M222G was added and the reaction mixture was shaken (150 rpm) at room temperature. After 30 min a 550 μL aliquot of the reaction mixture was withdrawn and quenched with 500 μL MSA/water (1/99, v/v) and analyzed by LC-MS. The product, hydrolysed C-terminal Cam-ester and remaining Cam-ester starting material peaks were integrated. The amount of cyclic oligopeptide product was 83%.

Conclusion: clearly, it is possible to design an enzymatic process for the cyclisation of a linear oligopeptide using the cyclase BS149-DM+M222G with the coupling position having been identified by hydrolysis of a cyclic peptide using the endoprotease BS149-DM+C221S (Example 8).

Example 10: Identification of Oligopeptide Fragments Suitable for the Enzymatic Synthesis of Lixisenatide Using BS149-DM+L217H+C221S+M222P as the Endoprotease 1 mg of Lixisenatide (H-His$^1$-Gly$^2$-Glu$^3$-Gly$^4$-Thr$^5$-Phe$^6$-Thr$^7$-Ser$^8$-Asp$^9$-Leu$^1$-Ser$^{11}$-Lys$^{12}$-Gln$^{13}$-Met$^{14}$-Glu$^{15}$-Glu$^{16}$-Glu$^{17}$-Ala$^{18}$-Val$^{19}$-Arg$^{20}$-Leu$^{21}$-Phe$^{22}$-Ile$^{23}$-Glu$^{24}$Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Ser$^{38}$-Lys$^{39}$-Lys$^{40}$-Lys$^{41}$-Lys$^{42}$-Lys$^{43}$-Lys$^{44}$-NH$_2$) was dissolved in 1 mL of phosphate buffer (1N, pH8). To this solution 20 μL of BS149-DM+L217H+C221S+M222P (0.7 mg/mL) was added and the mixture was analyzed by LC-MS every 30 minutes. After mass analysis of the different fragments observed by LC-MS it was shown that Exenatide was preferentially cleaved into three fragments, i.e. H-His$^1$-Gly$^2$-Glu$^3$-Gly$^4$-Thr$^5$-Phe$^6$-Thr$^7$-Ser$^8$-Asp$^9$-Leu$^{10}$-Ser$^{11}$-Lys$^{12}$-Gln$^{13}$-Met$^{14}$-Glu$^{15}$-Glu$^{16}$-Glu$^{17}$-Ala$^{18}$-Val$^{19}$-Arg$^{20}$-Leu$^{21}$-OH, H-Phe$^{22}$-Ile$^{23}$-Glu$^{24}$-OH and H-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Ser$^{38}$-Lys$^{39}$-Lys$^{40}$-Lys$^{41}$-Lys$^{42}$-Lys$^{43}$-Lys$^{44}$-NH$_2$ On the basis of these results it was determined to use H-His$^1$-Gly$^2$-Glu$^3$-Gly$^4$-Thr$^5$-Phe$^6$-Thr$^7$-Ser$^8$-Asp$^9$-Leu$^{10}$-Ser$^{11}$-Lys$^{12}$-Gln$^{13}$-Met$^{14}$-Glu$^{15}$-Glu$^{16}$-Glu$^{17}$-Ala$^{18}$-Val$^{19}$-Arg$^{20}$-Leu$^{21}$-OCam-Leu-OH (the first fragment mentioned in the previous paragraph) as the first fragment (C-terminal ester) and H-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Ser$^{38}$-Lys$^{39}$-Lys$^{40}$-Lys$^{41}$-Lys$^{42}$-Lys$^{43}$-Lys$^{44}$-NH$_2$.8TFA (a combination of the last two fragments mentioned in the previous paragraph) as the second fragment (oligopeptide nucleophile having an N-terminally unprotected amine) in the design of an enzymatic peptide synthesis process according to the invention. Example 11 shows a reduction to practice of the designed process.

Example 11: Synthesis of Lixisenatide from Two Fragments Using BS149-DM+L217H+M222P as the Ligase 5.7 mg of H-His$^1$-Gly$^2$-Glu$^3$-Gly$^4$-Thr$^5$-Phe$^6$-Thr$^7$-Ser$^8$-Asp$^9$-Leu$^{10}$-Ser$^{11}$-Lys$^{12}$-Gln$^{13}$-Met$^{14}$-Glu$^{15}$-Glu$^{16}$-Glu$^{17}$-Ala$^{18}$-Val$^{19}$-Arg$^{20}$-Leu$^{21}$-OCam-Leu-OH.4TFA (H-1-21-OCam-Leu-OH) and 5.3 mg of H-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Ser$^{38}$-Lys$^{39}$-Lys$^{40}$-Lys$^{41}$-Lys$^{42}$-Lys$^{43}$-Lys$^{44}$-NH$_2$.8TFA (H-22-44-NH$_2$) were dissolved in 250 μL phosphate buffer (1N, pH 8) and the pH was adjusted to pH 8.1 using aqueous NaOH (5N). 40 μL of BS149-DM+L217H+M222P (0.4 mg/mL) was added and the reaction mixture was shaken (200 rpm) at ambient temperature.

Figure 5:
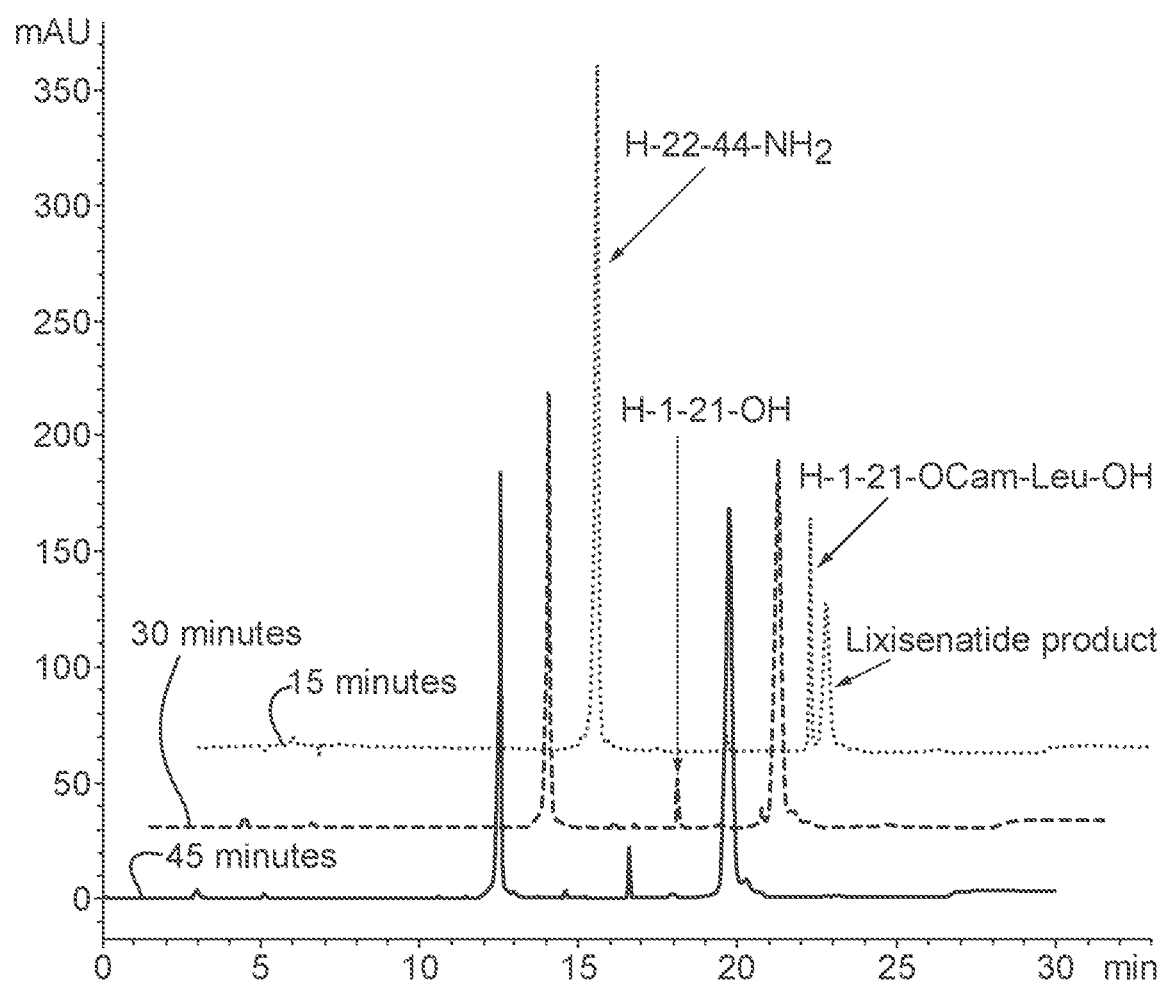
FIG. 5: Synthesis of Lixisenatide using BS149-DM+L217H+M222P ligase mutant.

Aliquots of 20 µL were withdrawn after 15, 30 and 45 minutes and quenched with 0.5 mL MSA/water (1/9, v/v) and analysed by LC-MS (FIG. 5). The synthesis of Lixisenatide was very successful (93% yield).

Conclusion: clearly, it is possible to design an enzymatic process for Lixisenatide from two fragments using the ligase BS149-DM+L217H+M222P with the coupling position having been identified by hydrolysis of Lixisenatide using the endoprotease BS149-DM+L217H+C221S+M222P (Example 10).

Example 12: Coupling of a Pentapeptide Selectively to the N-Terminus of the A-Chain of Human Insulin 5 mg of human insulin (Cas #11061-68-0) and 2.5 mg of Ac-Asp-Phe-Ser-Lys-Leu-OCam-Leu-OH.TFA were dissolved in 200 µL DMF. Subsequently, 200 µL of phosphate buffer (1 M, pH 8.0) and 200 µL $H_2O$ containing 20 µg of the BS149-DM+M222G mutant were added and the reaction mixture was shaken (150 rpm) at room temperature. After 60 min a 100 µL aliquot of the reaction mixture was withdrawn and quenched with 500 µL MSA/water (1/99, v/v) and analyzed by LC-MS, showing that 92% of the insulin starting material was converted to a single product, i.e. Ac-Asp-Phe-Ser-Lys-Leu- coupled to the N-terminus of the insulin A-chain.

Conclusions: Evidently, peptide C-terminal Cam-ester can be selectively coupled to the A-chain of human insulin.

Example 13: Coupling of a Pentapeptide to the N-Terminus of the A- and B-Chain of Human Insulin 5 mg of human insulin (Cas #11061-68-0) and 5 mg of Ac-Asp-Phe-Ser-Lys-Leu-OCam-Leu-OH.TFA were dissolved in 200 µL DMF. Subsequently, 200 µL of phosphate buffer (1 M, pH 8.0) and 200 µL $H_2O$ containing 55 µg of BS149-DM+M222G+L217F mutant were added and the reaction mixture was shaken (150 rpm) at room temperature. After 60 min a 100 µL aliquot of the reaction mixture was withdrawn and quenched with 500 µL MSA/water (1/99, v/v) and analyzed by LC-MS, showing that the insulin starting material was completely consumed and converted to three product peaks, i.e. 1) Ac-Asp-Phe-Ser-Lys-Leu- coupled to the N-terminus of the Insulin A-chain (22 area %), 2) Ac-Asp-Phe-Ser-Lys-Leu- coupled to the N-terminus of the insulin B-chain (3 area %) and 3) Ac-Asp-Phe-Ser-Lys-Leu- coupled to the N-terminus of both the Insulin A- and B-chain (75 area %).

Conclusions: Evidently, peptide C-terminal Cam-ester can be coupled to both the A- and B-chain of human insulin

Example 14: Identification of a non-cyclic oligopeptide fragment suitable for the enzymatic cyclisation to a cyclic peptide using BS149-DM+C221S as the endoprotease 800 µL of phosphate buffer (100 mM, pH 8.0) was added to a 100 µL stock solution of the cyclic peptide (0.01 mmol in 1 mL DMSO). To this mixture 5.5 µg of the serine endoprotease BS149-DM+C221S was added and the reaction mixture was shaken (150 rpm) at room temperature. After 30 min a 550 µL aliquot of the reaction mixture was withdrawn and quenched with 500 µL MSA/water (1/99, v/v) and analysed by LC-MS and MS-MS of two product peaks. The MS-MS analysis indicated that the cyclic peptide was hydrolysed at two positions to obtain H-Gly-Ile-Gly-Thr-Pro-Ile-Ser-Phe-Tyr-Gly-Gly-Gly-Ala-Gly-His-Val-Pro-Glu-Tyr-Phe-Val-Gly-Ile-OH and H-Gly-Gly-Gly-Ala-Gly-His-Val-Pro-Glu-Tyr-Phe-Val-Gly-Ile-Gly-Ile-Gly-Thr-Pro-Ile-Ser-Phe-Tyr-OH.

On the basis of these results it was determined to use H-Gly-Ile-Gly-Thr-Pro-Ile-Ser-Phe-Tyr-Gly-Gly-Gly-Ala-Gly-His-Val-Pro-Glu-Tyr-Phe-Val-Gly-Ile-OH-O Cam-Leu-OH.TFA in the design of an enzymatic peptide cyclisation process according to the invention. Example 15 shows a reduction to practice of the designed process.

Example 15: Synthesis of Microcin J25, Cyclisation of the Linear C-Terminal Cam-Ester The cyclization reaction was performed using 1 mg linear Microcin J25 C-terminal Cam-ester (H-Gly-Ile-Gly-Thr-Pro-Ile-Ser-Phe-Tyr-Gly-Gly-Gly-Ala-Gly-His-Val-Pro-Glu-Tyr-Phe-Val-Gly-Ile-OCam-Leu-OH.TFA) in 1 mL phosphate buffer (100 mM, pH 8.0) supplemented with DMSO (20 vol %). To this reaction mixture, 10 µg of BS149-DM was added and the reaction was analyzed by LC-MS after 30 min. Conversion to cyclic product was measured by integrating the starting material, product and hydrolyzed Cam-ester peaks. The amount of product after 30 min was 82% and the amount of hydrolysis 18%. The Cam-ester starting material was completely consumed.

In a second experiment, linear Microcin J25 C-terminal Cam-ester was dissolved in DMSO (100 mg/ml) and dosed in time (20 µl every 15 min) to an enzyme solution (10 µg BS-149-DM) in 200 µl phosphate buffer (100 mM, pH 8.0). The pH was continuously kept at 8.0 using 5 N aqueous NaOH. The reaction was analyzed by LC-MS after 150 min as described above. The linear Microcin J25 C-terminal Cam-ester was fully consumed, the amount of product was 81% and hydrolysis 19%.

Conclusions: Evidently, BS149-DM can efficiently be used for the head-to-tail cyclisation of linear peptides. High concentrations of cyclic peptide can be obtained when dosing the linear peptide to the enzyme solution.

Example 16: Coupling of Exenatide Cam-Ester to Human Serum Albumin 10 mg of Exenatide (extended with a 4 amino acid C-terminal recognition sequence, indicated in bold)C-terminal Cam-ester (H-His-Gly-Glu-Gly-Thr-Phe-Thr-Ser-Asp-Leu-Ser-Lys-Gln-Met-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-Phe-Ser-Lys-Leu-OCam-Leu-OH (Exenatide-Phe-Ser-Lys-Leu-OCam-Leu-OH) was added to 20 mg of Human Serum Albumin (extended with a 3 amino acid N-terminal recognition sequence, indicated in bold, one Gly-Ile-Gly-Thr-Pro-Ile-Ser-Phe-Tyr-Gly-Gly-Gly-Ala-Gly-His-Val-Pro-Glu-Tyr-Phe-Val-Gly-Ile letter code: SYRDAHKSEVAHRFKDLGEENFKALVLIA-FAQYLQQCPFEDHVKLVNEVTEFAKTCVADESAEN-CDKSLH TLFGDKLCTVATLRETYGEMADCCAKQEP-ERNECFLQHKDDNPNLPRLVRPEVDVMCTAFHDNE-ETFLKK YLYEIARRHPYFYAPELLFFAKRYKAAFTEC-CQAADKAALLPKLDELRDEGKASSAKQRLKCASL-QKFGE RAFKAWAVARLSQRFPKAEFAEVSKLVTDLT-KVHTECCHGDLLECADDRADLAKYICENQDSISSK-LKEC CEKPLLEKSHCIAEVENDEMPADLPSLAADFV-ESKDVCKNYAEAKDVFLGMFLYEYARRHPDYSVV-LLLR LAKTYETTLEKCCAAADPHECYAKVFDEFKP-LVEEP

SEQUENCES

AAAGNEGTSGSSSTVGYPGKYPSVIAVGAVDSSNQRASFSSVGPELDVMA

PGVSIQSTLPGNKYGAYNGTSMASPHVAGAAALILSKHPNWTNTQVRSSL

ENTTTKLGDSFYYGKGLINVQAAAQ

SEQ ID NO 3: subtilisin BPN' variant with deletion of Ca$^{2+}$ binding loop and S221C and preferably P225 mutation (denoted as P225X)

AQSVPYGVSQIKAPALHSQGYTGSNVKVAVIDSGIDSSHPDLKVAGGASM

VPSETNPFQDNNSHGTHVAGTVAAVAPSASLYAVKVLGADGSGQYSWIIN

GIEWAIANNMDVINMSLGGPSGSAALKAAVDKAVASGVVVVAAAGNEGTS

GSSSTVGYPGKYPSVIAVGAVDSSNQRASFSSVGPELDVMAPGVSIQSTL

PGNKYGAYNGTCMASXHVAGAAALILSKHPNWTNTQVRSSLENTTTKLGD

SFYYGKGLINVQAAAQ

SEQUENCES

SEQ ID NO 4: subtilisin BPN' variant with preferred mutation positions compared to SEQ ID NO 3

AXXVXYGVXQIKAPALHSQGYTGSNVKVAVXDSGIDSSHPDLXVAGGASX

VPSETNPFQDNNSHGTHVAGTVXAVAPSASLYAVKVLGADGSGQYSWIIN

GIEWAIANNMDVINMSLGGPSGSAALKAAVDKAVASGVVVVAAAGNXGTS

GSSSTVXYPXKYPSVIAVGAVDSSNQRAXFSSVGPELDVMAPGVSIXSTL

PGXKYGAXXGTCMASXHVAGAAALILSKHPNWTNTQVRSSLENTXTKLGD

SFYYGKGLINVXAAAQ

SEQ ID NO 5: The segment of E. coli/B. subtilis shuttle vector pBES:Ptl149DM His containing the B. subtilis-derived subtilisin (aprE) promoter region (bp 1-197, Takara), the BPN' signal sequence (bp 198-287), the BPN' prodomain (bp 288-518), the mature BS149-DM, 6×Histag, stop codon. From nucleotide 1590 onwards the sequence follows pBES from Takara.

```
  1  ACTAGTGTTC TTTTCTGTAT GAAAATAGTT ATTTCGAGTC TCTACGGAAA TAGCGAGAGA

61  TGATATACCT AAATAGAGAT AAAATCATCT CAAAAAAATG GGTCTACTAA AATATTATTC

121  CATCTATTAC AATAAATTCA CAGAATAGTC TTTTAAGTAA GTCTACTCTG AACTTAAGCA

181  AAAGGAGAGG GACGCGT GTG AGA GGC AAA AAA GTA TGG ATC AGT TTG CTG TTT
     RBS        MluI   Val Arg Gly Lys Lys Val Trp Ile Ser Leu Leu Phe
                      -107    -105                -100

234  GCT TTA GCG TTA ATC TTT ACG ATG GCG TTC GGC AGC ACA TCC TCT GCC
     Ala Leu Ala Leu Ile Phe Thr Met Ala Phe Gly Ser Thr Ser Ser Ala
     -95             -90              -85                      -80

282  CAG GCG GCA GGG AAA TCA AAC GGG GAA AAG AAA TAT ATT GTC GGG TTT
     Gln Ala Ala Gly Lys Ser Asn Gly Glu Lys Lys Tyr Ile Val Gly Phe
                 -75                 -70                      -65

330  AAA CAG ACA ATG AGC ACG ATG AGC GCC GCT AAG AAG AAA GAT GTC ATT
     Lys Gln Thr Met Ser Thr Met Ser Ala Ala Lys Lys Lys Asp Val Ile
                 -60              -55                  -50

378  TCT GAA AAA GGC GGG AAA GTG CAA AAG CAA TTC AAA TAT GTA GAC GCA
     Ser Glu Lys Gly Gly Lys Val Gln Lys Gln Phe Lys Tyr Val Asp Ala
             -45                 -40                  -35

426  GCT TCA GCT ACA TTA AAC GAA AAA GCT GTA AAA GAA TTG AAA AAA GAC
     Ala Ser Ala Thr Leu Asn Glu Lys Ala Val Lys Glu Leu Lys Lys Asp
         -30              -25                  -20

474  CCG AGC GTC GCT TAC GTT GAA GAA GAT CAC GTA GCA CAC GCG ATG GCG
     Pro Ser Val Ala Tyr Val Glu Glu Asp His Val Ala His Ala Met Ala
     -15              -10                  -5                     1

522  AAG TGC GTG TCT TAC GGC GTA GCG CAA ATT AAA GCC CCT GCT CTG CAC
     Lys Cys Val Ser Tyr Gly Val Ala Gln Ile Lys Ala Pro Ala Leu His
                  5                  10                 15

570  TCT CAA GGC TAC ACT GGA TCA AAT GTT AAA GTA GCG GTT CTT GAC AGC
     Ser Gln Gly Tyr Thr Gly Ser Asn Val Lys Val Ala Val Leu Asp Ser
                 20                  25                  30

618  GGT ATC GAT TCT TCT CAT CCT GAT TTA AAC GTA GCA GGC GGA GCC AGC
     Gly Ile Asp Ser Ser His Pro Asp Leu Asn Val Ala Gly Gly Ala Ser
                 35                  40                  45

666  TTC GTT CCT TCT GAA ACA AAT CCT TTC CAA GAC AAC AAC TCT CAC GGA
     Phe Val Pro Ser Glu Thr Asn Pro Phe Gln Asp Asn Asn Ser His Gly
     50                  55                  60                  65
```

```
 714   ACT CAC GTT GCC GGC ACA GTT TTG GCT GTT GCG CCA AGC GCA TCA CTT
       Thr His Val Ala Gly Thr Val Leu Ala Val Ala Pro Ser Ala Ser Leu
                    70              74* 84  85                      90

762   TAC GCT GTA AAA GTT CTC GGT GCT GAC GGT TCC GGC CAA TAC AGC TGG
       Tyr Ala Val Lys Val Leu Gly Ala Asp Gly Ser Gly Gln Tyr Ser Trp
                    95              100                 105

810   ATC ATT AAC GGA ATC GAG TGG GCG ATC GCA AAC AAT ATG GAC GTT ATT
       Ile Ile Asn Gly Ile Glu Trp Ala Ile Ala Asn Asn Met Asp Val Ile
                    110             115                 120

858   AAC ATG AGC CTC GGC GGA CCT TCT GGT TCT GCT GCT TTA AAA GCG GCA
       Asn Met Ser Leu Gly Gly Pro Ser Gly Ser Ala Ala Leu Lys Ala Ala
                    125             130                 135

906   GTT GAT AAA GCC GTT GCA TCC GGC GTC GTA GTC GTT GCG GCA GCC GGT
       Val Asp Lys Ala Val Ala Ser Gly Val Val Val Val Ala Ala Ala Gly
                    140             145                 150

954   AAC TCT GGC ACT TCC GGC AGC TCA AGC ACA GTG AGC TAC CCT GCT AAA
       Asn Ser Gly Thr Ser Gly Ser Ser Ser Thr Val Ser Tyr Pro Ala Lys
                    155             160                 165             170

1002   TAC CCT TCT GTC ATT GCA GTA GGC GCT GTT GAC AGC AGC AAC CAA AGA
       Tyr Pro Ser Val Ile Ala Val Gly Ala Val Asp Ser Ser Asn Gln Arg
                    175             180                 185

1050   GCA CCG TTC TCA AGC GTA GGA CCT GAG CTT GAT GTC ATG GCA CCT GGC
       Ala Pro Phe Ser Ser Val Gly Pro Glu Leu Asp Val Met Ala Pro Gly
                    190             195                 200

1098   GTA TCT ATC TGT AGC ACG CTT CCT GGA GGC AAA TAC GGG GCG CTT TCT
       Val Ser Ile Cys Ser Thr Leu Pro Gly Gly Lys Tyr Gly Ala Leu Ser
                    205             210                 215

1146   GGT ACG TGC ATG GCA TCT GCG CAC GTT GCC GGA GCG GCT GCT TTG ATT
       Gly Thr Cys Met Ala Ser Ala His Val Ala Gly Ala Ala Ala Leu Ile
                    220             225                 230

1194   CTT TCT AAG CAC CCG AAC TGG ACA AAC ACT CAA GTC CGC AGC AGT TTA
       Leu Ser Lys His Pro Asn Trp Thr Asn Thr Gln Val Arg Ser Ser Leu
       235                 240                 245                 250

1242   GAA AAC ACC GCT ACA AAA CTT GGT GAT TCT TTC TAC TAT GGA AAA GGG
       Glu Asn Thr Ala Thr Lys Leu Gly Asp Ser Phe Tyr Tyr Gly Lys Gly
                    255                 260                 265

1290   CTG ATC AAC GTA GAA GCG GCA GCT CAG CAC CAC CAC CAC CAC CAC TAA
       Leu Ile Asn Val Glu Ala Ala Ala Gln His His His His His His ---
                    270             275                 280

1338   AACATAAAAA ACCGGCCTTG GCCCCGCCGG TTTTTTATTA TTTTTCTTCC TCCGCATGTT

1398   CAATCCGCTC CATAATCGAC GGATGGCTCC CTCTGAAAAT TTTAACGAGA AACGGCGGGT

1458   TGACCCGGCT CAGTCCCGTA ACGGCCAAGT CCTGAAACGT CTCAATCGCC GCTTCCCGGT

1518   TTCCGGTCAG CTCAATGCCG TAACGGTCGG CGGCGTTTTC CTGATACCGG GAGACGGCAT

1578   TCGTAATCGG ATGGATCC
                   BamHI
*Deletion with respect to BPN' of amino acid 72-80 (Val-Ala-Ala-Leu-Asn-Asn-Ser-Ile-Gly);
GTT GCG GCT CTT AAT AAC TCA ATC GGT.
```

---

The invention claimed is:

1. A process for enzymatically synthesizing an (oligo) peptide, the (oligo)peptide comprising a first (oligo)peptide fragment and a second (oligo)peptide fragment, the process comprising:

(A) identifying the first (oligo)peptide fragment and the second (oligo)peptide fragment as (oligo)peptide fragments obtainable by enzymatic hydrolysis of the (oligo) peptide by a serine endoprotease,
   wherein the serine endoprotease is a subtilisin BPN' variant or a homologue thereof, having:

a deletion of the amino acids corresponding to positions 75-83; and a serine at the amino acid position corresponding to S221; and (B) enzymatically condensing a C-terminal ester or thioester of the first (oligo)peptide fragment and an N-terminally unprotected amine of the second (oligo)peptide fragment using a ligase,
   wherein the ligase is a subtilisin BPN' variant or a homologue thereof, having:

a deletion of the amino acids corresponding to positions 75-83; and
a mutation at the amino acid position corresponding to S221, the mutation being S221C or S221 selenocysteine;
wherein the amino acid positions in (A) and (B) correspond to the amino acid positions of the subtilisin BPN' amino acid sequence of SEQ ID NO: 2 and wherein the subtilisin BPN' variant or a homologue has at least 90% sequence identity to the amino acid sequence of SEQ ID NO: 2.

2. The process according to claim 1, wherein the synthesis over hydrolysis ratio of the ligase divided by the synthesis over hydrolysis ratio of the serine endoprotease is at least 100.

3. The process according to claim 1, wherein the position corresponding to P225 of the serine endoprotease is not mutated (i.e. is a proline) or the serine endoprotease has a mutation at the amino acid position corresponding to P225 selected from the group consisting of P225N, P225D, P225S, P225C, P225G, P225A, P225T, P225V, P225I, P225L, P225H and P225Q.

4. The process according to claim 1, wherein in the second (oligo)peptide fragment of (B) the C-terminus is provided with a protective group and/or one or more side-chain functionalities are provided with a protective group.

5. The process according to claim 1, wherein the ligase is a subtilisin BPN' variant or homologue thereof
having a mutation at the amino acid position corresponding to P225, the mutation being selected from the group consisting of P225N, P225D, P225S, P225C, P225G, P225A, P225T, P225V, P225I, P225L, P225H and, P225Q;
wherein the amino acid positions are defined according to the sequence of subtilisin BPN' represented by SEQUENCE ID NO: 2.

6. The process according to claim 1, wherein the (oligo)peptide comprises the amino acid sequence of exenatide.

7. Process according to claim 6, wherein the first fragment is His$^1$-Gly$^2$-Glu$^3$-Gly$^4$-Thr$^5$-Phe$^6$-Thr$^7$-Ser$^8$-Asp$^9$-Leu$^{10}$-Ser$^{11}$-Lys$^{12}$-Gln$^{13}$-Met$^{14}$-Glu$^{15}$-Glu$^{16}$-Glu$^{17}$-Ala$^{18}$-Val$^{19}$-Arg$^{20}$-Leu$^{21}$-(thio)ester (1-21-(thio)ester) or a segment thereof at least comprising Arg$^{20}$-Leu$^{21}$-(thio)ester, and the second fragment is H-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser$^{39}$-NH$_2$ (H-22-39-NH$_2$) or a segment thereof at least comprising H-Phe$^{22}$-Ile$^{23}$, wherein the superscripts following the amino acid three-letter code refer to the position of said amino acid in Exenatide.

8. Process according to claim 6, wherein the first fragment is His$^1$-Gly$^2$-Glu$^3$-Gly$^4$-Thr$^5$-Phe$^6$-Thr$^7$-Ser$^8$-Asp$^9$-Leu$^{10}$-Ser$^{11}$-Lys$^{12}$-Gln$^{13}$-Met$^{14}$-Glu$^{15}$-Glu$^{16}$-Glu$^{17}$-Ala$^{18}$-Val$^{19}$-Arg$^{20}$-Leu$^{21}$-Phe$^{22}$-Ile$^{23}$-Glu$^{24}$-(thio)ester) or a segment thereof at least comprising Ile$^{23}$-Glu$^{24}$-(thio)ester and the second fragment is H-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Pro$^{38}$-Ser$^{39}$-NH$_2$ or a segment thereof at least comprising H-Trp$^{25}$-Leu$^{26}$, wherein the superscripts following the amino acid three-letter code refer to the position of said amino acid in Exenatide.

9. The process according to claim 1, wherein the (oligo)peptide comprises the amino acid sequence of thymosin-alpha-1.

10. Process according to claim 9, wherein the first fragment is Ac-Ser$^1$-Asp$^2$-Ala$^3$-Ala$^4$-Val$^5$-Asp$^6$-Thr$^7$-Ser$^8$-Ser$^9$-Glu$^{10}$-Ile$^{11}$-Thr$^{12}$-Thr$^{13}$-Lys$^{14}$-(thio)ester or a segment thereof at least comprising Thr$^{13}$-Lys$^{14}$-(thio)ester and the second fragment is H-Asp$^{15}$-Leu$^{16}$-Lys$^{17}$-Glu$^{18}$-Lys$^{19}$-Lys$^{20}$-Glu$^{21}$-Val$^{22}$-Val$^{23}$-Glu$^{24}$-Glu$^{25}$-Ala$^{26}$-Glu$^{27}$-Asn$^{28}$-OH or a segment thereof at least comprising is Asp$^{15}$-Leu$^{16}$ wherein the superscripts following the amino acid three-letter code refer to the position of said amino acid in Thymosin-alpha-1.

11. The process according to claim 1, wherein the (oligo)peptide comprises the amino acid sequence of lixisenatide.

12. Process according to claim 11, wherein the first fragment is His$^1$-Gly$^2$-Glu$^3$-Gly$^4$-Thr$^5$-Phe$^6$-Thr$^7$-Ser$^8$-Asp$^9$-Leu$^{10}$-Ser$^{11}$-Lys$^{12}$-Gln$^{13}$-Met$^{14}$-Glu$^{15}$-Glu$^{16}$-Glu$^{17}$-Ala$^{18}$-Val$^{19}$-Arg$^{20}$-Leu$^{21}$-(thio)ester (1-21-(thio)ester) or a segment thereof at least comprising Arg$^{20}$-Leu$^{21}$-(thio)ester and the second is H-Phe$^{22}$-Ile$^{23}$-Glu$^{24}$-Trp$^{25}$-Leu$^{26}$-Lys$^{27}$-Asn$^{28}$-Gly$^{29}$-Gly$^{30}$-Pro$^{31}$-Ser$^{32}$-Ser$^{33}$-Gly$^{34}$-Ala$^{35}$-Pro$^{36}$-Pro$^{37}$-Ser$^{38}$-Lys$^{39}$-Lys$^{40}$-Lys$^{41}$-Lys$^{42}$-Lys$^{43}$-Lys$^{44}$-NH$_2$ (H22-44-NH$_2$) or a segment thereof, at least comprising H-Phe$^{22}$-Ile$^{23}$, wherein the superscripts following the amino acid three-letter code refer to the position of said amino acid in Lixisenatide.

13. A process for enzymatically synthesizing a cyclic (oligo)peptide of at least 12 amino acid units, the process comprising:
(A) identifying a non-cyclic oligopeptide obtainable by enzymatic hydrolysis of the cyclic (oligo)peptide by a serine endoprotease;
wherein the serine endoprotease is a subtilisin BPN' variant or a homologue thereof, having:
a deletion of the amino acids corresponding to positions 75-83; and
a serine at the amino acid position corresponding to S221; and
(B) enzymatically coupling a C-terminal ester or thioester of the non-cyclic (oligo)peptide and an N-terminal unprotected amine of the non-cyclic (oligo)peptide using a cyclase,
wherein the cyclase is a, a subtilisin BPN' variant or a homologue thereof, having:
a deletion of the amino acids corresponding to positions 75-83; and
a mutation at the amino acid position corresponding to 5221, the mutation being S221C or S221 selenocysteine;
wherein the amino acid positions in (A) and (B) correspond to the amino acid positions of the subtilisin BPN' amino acid sequence of SEQ ID NO: 2 and wherein the subtilisin BPN' variant or a homologue has at least 90% sequence identity to the amino acid sequence of SEQ ID NO: 2.

14. The process according to claim 1, wherein the subtilisin BPN' variant or a homologue has at least 94% sequence identity to the amino acid sequence of SEQUENCE ID NO: 2.

15. The process according to claim 1, wherein the subtilisin BPN' variant or a homologue has at least 96% sequence identity to the amino acid sequence of SEQUENCE ID NO: 2.

16. The process according to claim 1, wherein the subtilisin BPN' variant or a homologue has at least 98% sequence identity to the amino acid sequence of SEQUENCE ID NO: 2.

17. The process according to claim 13, wherein the subtilisin BPN' variant or a homologue has at least 94% sequence identity to the amino acid sequence of SEQUENCE ID NO: 2.

18. The process according to claim 13, wherein the subtilisin BPN' variant or a homologue has at least 96% sequence identity to the amino acid sequence of SEQUENCE ID NO: 2.

19. The process according to claim 13, wherein the subtilisin BPN' variant or a homologue has at least 98% sequence identity to the amino acid sequence of SEQUENCE ID NO: 2.

* * * * *